United States Patent
Ma et al.

(10) Patent No.: US 9,453,062 B2
(45) Date of Patent: Sep. 27, 2016

(54) GLUCOSE DEPENDENT INSULINOTROPIC POLYPEPTIDE ANALOGS, PHARMACEUTICAL COMPOSITIONS AND USE THEREOF

(75) Inventors: Tao Ma, Beijing (CN); Shusen Xu, Beijing (CN); Zhijun Liu, Beijing (CN); Bo Zhang, Beijing (CN); Ning Shen, Beijing (CN); Hai Yang, Beijing (CN); Wei Zhang, Beijing (CN); Yuhua Li, Beijing (CN); Sunghwan Moon, Hwaseong-Si (KR); Maengsup Kim, Beijing (CN)

(73) Assignee: Beijing Hanmi Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 14/125,061

(22) PCT Filed: Jun. 8, 2012

(86) PCT No.: PCT/CN2012/076677
§ 371 (c)(1),
(2), (4) Date: Dec. 9, 2013

(87) PCT Pub. No.: WO2012/167744
PCT Pub. Date: Dec. 13, 2012

(65) Prior Publication Data
US 2014/0162945 A1 Jun. 12, 2014

(30) Foreign Application Priority Data
Jun. 10, 2011 (CN) .......................... 2011 1 0156296

(51) Int. Cl.
| | | |
|---|---|---|
| *A61K 38/22* | (2006.01) |
| *A61K 38/00* | (2006.01) |
| *A61K 38/28* | (2006.01) |
| *A61K 38/26* | (2006.01) |
| *A61K 38/16* | (2006.01) |
| *A61P 3/04* | (2006.01) |
| *A61P 3/10* | (2006.01) |
| *A61P 7/12* | (2006.01) |
| *A61P 19/10* | (2006.01) |
| *C07K 14/605* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/575* | (2006.01) |
| *C07K 14/00* | (2006.01) |

(52) U.S. Cl.
CPC ............. *C07K 14/575* (2013.01); *A61K 38/16* (2013.01); *A61K 38/22* (2013.01); *C07K 14/00* (2013.01); *C07K 14/605* (2013.01); *A61K 38/00* (2013.01)

(58) Field of Classification Search
None
See application file for complete search history.

(56) References Cited

FOREIGN PATENT DOCUMENTS

| | | |
|---|---|---|
| JP | 04-145099 A | 5/1992 |
| JP | 2008-500280 A | 1/2008 |
| WO | WO-2006086769 A2 | 8/2006 |
| WO | 2010011439 A2 | 1/2010 |
| WO | WO 2010011439 A2 * | 1/2010 ........... C07K 14/605 |
| WO | 2010016936 A1 | 2/2010 |
| WO | WO-2010016935 A2 | 2/2010 |
| WO | WO-2010071807 A1 | 6/2010 |
| WO | 2010148089 A1 | 12/2010 |
| WO | 2011094337 A1 | 8/2011 |

OTHER PUBLICATIONS

Examination Report dated Apr. 13, 2016 issued in the counterpart European Application No. 12797613.2.

* cited by examiner

*Primary Examiner* — James H Alstrum Acevedo
*Assistant Examiner* — Thea D'Ambrosio
(74) *Attorney, Agent, or Firm* — Fox Rothschild LLP; Jianming Jimmy Hao

(57) ABSTRACT

The present invention provides a GIP analog, which is derived from GIP (1-29, SEQ ID NO: 1), has both GLP-1 agonist activity and GIPR stimulation activity, and comprises an amino acid sequence represented by the following formula I: Tyr-A2-A3-Gly-Thr-Phe-A7-Ser-Asp-Tyr-Ser-A12-A13-A14-A15-Lys-A17-A18-A19-A20-A21-A22-A23-A24-Trp-Leu-A27-A28-A29-Y. The present invention also provides a pharmaceutical composition comprising the GIP analog and use thereof.

22 Claims, 7 Drawing Sheets

Pharmacokinetics study in mice

GLUCOSE DEPENDENT INSULINOTROPIC POLYPEPTIDE ANALOGS, PHARMACEUTICAL COMPOSITIONS AND USE THEREOF

CROSS REFERENCE

This application is the U.S. National Stage of International Patent Application Serial No. PCT/CN2012/076677, filed on Jun. 8, 2012, which claims the benefit of Chinese Application No. 201110156296.2, filed on Jun. 10, 2011. The contents of the foregoing applications are hereby incorporated by reference in their entireties.

BACKGROUND

Type 2 diabetes mellitus, T2D, is a chronic metabolic disorder which is characterized by increased hepatic glucose production, defective pancreatic beta-cell functions, insulin secretion deficiency and insulin resistance, finally leading to the sustained hyperglycemia situations (Green, et al. Current Pharmaceutical Design, 2004, 10). T2D is also the leading cause of kidney failure, blindness and amputation, and is definitely correlated with the high risk of death from cardiovascular causes in the world. Furthermore, the prevalence of T2D is believed to be a growing factor due to the increasing epidemic of obesity, especially in the developing countries. Although many anti-diabetic treatments have been approved by the FDA (the U.S. Food and Drug Administration), new therapeutic strategies are supposed to achieve better glycemic and body weight controls.

La Barre proposed the concept of incretin (intestinal secretion of insulin) in 1929, which initiated a novel therapy for the treatment of diabetes many years later. Glucagon-like peptide-1 (GLP-1) and glucose-dependent insulinotropic polypeptide (GIP) are the two most potent incretin hormones in human which have ever been discovered and examined extensively during the last 30 years (Baggio and Drucker, Gastroenterology, 2007, 132, 2131-2157). GLP-1 and GIP are released from intestinal endocrine L and K cells, respectively. GLP-1 is a 30 or 31-amino-acid peptide, which is produced from its precursor pre-proglucaon through post-translational gene processing (Orskov, et al. Endocrinology, 1986, 119, 1467-1475). Meanwhile, GIP is secreted as a 42-amino acid peptide and shares approximately 68% sequence homology with GLP-1 (Gallwitz, et al. Regulatory Peptides, 1996, 63, 17-22).

Both GLP-1 and GIP exhibit their physiological functions through bindings to their specific receptors, GLP-1 receptor (GLP-1R) and GIP receptor (GIPR) respectively, which belong to the G-protein coupled receptor family (Seino, et al. Journal of Diabetes Investigation, 2010, 1, 8-23). GLP-1 and GIP are responsible for stimulating insulin secretion after nutrient ingestion as glucose-dependent profile. This glucose-dependent mode of action offers the much lower possibility of hypoglycemia, when compared to other traditional anti-diabetic therapies such as insulin injection, orally administered sulphonylureas and metformin, etc. Moreover, they also stimulate insulin biosynthesis, improve pancreatic beta-cell proliferation, and inhibit beta-cell apoptosis; hence they potentially preserve beta-cell functions and slow the T2D progression (Green, Best Practice & Research Clinical Endocrinology & Metabolism, 2007, 21, 497-516). All these featured properties are leading to the great interest in exploring GLP-1 and GIP as potential therapeutic agents for T2D and other metabolic disorders.

Although GLP-1 and GIP exhibit anti-diabetic potential, they are rapidly degraded by dipeptidyl peptidease-IV (DPP-IV) into inactive forms [GLP-1 (9-37, or 9-36), and GIP (3-42)] and removed from the circulation in vivo (Deacon, et al. Journal of Clinical Endocrinology & Metabolism, 1995, 80, 952-957). This enzyme specifically digests an alanine, proline or hydroxyproline residue in the penultimate N-terminal position. Therefore, endogenous GLP-1 and GIP have very short half-life times in human (2 min and 5-7 min, respectively) due to DPP-IV degradation (Deacon, et al. Hormone and Metabolic Research, 2004, 36, 761-765). That is the reason why exogenous GLP-1 and GIP can't be applied directly for anti-diabetic treatments.

Many research groups have tried to achieve DPP-IV resistance through structural modifications based on native GLP-1 sequence and GIP sequence. First of all, N-terminal extension by diverse chemical substitutions at $His^7$ and $Tyr^1$ positions of GLP-1 and GIP, respectively (Green, et al. Journal of Endocrinology, 2004, 180, 379-388; O'Harte, et al. Diabetes, 1999, 48, 758-765). Secondly, $Ala^8$ and $Glu^9$ in GLP-1, and $Ala^2$ and $Glu^3$ in GIP respectively, have been widely replaced by other amino acids, or even some unusual amino acids (Green, et al. Journal of Molecular Endocrinology, 2003, 31, 529-540; Biological Chemistry, 2003, 384, 1541-1551; Metabolism, 2004, 53, 252-259; Gault, et al. Journal of Endocrinology, 2003, 176, 133-141; Metabolism, 2003, 52, 679-687; Biochemical & Biophysical Research Communications, 2002, 290, 1420-1426; Diabetologia, 2003, 46, 222-230). Lastly, GLP-1 and GIP have been conjugated with short- or long-chain fatty acids to prolong circulation time and bioavailability (Holz and Chepurny, Current Medicinal Chemistry, 2003, 10, 2471-2483; Irwin, et al. Journal of Medicinal Chemistry, 2005, 48, 1244-1250; Journal of Medicinal Chemistry, 2006, 49, 1047-1054). These structural modifications produced various biological activities, along with much improved stabilization against DPP-IV degradation.

Exendin-4, a peptide comprising of 39 amino acids, was firstly isolated and identified from lizard venom in 1992 (Eng, et al. Journal of Biological Chemistry, 1992, 267, 7402-7405). Exendin-4 shares approximately 53% amino acid homology with GLP-1 sequence, and subsequent experiments demonstrated exendin-4 was a pure and potent GLP-1 receptor agonist in vitro and in vivo. It is no wonder that exendin-4 exhibits quite similar physiological properties to native GLP-1, and also regulates gastric emptying, insulin secretion, food intake, and glucagon secretion. Exendin-4 induces blood glucose reduction in normal rodents and in both mice and rats with experimental diabetes (Raufman, Regulatory Peptides, 1996, 61, 1-18). It is much more potent than native GLP-1 in vivo, mainly because of its improved pharmaco-kinetic properties. It has a glycine substitution at position 2 in the sequence, while alanine is present at the same position in the native GLP-1 sequence. Thus, exendin-4 should be stable for DPP-IV degradation, and has a much longer half-life time than native GLP-1 in vivo. Chemically synthesized exendin-4, exenatide co-developed by Amylin and Eli Lilly, was approved by the FDA in 2005 under the trade name of "Byetta" for the treatment of T2D, due to its potent blood glucose lowering features along with comparatively prolonged circulation of action in vivo. Currently, exenatide has to be administered through subcutaneous injection twice daily. A long-acting form of exendin-4, designated exenatide-LAR has been studied extensively in both animal models and human in once weekly profile (Gedulin, et al. Diabetologia, 2005, 48, 1380-1385; Drucker, et al. Lancet, 2008, 372, 1240-1250).

Encouraged by the great success of exenatide, Novo Nordisk developed liraglutide, a long-acting GLP-1 analog, which shares approximately 97% sequence identity to human GLP-1. Based on native GLP-1 (7-37) sequence, liraglutide has an arginine substitution at position 34, and palmitoyl conjugation to the epsilon-amine of Lys at position 26 with gamma-glutamyl as the spacer. The palmitoyl conjugation is believed to achieve DPP-IV protection and significantly prolong its circulation rate in vivo through binding to serum albumin and peptide self-association (Malm-Erjefält, et al. Drug Metabolism and Disposition: the Biological Fate of Chemicals, 2010, 38, 1944-1953). Under the trade name of "Victoza", liraglutide was approved by the EMA (the European Medicines Agency) and the FDA in 2009 and in 2010 respectively for the treatment of T2D with the profile of once daily subcutaneous injection. The exploratory studies of liraglutide indication in obese non-diabetic subjects are now in phase III clinical trial (Astrup, et al. Lancet, 2009, 374, 1606-1616). Other GLP-1 and exendin-4 analogs as pure GLP-1 receptor agonists, such as taspoglutide, albiglutide, and lixisenatide etc, are to date under late clinical development stages.

Although GIP is responsible for approximately 60% of the incretin effect in normal subjects (Nauck, et al. Journal of Clinical Endocrinology and Metabolism, 1986, 63, 492-498), the therapeutic applications of GIP analogs for antidiabetic potential have been largely limited by the diminished or markedly attenuated responsiveness of pancreatic beta-cell towards GIP in some but not all subjects with T2D (Krarup, et al. Metabolism, 1987, 36, 677-682; Jones, et al. Hormone and Metabolic Research, 1989, 21, 23-26). Hence, the reduced insulin secretion induced by GIP was observed after the intravenous administration of the peptide in T2D patients. On the contrary, GLP-1 was shown to stimulate insulin secretion in different stages of T2D subjects effectively (Nauck, et al. Journal of Clinical Investigation, 1993, 91, 301-307).

The reduced insulinotropic effect of GIP was speculated due to chronic desensitization of GIP receptor (Tseng, et al. American Journal of Physiology, 1996, 270, E661-666), or due to the reduced expression of GIP receptor on pancreatic beta-cells in T2D patients (Hoist, et al. Diabetologia, 1997, 40, 984-986). Despite only minor effort has been emphasized on the clinical applications of GIP, it has been demonstrated that GIP contributes to the pathogenesis of T2D to a considerable degree (Meier, et al. Regulatory Peptides, 2002, 107, 1-13). As recently reported, N-terminally modified GIP analogs have been shown to increase insulin response to glucose and lower plasma glucose levels in obese diabetic oblob mice (O'Harte, et al. Journal of Endocrinology, 2000, 165, 639-648).

Furthermore, the reduced release of insulin induced by GIP in T2D is much less evident in pulse administration than in continuous intravenous infusion (Meier, et al. Diabetes, 2004, 53, S220-224). Additionally, the sensitivity of pancreatic beta-cells towards endogenous or exogenous GIP in T2D can be re-established when the hyperglycemia situation is reversed (Piteau, et al. Biochemical and Biophysical Research Communications, 2007, 362, 1007-1012). Thus, the potential application of GIP in the treatment of T2D is now being re-emphasized so far. For example, N-AcGIP alone or in combination with exendin-4 induced significant plasma glucose reduction and improved glucose intolerance in the model of dietary-induced obesity-diabetes (Irwin, et al. Regulatory Peptides, 2009, 153, 70-76).

In consideration of the insulinotropic effects induced by GLP-1 and GIP, it has been demonstrated that the stimulatory action on glucose-dependent insulin release and intracellular cAMP production by GLP-1 and GIP should be additive and synergistic as well (Gallwitz, et al. Journal of Molecular Endocrinology, 1993, 259-268; Siegel, et al. European Journal of Clinical Investigation, 1992, 22, 154-157; Nauck, et al. Journal of Clinical Endocrinology and Metabolism, 1993, 76, 912-917). Many research groups have tried to develop synthetic GLP-1/GIP hybrid peptides to achieve the simultaneous activations of both GLP-1R and GIPR.

Gallwitz reported synthetic GLP-1/GIP chimeric peptides possessing an N-terminal and C-terminal third of one peptide with an exchange comprising the middle portion of the other peptide. Furthermore, hybrid peptides with additional singular mutations in the positions 13 and 15 were prepared as well as chimeras with only an exchange in the C-terminal third. Unfortunately, the binding affinity of these hybrid peptides to GLP-1R was found to be sensitive to GIP-like exchanges in the N-terminal 22 amino acids as well as in positions 13 and 15 (loss of affinity 280-fold to more than 1,000-fold). C-terminal replacement of GLP-1 sequence by GIP reduced the affinity to GLP-1R only 20-fold, and all the hybrid peptides exhibited minimal binding affinity against GIPR (Gallwitz, et al. Endocrinology and Metabolism, 1995, 2, 39-46; Regulatory Peptides, 1996, 63, 17-22).

Hinke also reported a series of five GIP/GLP-1 hybrid peptides to elucidate the binding and activation domains of GIP and GLP-1 in the perspective of the known bioactive domains of GIP. The chimeric peptides synthesized were GLP-1$_{[1-14]}$/GIP$_{[15-30]NH2}$ (CH1), GIP$_{[1-14]}$/GLP-1$_{[15-30]NH2}$ (CH2), GLP-1$_{[1-11]}$/GIP$_{[12-30]NH2}$ (CH3), GIP$_{[1-11]}$/GLP-1$_{[12-18]}$/GIP$_{[19-30]NH2}$ (CH4), and GIP$_{[1-14]}$/GLP-1$_{[15-18]}$/GIP$_{[19-30]NH2}$ (CH5). The subscript amino acid designations for GLP-1 were numbered according to the primary sequence (i.e. GLP-1$_{[7-37]}$=GLP-1$_{[1-31]}$). Through GIPR and GLP-1R transfected CHO cell assays, the added GLP-1 sequence in these chimeras did not contribute to the binding affinity or bioactivity of these peptides at the GIPR (Hinke, et al. Life Sciences, 2004, 75, 1857-1870).

The patent, WO 2010011439, described modified glucagon analogs exhibiting potent GIP receptor activation in addition to glucagon and/or GLP-1 activity. Based on glucagon sequence, the hybrid peptides were developed through substitutions of the middle portion (17-19) with GLP-1 sequence, and replacement of the C-terminus with residues from exendin-4 (30-39). It also claimed alpha, alpha-disubstituted amino acids at positions 2 and 20 respectively, as the most important modifications to achieve DPP-IV protection and simultaneous activations of both GLP-1R and GIPR. The dual GLP-1R/GIPR agonists exhibited much more potency than the pure GLP-1 agonists (such as exendin-4 and liraglutide) in the case of blood glucose level reduction and body weight loss in diet-induced obese (DIO) mice. The dual agonists induced body weight loss and blood glucose level reduction even in GLP-1R knock-out model (DiMarchi and Ma, WO 2010011439, 2009, Jun. 16).

Interestingly, it was reported that the simple co-administration of GIP in addition to GLP-1 did not further augment insulin secretion effect, nor did it lead to more blood glucose lowering in patients with T2D (Mentis, et al. Diabetes, 2011, 60, 1270-1276). This may indicate that the simple combination of GIP and GLP-1 could not potentiate the additivity and synergism of the insulinotropic effectiveness induced by individual GIP and GLP-1 clinically. Coincidently, Gault reported that a single preparation of liraglutide-N-AcGIP was more potent at lowering plasma glucose and insulin secretion stimulation when compared to liraglutide and N-AcGIP or a simple peptide combination in normal male NIH Swiss TO mice and in obese diabetic (ob\ob) mice (Gault, et al. Clinical Science, 2011, 121, 107-117).

SUMMARY OF THE INVENTION

As presented in this invention, GIP analogs based on the native GIP sequence (1-29, SEQ ID NO: 1) are described, in part, to exhibit significant GLP-1 receptor activation, along with maintained GIPR stimulation. This invention also provides pharmaceutical methods of using such GIP analogs for the medication of metabolic disorders, such as diabetes and obesity.

In one aspect, the present invention provides a GIP analog having the activities of both GIP and GLP-1. The activity of GIP and/or GLP-1 can be determined in vivo and in vitro by the person skilled in the art according to the known methods in the art (Fan R, Kang Z, He L, Chan J, Xu G (2011) Exendin-4 Improves Blood Glucose Control in Both Young and Aging Normal Non-Diabetic Mice, Possible Contribution of Beta Cell Independent Effects. PLoS ONE 6(5): e20443. doi:10.1371/journal.pone.0020443; David G Parkes et al., Insulinotropic Actions of Exendin-4 and Glucagon-Like Peptide-1 In Vivo and In Vitro, Metabolism, Vol 50, No 5 (May), 2001: pp 583-589; Jens Juul Holst, The Physiology of Glucagon-like Peptide 1; Physiol Rev 87: 1409-1439, 2007; doi:10.1152/physrev.00034.2006; and M. Shimoda et al., The human glucagon-like peptide-1 analogue liraglutide preserves pancreatic beta cells via regulation of cell kinetics and suppression of oxidative and endoplasmic reticulum stress in a mouse model of diabetes, Diabetologia (2011) 54:1098-1108, DOI 10.1007/s00125-011-2069-9).

For example the EC50 values of each peptide can be determined by the general cAMP induction assay protocol (Meera Kumar et al., A Bioluminescent-Based, HTS-Compatible Assay to Monitor G-Protein-Coupled Receptor Modulation of Cellular Cyclic AMP, ASSAY and Drug Development Technologies, Vol. 5, No. 2, 2007; Yuxin Yan et al., Cell-Based High-Throughput Screening Assay System for Monitoring G Protein-Coupled Receptor Activation Using β-Galactosidase Enzyme Complementation Technology, Journal of Biomolecular Screening, Vol. 7, No. 5, 2002; Thomas C. Rich and Jeffrey W. Karpen, High-Throughput Screening of Phosphodiesterase Activity in Living Cells, Methods in Molecular Biology, vol. 307: Phosphodiesterase Methods and Protocols; Jayne Hesley et al., Stable, Sensitive, Fluorescence-Based Method for Detecting cAMP, BioTechniques 33:691-694 (September 2002); and Christine Williams, cAMP Detection Methods IN HTS: Selecting the Best, Nature Reviews, Drug Discovery Vol. 3, February 2004), such as that described in Example 8 hereinafter.

In one embodiment, the present invention provides an analog of GIP (1-29, SEQ ID NO: 1), which has at least 0.01% of the GLP-1 receptor activation activity of the native GLP-1, such as at least 0.1%, 0.2%, 0.5%, 0.8%, 1%, 3%, 5%, 10%, 20%, 30%, 40%, 50%, 60%, 70%, 80%, 90%, 95%, 99% of the GLP-1 receptor activation activity of the native GLP-1 and/or at least 0.01% of the GIP receptor activation activity of GIP, such as at least 0.1%, 0.2%, 0.5%, 0.8%, 1%, 3%, 5%, 10%, 20%, 30%, 40%, 50%, 60%, 70%, 80%, 90%, 95%, 99% of the GIP receptor activation activity of the native GIP (SEQ ID No. 1), when determined according to the general cAMP induction assay protocol described in Example 8 hereinafter.

The GIP analog may be derived from the sequence of SEQ ID NO: 1 through at least one of the following modifications:

(1) An amino acid substitution at position 7 that induces the activities of GLP-1 receptor activation and GIP receptor activation;

(2) An amino acid substitution at position 13 that improves potency at GLP-1 and GIP receptors;

(3) An amino acid substitution at position 22 that improves potency at GLP-1 and GIP receptors.

Alternatively, the analog may be derived from the sequence of SEQ ID NO: 1 through at least one of the following modifications:

(1) An amino acid substitution at position 7 that induces the activities of GLP-1 receptor activation and GIP receptor activation;

(2) An amino acid substitution at position 13 that improves potency at GLP-1 and GIP receptors;

(3) 1-20 further amino acids extension at C-terminus

In the present invention, the position numbering is defined as that position corresponds to the same position of the amino acid sequence shown herein as SEQ ID No. 1. More specifically, the position is identified by alignment of a sequence with the amino acid sequence shown herein as SEQ ID No. 1.

In an embodiment, the amino acid at position 2 of the GIP analog according to the present invention is Aib, compared with the amino acid sequence of SEQ ID No. 1. This substitution (Ala to Aib) increases DPP-IV stability of the GIP analog thus obtained.

In an embodiment, the amino acid at position 7 of the GIP analog according to the present invention is Thr, compared with the amino acid sequence of SEQ ID No. 1.

In an embodiment, the amino acid at position 13 of the GIP analog according to the present invention possesses aromatic group(s) at its side chain. The amino acid possessing aromatic group(s) at its side chain may be selected from Tyr, derivatives of Tyr, Phe and derivatives of Phe. In one embodiment, the amino acid at position 13 of the GIP analog according to the present invention is Tyr, compared with the amino acid sequence of SEQ ID No. 1.

In an embodiment, the amino acid at position 16 of the GIP analog according to the present invention is a positively-charged amino acid, such as but not limited to Lys or Arg.

In an embodiment, the amino acid at position 17 of the GIP analog according to the present invention is Glu, compared with the amino acid sequence of SEQ ID No. 1.

In an embodiment, the amino acid at position 19 of the GIP analog according to the present invention is Val, compared with the amino acid sequence of SEQ ID No. 1.

In an embodiment, the amino acid at position 20 of the GIP analog according to the present invention is a positively-charged amino acid, such as but not limited to Lys or Arg. In one embodiment, the amino acid at position 20 of the GIP analog according to the present invention is Arg, compared with the amino acid sequence of SEQ ID No. 1.

In an embodiment, the amino acid at position 22 of the GIP analog according to the present invention is substituted by Phe, or derivatives of Phe, for example, unusual amino acids, such as 4'-halo-substituted phenyl alanine, 4'-nitro phenyl alanine, 4'-amine phenyl alanine, 4'-alkyl phenyl alanine, 4'-methoxyl phenyl alanine, 4'-carboxyl phenyl alanine and the like including Cha, Chg, and Phg with saturated or unsaturated cyclic side chain.

In an embodiment, the amino acid at position 29 of the GIP analog according to the present invention is Gly or Gln.

In a further aspect, the GIP analog derived from the sequence of SEQ ID NO: 1 through at least one of the above modifications may be further modified to increase its GLP-1 agonist activity.

In an embodiment, the N-terminal region (1-16) of the GIP analog derived from the sequence of SEQ ID NO: 1 through at least one of the modifications at one or more positions of 2, 7, 13 is fused with the middle region (positions 17-20) of GLP-1 (SEQ ID NO: 1) or exendin-4 sequence (SEQ ID NO: 99) and the C-terminal region (21-29) of GLP-1 (SEQ ID NO: 1) or exendin-4 sequence (SEQ ID NO: 99).

In an embodiment, the middle region of Exendin-4 (amino acid residues 17-20 of SEQ ID NO: 99) is incorporated into the peptide backbone of the GIP analog according to the present invention to improve GLP-1 activity while the GIP receptor activation activity is maintained.

In an embodiment, the C-terminal region of GLP-1$_{[7-37]}$ (amino acid residues 27-35 of SEQ ID NO: 1) is incorporated into the peptide backbone of the GIP analog according to the present invention to improve GLP-1 activity while the GIP receptor activation activity is maintained.

In a further aspect, the GIP analog obtained by fusing with the regions from GLP-1 and/or exendin-4 may be further modified to improve its activity and/or property.

In an embodiment, the C-terminus of the GIP analog according to the present invention is extended by a fragment of exendin-4 (30-39), GPSSGAPPPS (SEQ ID NO. 101).

In an embodiment, the C-terminus is extended with 1 to 10 positively-charged amino acid residues. The positively-charged amino acid residue is Lys and/or Arg, and preferably Lys. The number of the positively-charged amino acid residue is preferably 1 to 6, more preferably 1 to 4, such as 2, 3 or 4 or 5 positively-charged amino acid residue are extended at the C-terminus. In a preferred embodiment, the C-terminus of GIP analog is extended with intervening peptide (IP-1 fragment) KRNRNNIA (SEQ ID NO. 102) from Oxyntomodulin.

In an embodiment, a salt bridge may be formed between the amino acids at positions i and i+4 of the GIP analog according to the present invention, such as positions 12 and 16. In this embodiment, one of the amino acids at positions 12 and 16 is substituted with a negatively-charged amino acid, such as Glu, and the other is a positively-charged amino acid, such as Lys.

In an embodiment, a lactam bridge may be formed between the amino acids at positions i and i+4 of the GIP analog according to the present invention, such as positions 12 and 16. In this embodiment, one of the amino acids at positions 12 and 16 is substituted with a negatively-charged amino acid, such as Glu, and the other is a positively-charged amino acid, such as Lys.

In an embodiment, a salt bridge may be formed between the amino acids at positions j and j+3 of the GIP analog according to the present invention, such as positions 17 and 20. In this embodiment, one of the amino acids at positions 17 and 20 is substituted with a negatively-charged amino acid, such as Glu, and the other is a positively-charged amino acid, such as Lys.

In an embodiment, a lactam bridge may be formed between the amino acids at positions j and j+3 of the GIP analog according to the present invention, such as positions 17 and 20. In this embodiment, one of the amino acids at positions 17 and 20 is substituted with a negatively-charged amino acid, such as Glu, and the other is a positively-charged amino acid, such as Lys.

In an embodiment, the GIP analog includes salt bridge(s) between the side chains of amino acids at position i and i+4 of the GIP analog according to the present invention, wherein i is 12, 13, 16, 17, 20, or 24.

In an embodiment, the GIP analog includes salt bridge(s) located at j and j+3 of the GIP analog according to the present invention, wherein j is 17, 18, 19, or 20.

In an embodiment, a fatty acid moiety is conjugated to epsilon-amine group of Lys present in the GIP analog according to the present invention, such as Lys$^{16}$ or Lys$^{28}$. The fatty acid may be selected from myristic acid, palmitic acid, stearic acid and cholic acid.

In an embodiment, a s-amine group (e.g., Lys, Orn, Dab, or Dap) is at position(s) 20, 24, 28, 32, 33, and/or 37 of the GIP analog according to the present invention. In an embodiment, the acyl group is covalently conjugated to the side chain of positively-charged amino acid residue at any position from position 30 to C-terminus.

In an embodiment, the epsilon-amine group of Lys at position 16 is acylated through fatty acid.

In an embodiment, the side chain of the positively-charged amino acid residue is acylated.

In an embodiment, the amino acid linked to the acyl is preferably located at position 40.

In an embodiment, a spacer is inserted between the peptide chain and fatty acid moiety. The spacer is a peptide comprising 1 to 10 amino acid residues, such as (Glu)m, m is an integer selected from 0 to 3.

In one embodiment, the spacer is an amino acid or a dipeptide selected from γ-Glu-γ-Glu, d-Ala-d-Ala, d-Ala-γ-Glu, γ-Glu-d-Ala, Glu-Glu.

In an embodiment, the acyl group is a C8 to C20 fatty acyl group, and highly preferable palmitoyl group.

In an embodiment, the GIP analog is covalently attached to a hydrophilic polymer at any amino acid position from 30 to C-terminus to significantly improve its pharmacokinetic properties. In an embodiment, the GIP analog is covalently attached to a hydrophilic polymer at amino acid position 24.

In an embodiment, the hydrophilic polymer is attached to the side chain of Cys, homocystein, Lys, Orn, Dab, Dap, or p-amine-phenylalanie of the GIP analog.

In an embodiment, the hydrophilic polymer is a polyethylene glycol (PEG).

In an embodiment, the PEG has a molecular weight of about 1,000 Daltons to about 40,000 Daltons, such as about 5,000 Daltons to about 40,000 Daltons, preferably about 1,000 Daltons to about 20,000 Daltons.

In an embodiment, the PEG has a functional group of maleimide or aldehyde.

In an embodiment, a spacer is inserted between the peptide chain and fatty acid moiety. The spacer is a peptide comprising 1 to 10 amino acid residues, such as (Glu)m, m is an integer selected from 0 to 3.

In one embodiment, the spacer is an amino acid or a dipeptide selected from γ-Glu-γ-Glu, d-Ala-d-Ala, d-Ala-γ-Glu, γ-Glu-d-Ala, Glu-Glu.

In an embodiment, the GIP analog is in the form of free carboxylic acid, amide or a pharmaceutically acceptable salt thereof.

In the aspect, the present invention provides a GIP analog which has GLP-1 agonist activity. The GIP analog according to the present invention has both GLP-1 agonist activity and GIPR stimulation activity.

In an embodiment, the present invention provides a GIP analog derived from GIP (1-29, SEQ ID NO: 1), wherein GIP analog has both GLP-1 agonist activity and GIPR stimulation activity, and comprises an amino acid sequence represented by the following formula I:

Tyr-A2-A3-Gly-Thr-Phe-A7-Ser-Asp-Tyr-Ser-A12-
A13-A14-A15-Lys-A17-A18-A19-A20-A21-
A22-A23-A24-Trp-Leu-A27-A28-A29-Y (SEQ ID NO. 103)

wherein

A2 is selected from the group consisting of Ala, Gly, Sarcosine, Aib, d-Ala and d-Ser;

A3 is selected from the group consisting of Glu and Gln;

A7 is selected from the group consisting of Thr, Ile and Ser;

A12 is selected from the group consisting of Ile, Glu and Asp;

A13 is selected from the group consisting of an amino acid residue having aryl group and is selected from Tyr, Phe, Phe(4-F), Phe(4-NO2), Phe(4-NH2), Ala, Ala(2-thienyl), Ala(benzothienyl), Ala(4-Pyridyl) and phenylglycine;

A14 is selected from the group consisting of Met or oxidized Met, Leu, Val, Norleucine and Ile;

A15 is selected from the group consisting of Glu and Asp;

A17 is selected from the group consisting of Ile, Glu, and Gln;

A18 is selected from the group consisting of Ala and His;

A19 is selected from the group consisting of Val, Ala, Leu, Gln and Ile;

A20 is selected from the group consisting of Arg, Lys-Z, Gln, Glu, Asp and Cys-Z;

A21 is selected from the group consisting of Glu, Asp and Leu;

A22 is selected from the group consisting of Phe, Phe(4-F), Phe(4-Cl), Tyr, Tyr(4-Me) and Nal;

A23 is selected from the group consisting of Ile and Val;

A24 is selected from the group consisting of Ala, Asn, Glu, Lys-Z and Cys-Z;

A27 is selected from the group consisting of Val, Leu, Ala, and Lys-Z;

A28 is selected from the group consisting of Lys-Z, Ala, Arg, and Asn;

A29 is selected from the group consisting of Gly, Gln and Arg;

Y is selected from the group consisting of: A30 and -Gly-Pro-Ser-Ser-Gly-Ala-Pro-Pro-Pro-Ser-A40 (SEQ ID NO. 104), or absent;

A30 and A40 are independently selected from the group consisting of -(Lys)n-Z and -Cys-Z, or absent;

Z is selected from the group consisting of -(Glu)m-PEG, -(Glu)m-biotin and -(Glu)m-fatty acid, or absent;

n is an integer selected from 1 to 6;

m is an integer selected from 0 to 3;

wherein, a lactam linkage is optionally formed between the amino acids at positions i and i+4 of the GIP analog; i is an integer selected from 12 to 24;

or a pharmaceutically acceptable salt thereof.

In an embodiment, the present invention provides a GIP analog as shown in formula I, wherein:

A3 is Glu;

A13 is selected from the group consisting of an amino acid residue having aryl group and is selected from Tyr, Phe, Phe(4-F), Phe(4-NO2), Phe(4-NH2), Ala(2-thienyl), Ala (benzothienyl) and phenylglycine;

A15 is Glu;

A18 is Ala;

A19 is selected from the group consisting of Val and Ala;

A20 is selected from the group consisting of Arg, Lys-Z, Glu, Asp and Cys-Z;

A21 is selected from the group consisting of Glu and Leu;

A22 is Phe;

A23 is Ile;

A27 is selected from the group consisting of Val and Lys-Z;

A28 is selected from the group consisting of Lys-Z and Asn; and

A29 is Gly;

Z is selected from the group consisting of -(Glu)m-PEG, -(Glu)m-biotin and -(Glu)m-fatty acid, or absent;

m is an integer selected from 0 to 3.

In this aspect, the present invention provides a GIP analog derived from GIP (1-29, SEQ ID NO: 1), wherein the GIP analog has both GLP-1 agonist activity and GIPR stimulation activity, and comprises an amino acid sequence represented by the following formula:

Tyr-A2-Glu-Gly-Thr-Phe-A7-Ser-Asp-Tyr-Ser-A12-
A13-A14-Glu-Lys-A17-Ala-A19-A20-A21-Phe-
Ile-A24-Trp-Leu-A27-A28-Gly-Y (SEQ ID NO. 105)

wherein

A2 is selected from the group consisting of Ala, Gly, Sarcosine, Aib, d-Ala and d-Ser;

A7 is selected from the group consisting of Thr, Ile and Ser;

A12 is selected from the group consisting of Ile, Glu and Asp;

A13 is selected from the group consisting of an amino acid residue having aryl group and is selected from Tyr, Phe, Phe(4-F), Phe(4-NO2), Phe(4-NH2), Ala(2-thienyl), Ala (benzothienyl) and phenylglycine.

A14 is selected from the group consisting of Met or oxidized Met, Leu, Val, Norleucine and Ile;

A17 is selected from the group consisting of Glu and Gln;

A19 is selected from the group consisting of Val and Ala;

A20 is selected from the group consisting of Arg, Lys-Z, Glu, Asp and Cys-Z;

A21 is selected from the group consisting of Glu and Leu;

A24 is selected from the group consisting of Ala, Asn, Glu, Lys-Z and Cys-Z;

A27 is selected from the group consisting of Val and Lys-Z;

A28 is selected from the group consisting of Lys-Z and Asn;

Y is selected from the group consisting of: A30 and Gly-Pro-Ser-Ser-Gly-Ala-Pro-Pro-Pro-Ser-A40 (SEQ ID NO. 104), or absent;

A30 and A40 are independently selected from the group consisting of (Lys)n-Z, and Cys-Z, or absent;

Z is selected from the group consisting of (Glu)m-PEG, (Glu)m-biotin and (Glu)m-fatty acid; or absent;

n is an integer selected from 1 to 6;

m is an integer selected from 0 to 3;

wherein, a lactam linkage is optionally formed between the amino acids at positions i and i+4 of the GIP analog, i is an integer selected from 12 to 24 or a pharmaceutically acceptable salt thereof.

In some embodiments, the present invention provides a GIP analog as shown in formula I, wherein:

Y is A30 or absent;

A30 is selected from the group consisting of (Lys)n-Z and Cys-Z, or absent;

Z is selected from the group consisting of (Glu)m-PEG, (Glu)m-biotin and (Glu)m-fatty acid; or absent;

n is an integer selected from 1 to 6;

m is an integer selected from 0 to 3.

In some embodiments, the present invention provides a GIP analog as shown in formula I, wherein:

Y is Gly-Pro-Ser-Ser-Gly-Ala-Pro-Pro-Pro-Ser-A (SEQ ID NO. 104);

A40 is selected from the group consisting of (Lys)n-Z, and Cys-Z, or absent;

Z is selected from the group consisting of (Glu)m-PEG, (Glu)m-biotin and (Glu)m-fatty acid; or absent;

n is an integer selected from 1 to 6;

m is an integer selected from 0 to 3.

In some embodiments, the present invention provides a GIP analog as shown in formula I, wherein:

Z is selected from the group consisting of (Glu)m-PEG, (Glu)m-biotin and (Glu)m-fatty acid; m is an integer selected from 0 to 3.

In some embodiments, the present invention provides a GIP analog as shown in formula I, wherein: Y is absent.

In these embodiments, the present invention provides a GIP analog derived from GIP (1-29, SEQ ID NO: 1), wherein the GIP analog has both GLP-1 agonist activity and GIPR stimulation activity, and comprises an amino acid sequence represented by the following formula:

Tyr-A2-Glu-Gly-Thr-Phe-A7-Ser-Asp-Tyr-Ser-A12-A13-A14-Glu-Lys-A17-Ala-A19-A20-A21-Phe-Ile-A24-Trp-Leu-A27-A28-Gly (SEQ ID NO. 106)

wherein

A2 is selected from the group consisting of Ala, Gly, Sarcosine, Aib, d-Ala and d-Ser;

A7 is selected from the group consisting of Thr, Ile and Ser;

A12 is selected from the group consisting of Ile, Glu and Asp;

A13 is selected from the group consisting of an amino acid residue having aryl group and is selected from Tyr, Phe, Phe(4-F), Phe(4-NO2), Phe(4-NH2), Ala(2-thienyl), Ala (benzothienyl) and phenylglycine.

A14 is selected from the group consisting of Met or oxidized Met, Leu, Val, Norleucine and Ile;

A17 is selected from the group consisting of Glu and Gln;

A19 is selected from the group consisting of Val and Ala;

A20 is selected from the group consisting of Arg, Lys-Z, Glu, Asp and Cys-Z;

A21 is selected from the group consisting of Glu and Leu;

A24 is selected from the group consisting of Ala, Asn, Glu, Lys-Z and Cys-Z;

A27 is selected from the group consisting of Val and Lys-Z;

A28 is selected from the group consisting of Lys-Z and Asn;

Z is selected from the group consisting of (Glu)m-PEG, (Glu)m-biotin and (Glu)m-fatty acid;

m is an integer selected from 0 to 3;

wherein, a lactam linkage is optionally formed between the amino acids at positions i and i+4 of the GIP analog, i is an integer selected from 12 to 24 or a pharmaceutically acceptable salt thereof.

In some embodiments, the present invention provides a GIP analog as shown in formula I, wherein: Y is Gly-Pro-Ser-Ser-Gly-Ala-Pro-Pro-Pro-Ser (SEQ ID NO. 107).

In these embodiments, the present invention provides a GIP analog derived from GIP (1-29, SEQ ID NO: 1), wherein the GIP analog has both GLP-1 agonist activity and GIPR stimulation activity, and comprises an amino acid sequence represented by the following formula:

Tyr-A2-Glu-Gly-Thr-Phe-A7-Ser-Asp-Tyr-Ser-A12-A13-A14-Glu-Lys-A17-Ala-A19-A20-A21-Phe-Ile-A24-Trp-Leu-A27-A28-Gly-Gly-Pro-Ser-Ser-Gly-Ala-Pro-Pro-Pro-Ser (SEQ ID NO. 108)

wherein

A2 is selected from the group consisting of Ala, Gly, Sarcosine, Aib, d-Ala and d-Ser;

A7 is selected from the group consisting of Thr, Ile and Ser;

A12 is selected from the group consisting of Ile, Glu and Asp;

A13 is selected from the group consisting of an amino acid residue having aryl group and is selected from Tyr, Phe, Phe(4-F), Phe(4-NO2), Phe(4-NH2), Ala(2-thienyl), Ala (benzothienyl) and phenylglycine.

A14 is selected from the group consisting of Met or oxidized Met, Leu, Val, Norleucine and Ile;

A17 is selected from the group consisting of Glu and Gln;

A19 is selected from the group consisting of Val and Ala;

A20 is selected from the group consisting of Arg, Lys-Z, Glu, Asp and Cys-Z;

A21 is selected from the group consisting of Glu and Leu;

A24 is selected from the group consisting of Ala, Asn, Glu, Lys-Z and Cys-Z;

A27 is selected from the group consisting of Val and Lys-Z;

A28 is selected from the group consisting of Lys-Z and Asn.

Z is selected from the group consisting of (Glu)m-PEG, (Glu)m-biotin and (Glu)m-fatty acid;

m is an integer selected from 0 to 3;

wherein, a lactam linkage is optionally formed between the amino acids at positions i and i+4 of the GIP analog, i is an integer selected from 12 to 24 or a pharmaceutically acceptable salt thereof.

In some embodiments, the present invention provides a GIP analog as shown in formula I, wherein: A7 is Thr In some embodiments, the present invention provides a GIP analog as shown in formula I, wherein: A2 is Aib.

In some embodiments, the present invention provides a GIP analog as shown in formula I, wherein: A13 is Tyr.

In some embodiments, the present invention provides a GIP analog as shown in formula I, wherein: A17 is Glu.

In some embodiments, the present invention provides a GIP analog as shown in formula I, wherein: A19 is Val.

In some embodiments, the present invention provides a GIP analog as shown in formula I, wherein: A20 is Arg.

In some embodiments, the present invention provides a GIP analog as shown in formula I, wherein: A24 is Cys-Z;

Z is -(Glu)m-PEG;

m is an integer selected from 0 to 3

In an embodiment, the present invention provides a GIP analog as shown in formula I, wherein:

A30 and A40 are independently (Lys)n-Z;

Z is selected from the group consisting of -(Glu)m-PEG, -(Glu)m-biotin and -(Glu)m-fatty acid, or absent;

n is an integer selected from 1 to 6;

m is an integer selected from 0 to 3.

In an embodiment, the present invention provides a GIP analog as shown in formula I, wherein:

Z is selected from the group consisting of -(Glu)m-PEG and -(Glu)m-fatty acid;

m is an integer selected from 0 to 2.

In an embodiment, the present invention provides a GIP analog as shown in formula I, wherein:

Z is -(Glu)m-PEG;

m is an integer selected from 0 to 2.

In an embodiment, the present invention provides a GIP analog as shown in formula I, wherein:

Z is selected from the group consisting of -(Glu)m-fatty acid;

m is an integer selected from 0 to 2.

For example, -(Glu)m- may be gamma-Glu or gamma-Glu-gamma-Glu.

In some embodiments, the present invention provides a GIP analog as shown in formula I, wherein: a lactam linkage is formed between the amino acids at positions i and i+4 of the GIP analog; i is an integer selected 12, 16 and 24.

In some embodiments, the fatty acid is selected from the group consisting of myristic acid, palmitic acid, stearic acid and cholic acid.

In some embodiments, the molecular weight of PEG is from 5 kDa to 40 kDa, such as 20 kDa, 30 kDa or 40 kDa.

In some embodiments, the GIP analog or a pharmaceutically acceptable salt thereof comprises an amino acid sequence selected from the group consisting of SEQ ID NOs: 65, 2 to 64 and 66 to 98.

In some embodiments, the GIP analog or a pharmaceutically acceptable salt thereof comprises an amino acid sequence selected from the group consisting of SEQ ID Nos. 3, 18, 19, 20, 21, 35, 45, 52, 63, 65, 72, 74, 80, 97 and 98.

In some embodiments, the GIP analog or a pharmaceutically acceptable salt thereof comprises an amino acid sequence selected from the group consisting of SEQ ID No. 52, 72 and 74, which sequence has at least one fatty acid moiety linked at position 20, 24 and/or C-terminal.

In some embodiments, the GIP analog or a pharmaceutically acceptable salt thereof comprises an amino acid sequence selected from the group consisting of SEQ ID No. 65, 74 and 98 which sequence has at least one PEG moiety linked at position 20, 24 and/or C-terminal.

In some embodiments, the GIP analog or a pharmaceutically acceptable salt thereof comprises the amino acid sequence of SEQ ID No. 74 with PEG moiety linked at position 24 and a fatty acid moiety linked at C-terminal.

The GIP analog according to the present invention can be synthesized and modified by methods known to the person skilled in the art. For example, the peptide backbone of the GIP analog according to the present invention may be prepared by standard solid-phase peptide synthesis (Fmoc Solid Phase Peptide Synthesis: A Practical Approach, Chan, Weng C.; White, Peter D., *OXFOR University press*, 2000, 41-72) or the method described in Examples 1 to 7 hereinafter. The GIP analog may also be prepared by recombinant DNA techniques, or any other methods of preparing peptides and fusion proteins.

In a further aspect, the invention provides a pharmaceutical composition comprising an effective amount of a GIP analog as defined herein and a pharmaceutically-acceptable diluent, carrier or excipient.

In an embodiment, the pharmaceutical composition may further comprises one or more anti-diabetes agents selected from insulins, biguanides, sulfonylurea, rosiglitazone or pioglitazone, alpha-glucosaccharase inhibitors, and aminodipeptidase IV inhibitors.

In an embodiment, the pharmaceutical composition may be formulated into injections or dried powders.

As used herein, 'pharmaceutical composition' means a therapeutically effective formulation according to the invention.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The pharmaceutical compositions of the invention will normally be administered by any parenteral route, in the form of a pharmaceutical composition comprising the active ingredients, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous injections which may contain other substances, for example, enough salts or glucose to make the injections isotonic with blood. The aqueous injections should be suitably buffered (preferably to a pH of from 3 to 9), if necessary. The preparation of suitable parenteral formulations under sterile conditions is readily accomplished by standard pharmaceutical techniques well-known to those skilled in the art.

Pharmaceutical compositions suitable for parenteral administration include aqueous and non-aqueous sterile injections which may contain anti-oxidants, buffers, bacteriostats and solutes which render the formulation isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use.

For oral and parenteral administration to human patients, the daily dosage level of the pharmaceutical compositions of the invention will usually be from 0.1 μg to 100 μg, such as 1 μg to 100 μg, 10 μg, 20 μg, 30 μg, 40 μg, 50 μg, 60 μg, 70 μg, 80 μg, 90 μg or 100 μg per adult per day administered in single or divided doses.

Thus, for example, the pharmaceutical compositions of the invention may contain from and may preferably contain 0.1 μg to 100 μg, such as 1 μg to 100 μg, 10 μg, 20 μg, 30 μg, 40 μg, 50 μg, 60 μg, 70 μg, 80 μg, 90 μg or 100 μg of active agent for administration singly or two or more at a time, as appropriate.

In one embodiment, the pharmaceutical compositions of the invention are administered at a dosage ranging from 0.1 μg to 100 μg, such as 1 μg to 100 μg, 10 μg, 20 μg, 30 μg, 40 μg, 50 μg, 60 μg, 70 μg, 80 μg, 90 μg or 100 μg and at a frequency, such as but not limited to once or twice per day.

In a further aspect, the present invention relates to the use of the GIP analog according to the present invention in the treatment or prevention of the metabolic diseases.

In a further aspect, the present invention relates to the method of the treatment or prevention of the metabolic diseases, comprising administering an effective amount of a GIP analog or the pharmaceutically acceptable salt thereof according to the present invention or the pharmaceutical composition according to the present invention to the subject in need thereof.

In the present invention, the metabolic diseases includes, but not limited to diabetes mellitus, obesity and osteoporosis.

In a further aspect, the present invention relates to a method for activating both GIP and GLP-1 receptors in vivo and/or in vitro, comprising contacting the GIP analog or the pharmaceutically acceptable salt thereof according to the present invention with GIP and GLP-1 receptors. The method may be performed in vivo or in vitro.

DETAILED DESCRIPTION

Definitions

Figure 1:
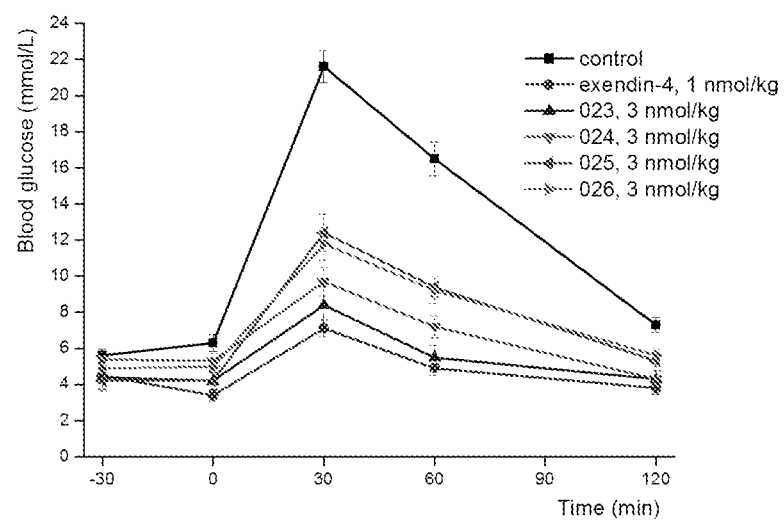
FIG. 1 represents a graph of ipGTT in normal ICR mice for the analogs 023, 024, 025, and 026 (at 3 nmol/kg), with exendin-4 (at 1 nmol/kg) as the reference compound. The compounds were administered through subcutaneous injection at the time point of −30 min, and glucose (3 g/kg) was loaded at the time point of 0 min, respectively.

In the present invention, such following terminology will be used in accordance with the definitions set forth below.

The term "similar" or "close" as used herein means greater or lesser than the value or range of values stated by 10%, but is not intended to designate any value or range of values to only this broader definition. Each value or range of values proceeded by the term "similar" or "close" is also intended to encompass the embodiment of the stated absolute value or range of values.

As used herein, the term "pharmaceutically acceptable carrier" includes any of the standard pharmaceutical carriers, such as phosphate buffered saline solution, water, emulsions such as an oil/water or water/oil emulsion, and various types of wetting agents.

As used herein, the term "pharmaceutically acceptable salt" refers to salts of compounds that maintain the biological activity of the parent compound, and which are not biologically or otherwise undesirable. Many of the compounds described herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, includes by way of example only, sodium, potassium, lithium, ammonium, calcium and magnesium salts. Salts derived from organic bases include, but not limited to, salts of primary, secondary and tertiary amines.

Pharmaceutically acceptable acid addition salts may be prepared from inorganic and organic acids. Salts derived from inorganic acids include hydrochloride acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicycli acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering blood glucose levels in the direction of normal levels and may include increasing or decreasing blood glucose levels depending on a given situation.

As used herein an "effective" amount or a "therapeutically effective amount" of a GIP analog refers to a nontoxic but sufficient amount of the peptide to provide the desired effect. For example, one desired effect would be the prevention or treatment of hyperglycemia, as measured by a reduction in blood glucose level. An alternative desired effect would include inducing body weight loss or preventing body weight gain, as measured by reduction in body weight. The amount that is "effective" will change from subject to subject, depending on the age and general condition of the individual, mode of administration, and the like. Thus, it is not always possible to specify an exact "effective amount." However, an appropriate "effective" amount in any individual case may be determined by one of ordinary skill in the art through routine experimentation.

As used herein, the term "purified" and like terms relates to the isolation of a molecule or compound in a form that is substantially free of contaminants normally associated with the molecule or compound in a native or natural environment. As used herein, the term "purified" does not require absolute purity; rather, it is intended as a relative definition. The term "purified peptides" is used herein to describe a peptide which has been separated from other compounds including, but not limited to nucleic acid molecules, lipids and carbohydrates.

The term "isolated" requires that referenced material be removed from its original environment. For example, a naturally-occurring polynucleotide present in a living animal is not isolated, but the same polynucleotide, separated from some or all of the coexisting materials in the natural system, is isolated.

As used herein, the term "peptides" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

A "GIP analog" as used herein includes any peptide comprising, either the amino acid sequence of SEQ ID NO: 18, or any analog of the amino acid sequence of SEQ ID NO: 18, including amino acid substitutions, additions, deletions or post-translational modifications (e.g., methylation, acylation, alkylation, ubiquitination, intramolecular covalent bonding such as lactam bridge formation, PEGylation, and the like) of the peptide, wherein the analog stimulates GIPR and GLP-1R activations, e.g., as measured by cAMP induction using the assay described in the example.

As used herein an amino acid "modification" refers to a substitution, addition or deletion of an amino acid, and includes substitution with or addition of any of the 20 naturally-occurring amino acids. Throughout the application, all references to a particular amino acid position number (e.g. position 24) refer to the amino acid at that position in native GIP (SEQ ID NO: 1) or the corresponding amino acid position in any analog thereof.

As used herein the term "native GLP-1" refers to a peptide comprising the sequence of human GLP-1 (7-36, or 7-37), and term "native GIP" refers to a peptide comprising the sequence of human GIP (1-42). As used herein, a general reference to "GLP-1" or "GIP" in the absence of any further designation is intended to mean native GLP-1 or native GIP, respectively.

As used herein an amino acid "substitution" refers to the replacement of one amino acid residue by a different amino acid residue.

As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 5,000 to 40,000 Daltons. "Polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "PEGylated" or like terms refers to a compound that has been modified from its native state by linking a PEG chain to the peptide. A "PEGylated peptide" is a peptide that has a PEG chain covalently attached to the peptide itself.

As used herein the term "fatty acid" refers to a carboxylic acid with a long aliphatic tail (chain), which is either saturated or unsaturated. In the present invention, the fatty acid is a carboxylic acid with a C4 to C30 linear or branched aliphatic group. The preferred fatty acid is selected from myristic acid, palmitic acid, and stearic acid.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the naturally-occurring amino acids.

As used herein a "spacer" is a bond, molecule or group of molecules that links two separate entities to one another. Spacers may provide for optimal spacing of the two entities or may further supply a labile linkage that allows the two entities to be separated from each other. Labile linkages include photo-cleavable groups, acid-labile moieties, base-labile moieties and enzyme-cleavable groups.

As used herein the term "charged amino acid" refers to an amino acid that comprises a side chain that is negatively charged (i.e., de-protonated) or positively charged (i.e., protonated) in aqueous solution at physiological pH value. For example, negatively charged amino acids include Asp, Glu, cysteic acid, homocysteic acid, and homoglutamic acid, whereas positively charged amino acids include Arg, Lys and His. Charged amino acids include the charged amino acids among the 20 naturally-occurring amino acids, as well as non-naturally occurring amino acids.

As used herein the term "acidic amino acid" refers to an amino acid that comprises a second acidic moiety, including for example, a carboxylic acid or sulfonic acid group.

As used herein, "GIP activity" of a peptide refers to the ratio of the $EC_{50}$ value of the peptide at GIPR divided by the $EC_{50}$ value of native GIP at GIPR.

As used herein, "GLP-1 activity" of a peptide refers to the ratio of the $EC_{50}$ value of the peptide at GLP-1R divided by the $EC_{50}$ value of native GLP-1 at GLP-1R.

As used herein, the term "alkyl" refers to a linear or branched hydrocarbon containing the indicated number of carbon atoms. Exemplary alkyls include methyl, ethyl, and normal propyl groups.

As used herein, the term "heteroalkyl" refers to a linear or branched hydrocarbon containing the indicated number of carbon atoms and at least one heteroatom in the backbone of the structure. Suitable heteroatoms for purpose herein include but not limited to N, S, and O.

As used herein, the term "cycloalkyl" refers to a cyclic hydrocarbon group containing the indicated number of carbon atoms, e.g. cyclopropyl, cyclobutyl, cyclohexyl, and cyclopentyl.

As used herein, the term "heterocyclic" refers to a cyclic hydrocarbon group containing the indicated number of carbon atoms and one to three heteroatoms independently selected from the group comprising O, N, and S. Non-limiting examples of heterocycloalkyl groups include piperidine, tetrahydrofuran, tetrahydropyran, dihydrofuran, morpholine, thiophene, and the like.

As used herein, the term "aryl" refers to a monocyclic or polycyclic aromatic group, preferable a monocyclic or bicyclic aromatic group, e.g., phenyl or naphthyl, containing the indicated number of carbon atoms. Unless otherwise indicated, an aryl group can be un-substituted or substituted.

As used herein, the term "Aib" refers to α-aminoisobutyric acid.

As used herein, the term Phe(4-F) refers to the analog of phenylalanine, which para-position of the phenyl group is substituted by fluorine.

As used herein, the term Phe(4-NO$_2$) refers to the analog of phenylalanine, which para-position of the phenyl group is substituted by nitro.

As used herein, the term Phe(4-NH$_2$) refers to the analog of phenylalanine, which para-position of the phenyl group is substituted by amine.

As used herein, the term Ala(2-thienyl) refers to the analog of alanine, which β-methyl is modified by 2-thienyl group.

As used herein, the term Ala(benzothienyl) refers to the analog of alanine, which β-methyl is modified by benzothienyl group.

As used herein, the term Nal refers to the analog of alanine, which β-methyl is modified by Naphthyl group.

As used herein, the term Ala(4-pyridyl) refers to the analog of alanine, which β-methyl is modified by 4-pyridyl group.

As used herein, the term Phenylglycine refers to the analog of glycine, which methylene is modified by phenyl group.

As used herein, the term Tyr(4-Me) refers to the analog of tyrosine, which the hydrogen of hydroxyl group is substituted by methyl group.

As used herein, the term Sarcosine refers to the analog of glycine, which amino group is modified by methyl group.

As used herein, the term "Orn" refers to 2,5-Diaminopentanoic acid.

As used herein, the term "Dab" refers to 2,4-Diaminobutyric acid.

As used herein, the term "Dap" refers to 2,3-Diaminopropionic acid

As used herein, the term "Norleucine" refers to 2-aminohexanoic acid.

Native GIP (1-42) does not activate GLP-1R at all (Moon, et al. Molecular Cells, 2010, 30, 149-154), not to speak of the fragment GIP (1-29). However, GIP (1-29) fragment could maintain the equivalent GIPR activation in vitro to that of the full-length GIP (1-42) in our research profile. So, novel GIP analogs based on the sequence of GIP (1-29) with site mutations through the concept of hybridization should be conceivable. The positive residues from GLP-1, exendin-4, and liraglutide can be incorporated to induce GLP-1 activity. These GIP analogs could have potent GIPR activation equivalent to or even better than that of native GIP, and also potent GLP-1R activation equivalent to or even better than that of native GLP-1 (7-36, or 7-37) in vitro.

Specific Site Mutations to Induce GLP-1 Activity.

The N-terminal sequences of GLP-1 and GIP were compared site by site, and Thr$^{13}$/Ile$^7$ should be the most distinguished substitutions besides His$^7$/Tyr$^1$. As recently reported, the N-terminal moiety of each peptide, especially the residue at position 7 (the primary sequence number of each peptide), was critical for ligand selectivity (Moon, et al. Molecular Cells, 2010, 30, 149-154). So, based on the sequence of GIP (1-29), Thr$^7$ was firstly incorporated to induce GLP-1R activation in our research profile. Furthermore, Tyr$^{13}$ and Glu$^{15}$ were then substituted to potentiate GLP-1 activity, and Aib$^2$ was also substituted to offer DPP-IV stability.

The obtained GIP analog (SEQ ID NO: 3) showed almost 0.2% of GLP-1R activation against native GLP-1 in CHO/hGLP-1R cell assay, much better than the initial scaffold (SEQ ID NO: 1); meanwhile it showed 77.7% of GIPR activation against native GIP in CHO/hGIPR cell assay, which indicated that GIPR could well tolerate the substitutions at these positions mentioned above. Although its potency in GLP-1R was quite low, further modifications to improve GLP-1R stimulation along with maintained GIP activity were worth exploring.

The second-round modifications were mainly focusing on positions 13 and 22 respectively based on the backbone of the analog 003. In the case of Tyr$^{13}$, the 4'-hydroxyl group was replaced with fluoro- (SEQ ID NO: 4) and nitro-groups (SEQ ID NOs: 5, 8, and 15); or Tyr$^{13}$ was replaced with Phe$^{13}$ (SEQ ID NO: 7 and 11) and phenyl glycine$^{13}$ (SEQ ID NO: 9). Meanwhile, in the case of Phe$^{22}$, Tyr (SEQ ID NO: 12), Tyr(4-Me) (SEQ ID NO: 13) and Phe(4-F) (SEQ ID NO: 14) were substituted at this position respectively. In the manual operation for the solid-phase peptide synthesis, oxidized-Met$^{14}$ was observed occasionally due to oxygen introduction (SEQ ID NOs: 4, 5, 6, and 7). The bioisostere of Met, norleucine, was subsequently adopted to avoid oxidization in manual processing (SEQ ID NOs: 8 to 13, 14, and 16 to 17). Unfortunately, all these modified analogs failed to exhibit effective GLP-1 activity in vitro when compared to the analog 003, and impaired GIP activity was even observed in some modified analogs.

The Glu-Ala-Glu and Glu-Ala-Gln substitutions at positions from 17 to 19 (SEQ ID NO: 16) did not induce more GLP-1 activity either (still less than 1% activation against native GLP-1). Additionally, the positive residues from liraglutide, Val$^{27}$Arg$^{28}$ substitutions (SEQ ID NO: 17) did increase GLP-1 activity to around 5% against native GLP-1; however, its GIP activity was reduced to only 21% against native GIP. Hence, new strategies should be explored to achieve satisfactory activities in vitro in both GLP-1R and GIPR, and more GLP-1 characteristic residues should be incorporated.

Further Modifications Through Incorporating GLP-1 Characteristic Moieties.

Positive residues from GLP-1 sequence and exendin-4 sequence in the middle portion and C-terminus were intentionally incorporated into our preferred backbone (SEQ ID NO: 3). The N-terminal region (1-16) should be highly preserved due to receptor recognition. The sequence alignments of the designed chimeric peptides (SEQ ID NOs: 18, 19, 20, and 21) were displayed in the following diagrammatic representations. For the purposes of this patent, subscript amino acid designations for GLP-1 were numbered according to the primary sequence of the processed peptide (i.e. GLP-1$_{[7-36]}$=GLP-1$_{[1-30]}$).

| 023: | SEQ ID NO: 3 [1-16] | Exendin-4 [17-20] | GLP-1 [21-29] |
|---|---|---|---|
| 024: | SEQ ID NO: 3 [1-16] | Exendin-4 [17-20] | Exendin-4 [21-29] |
| 025: | SEQ ID NO: 3 [1-16] | GLP-1 [17-20] | GLP-1 [21-29] |

-continued

026: | SEQ ID NO: 3 [1-16] | GLP-1 [17-20] | Exendin-4 [21-29] |

These four chimeric peptides were compared to the native ligands, GLP-1 and GIP, side by side in both CHO/hGLP-1R and CHO/hGIP-1R cell assays. The data in vitro were summarized in Table 1. Through further incorporating GLP-1 characteristic residues in the middle portion [17-20] and C-terminus [21-29], the GLP-1 activity was greatly enhanced, and even stronger than native GLP-1.

TABLE 1

| | GLP-1R | | | GIPR | | |
|---|---|---|---|---|---|---|
| Compounds | $EC_{50}$ (nM) | GLP-1 (nM) | Relative Potency (%) | $EC_{50}$ (nM) | GIP (nM) | Relative Potency (%) |
| 023 | 1.276 | 0.957 | 75 | 0.088 | 0.094 | 106.8 |
| 024 | 0.309 | 1.094 | 354 | 0.1 | 0.5 | 500 |
| 025 | 0.837 | 1.094 | 131 | 1.5 | 0.5 | 33.3 |
| 026 | 0.380 | 1.094 | 288 | 4.2 | 0.5 | 11.9 |

The analog 024 exhibited the highest activity in both GLP-1R (more than 300% activation against native GLP-1), and in GIPR (about 500% activation against native GIP). Although 025 and 026 showed better GLP-1 activity than native GLP-1 (131% and 288%, respectively), they exhibited weaker GIP activity than native GIP (only 33.3% and 11.9%, respectively). In summary, the analogs 023 and 024 exhibited well-balanced dual activations of both GLP-1R and GIPR in vitro, and GIP activity was more dominant than GLP-1 activity.

The simultaneous activations of both GLP-1R and GIPR in vitro greatly encouraged us to confirm their efficacies in vivo subsequently. The evaluation in vivo was primarily performed through intraperitoneal glucose tolerance test (ipGTT) in normal ICR mice. The analog 023 was firstly evaluated through ipGTT to explore suitable administration dose level, with exendin-4 as the positive control.

Exendin-4 exhibited pronounced hypoglycemic effect at the dose of 1 nmol/kg against glucose administration; however, the analog 023 showed much weaker blood glucose lowering effect than exendin-4 at the same dose level. The analog 023 exhibited almost the maximal hyperglycemic activity at the dose of 3 nmol/kg in the presence of glucose loading, and even higher doses (6 nmol/kg, and 9 nmol/kg) did not differentiate the efficacy at all. According to the AUC data, there should be no statistical differences between exendin-4 (1 nmol/kg) group and 023 (3 nmol/kg, 6 nmol/kg, and 9 nmol/kg) groups.

Figure 2:
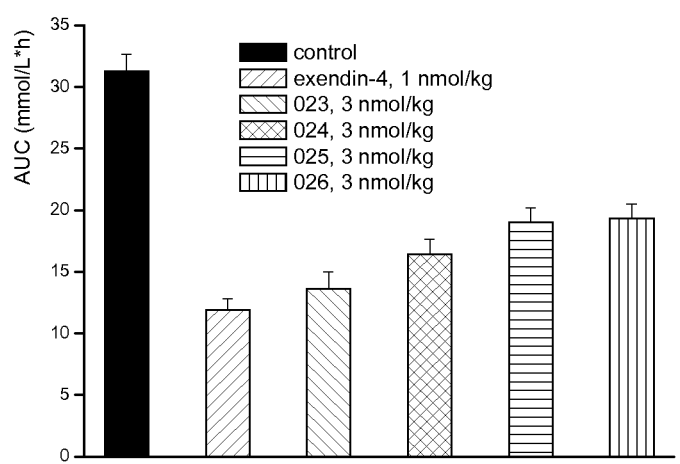
FIG. 2 represents a graph of AUC in the ipGTT for the analogs 023, 024, 025, and 026. Based on the AUC data, the analog 023 should be the most potent among these analogs, although the analog 024 showed better activities in vitro. The analog 023 was consequently selected as the hit compound.

Next, the analogs of 023, 024, 025, and 026 were evaluated side by side through ipGTT at the dose of 3 nmol/kg, also with exendin-4 as the reference (1 nmol/kg). Exendin-4 exhibited quite similar blood glucose lowering activity as that of in the preliminary test. Although all the GIP analogs showed significant hyperglycemic activity when compared to the control group, the analog 023 should be the most potent in vivo among all the analogs (see FIG. 1 and FIG. 2). Based on the observations, residues [17-20] from exendin-4 and residues [21-29] from GLP-1 should be the best substitution combinations to achieve dual agonisms in vitro and in vivo. The analog 023 was consequently selected as the hit compound in our research profile.

Further Modifications Through Fatty Acid Conjugation.

Inspired by the structure of liraglutide, fatty acid conjugation with the analog 023 was also adopted to potentiate the efficacies in vitro and in vivo particularly. Palmitoyl group was conjugated to the epsilon-amine group of Lys at the position 28 directly without any spacer (SEQ ID NO: 31). Unfortunately, the fatty acid conjugated analog 046 exhibited only 14.7% of GLP-1R activation against native GLP-1, and 8.5% of GIPR activation against native GIP. The much lower activity in vitro indicated that GLP-1R and GIPR could not tolerate fatty acid conjugation at position 28 in the sequence of the hit compound.

When the palmitoyl group conjugation site was altered to position 20, just like liraglutide, $Arg^{20}$ substitution in the hit compound sequence was intentionally replaced by $Lys^{20}$ (SEQ ID NO: 42). The fatty acid was also conjugated to the epsilon-amine group of $Lys^{20}$ directly without any spacer (SEQ ID NO: 51). The analog 067 showed quite similar in vitro profile as the analog 046, only 13.9% of GLP-1 activity against native GLP-1, and only 4.6% of GIP activity against native GIP. Based on the observations for the analogs 046 and 067, the strategy to improve dual actions in both GLP-1R and GIPR through fatty acid conjugation was temporarily neglected in our research profile.

Further Modifications Through Lactam Formation to Stabilize Alpha-Helical Configuration.

It has been demonstrated that the middle regions of native GLP-1 and GIP exhibiting alpha-helical configuration should be responsible for distinctive receptor bindings (Parthier, et al. Proceedings of the National Academy of Sciences, 2007, 104, 13942-13947; Underwood, et al. Journal of Biological Chemistry, 2010, 285, 723-730). The enhanced alpha-helical properties were believed to improve stabilities against neutral endopeptidase, and induce better efficacies as well (Murage, et al. Journal of Medicinal Chemistry, 2010, 53, 6412-6420).

Based on the sequence of the hit compound, the analog 023, lactam formation was intentionally introduced to constrain alpha-helical configuration in the middle portion (11-20) at the positions i and i+4. To accomplish the formation of lactam bridge, $Ile^{12}$ and $Arg^{20}$ were replaced by Glu respectively (SEQ ID NOs: 36 and 38). The side chains of amino acids at positions 12 and 16 were covalently linked to one another through amide bond with the help of coupling reagents (SEQ ID NO: 37). The lactam bridge between positions 16 and 20 was also constructed through the same synthetic procedure (SEQ ID NO:39).

These analogs were also evaluated in vitro through cAMP induction in both GLP-1R and GIPR. The preliminary data indicated that the lactam formation between positions 12 and 16 induced quite similar efficacies in vitro when compared to the hit compound (132.8% of GLP-1R activation against native GLP-1, and 146.8% of GIPR activation against native GIP). However, the lactam formed between positions 16 and 20 induced lower efficacies in both GLP-1R and GIPR when compared to the hit compound (only 37% of GLP-1 activity against native GLP-1, and only 35.4% of GIP activity against native GIP).

Further Modifications Through C-Terminal Extensions.

Based on the sequence of the hit compound (SEQ ID NO: 18), further modifications through C-terminal extensions were also investigated in our research profile. Five consecutive Lys at positions from 30 to 34 were firstly incorporated to achieve C-terminal extension (SEQ ID NO: 45). The additional introduction of positive-charged amino acids at C-terminus induced lower potencies in both GLP-1R and GIPR when compared to the hit compound (only 36.8% of GLP-1 activity against native GLP-1, and only 8.4% of GIP activity against native GIP).

The C-terminal residues of exendin-4 (30-39), GPSS-GAPPPS, designated CEX, were subsequently incorporated to the sequence of the hit compound to make the analog more GLP-1-like (SEQ ID NO: 35). To clarify the detailed sequence, the new hybrid GIP/GLP-1 peptide was displayed as the following diagrammatic representation.

051: | SEQ ID NO: 3[1-16] | Ex-4[17-20] | GLP-1[21-29] | Ex-4[30-39] |

Figure 3:
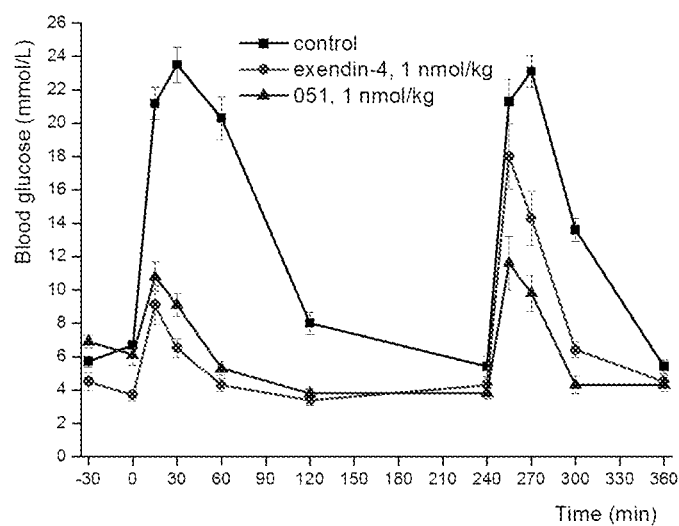
FIG. 3 represents a graph of ipGTT in normal ICR mice for the analog 051 (at 1 nmol/kg), with exendin-4 at the same dose level as the reference compound. The compounds were administered through subcutaneous injection at the time point of −30 min, and glucose (3 g/kg) was loaded at the time points of 0 min and 240 min respectively.
Figure 4:
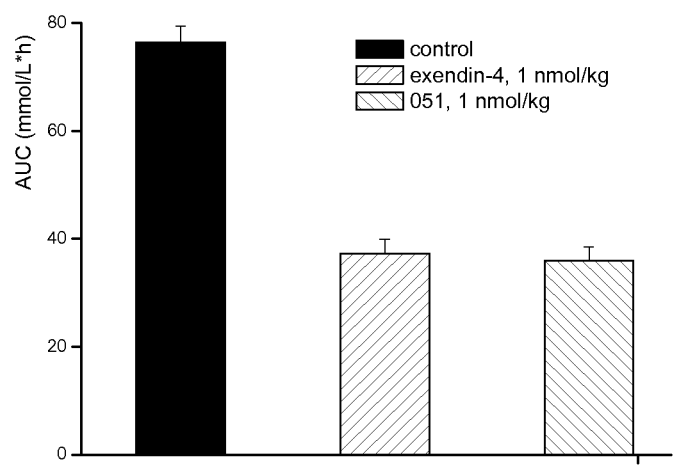
FIG. 4 represents a graph of AUC in the ipGTT for the analog 051. Based on the AUC data, the analog 051 exhibited quite similar blood glucose lowering effect as exendin-4 at the same dose level during two consecutive glucose loadings.

Although the analog 051 exhibited quite similar efficacies in vitro when compared to the hit compound (159.8% of GLP-1R activation against native GLP-1, and 89.5% of GIPR activation against native GIP), GLP-1 activity was more dominant than GIP activity.
The analog 051 was also evaluated in vivo through ipGTT in normal ICR mice, with exendin-4 as the reference compound. At the same dose level of 1 nmol/kg, both exendin-4 and the analog 051 exhibited pronounced but similar blood glucose lowering effect in the first glucose administration. When the second glucose challenge was loaded three hours later, the analog 051 showed much better hypoglycemic action than exendin-4 (see FIG. 3 and FIG. 4). Apparently, C-terminal extension through CEX incorporation could enhance efficacies in vivo particularly. The analog 051 was consequently selected as the lead compound in our research profile due to its high potency in vivo.
Hydrophilic Moieties Conjugation with the Lead Compound.

Hydrophilic moieties were generally conjugated with active proteins to achieve prolonged circulation rate with improved solubility. Polyethylene glycol (PEG) was the well-known hydrophilic moiety, and was applied widely in pharmaceutical field consequently. PEG was then adopted to conjugate with the lead compound, the analog 051 in our research profile. The Michael addition between the maleimide group and free thiol was the basic reaction to achieve PEG conjugation. The thiol was modified with maleimide-activated PEG to offer a PEGylated peptide comprising thioether formation shown below.

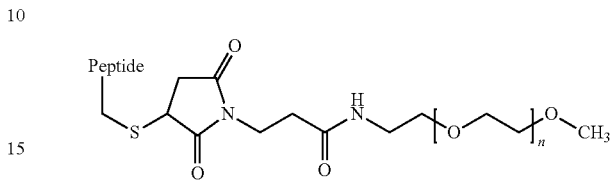

In our research profile, two maleimide-activated PEG moieties with molecular weights of about 20,000 and 40,000 Daltons were adopted for peptide PEGylation respectively. Additionally, one Cys substitution at the position 40 was intentionally introduced to offer the free thiol group. To clarify the detailed sequence, the PEGylated peptides were displayed as the following diagrammatic representation.

088: | SEQ ID NO: 3[1-16] | Ex-4[17-20] | GLP-1[21-29] | Ex-4[30-39] | Cys$^{40}$

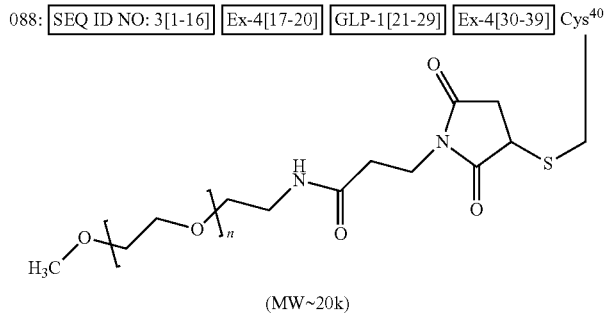

(MW~20k)

089: | SEQ ID NO: 3[1-16] | Ex-4[17-20] | GLP-1[21-29] | Ex-4[30-39] | Cys$^{40}$

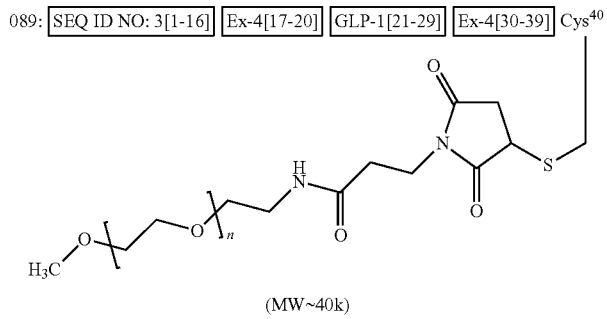

(MW~40k)

Figure 5:
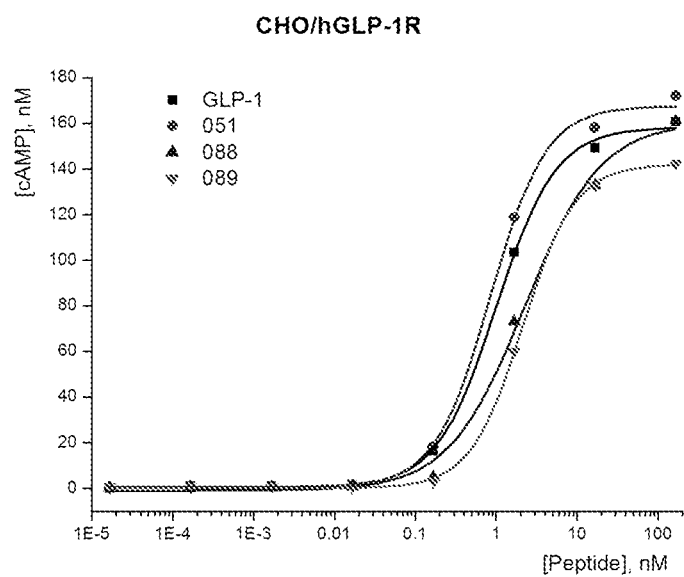
FIG. 5 represents a graph of hGLP-1R-mediated cAMP induction assay in CHO cell line for the analogs 088 and 089. The analog 088 (20 k PEGylated peptide) showed close GLP-1 activity to the analog 089 (40 k PEGylated peptide).
Figure 6:
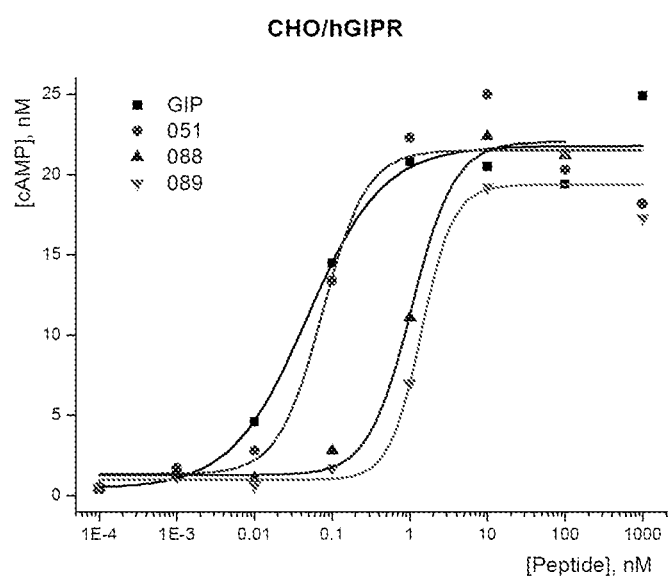
FIG. 6 represents a graph of hGIPR-mediated cAMP induction assay in CHO cell line for the analogs 088 and 089. The analog 088 (20 k PEGylated peptide) showed close GIP activity to the analog 089 (40 k PEGylated peptide).
Figure 7:
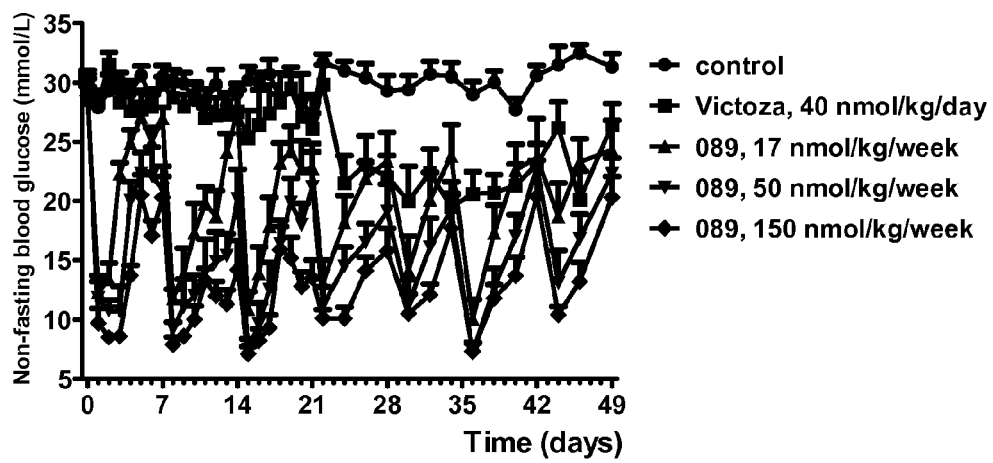
FIG. 7 represents a graph of non-fasting blood glucose levels for the analog 089 with dose titration in db/db mice from day 0 to day 49, with liraglutide as the reference compound. More glucose reduction was observed in all the groups of the analog 089 than that of liraglutide.
Figure 8:
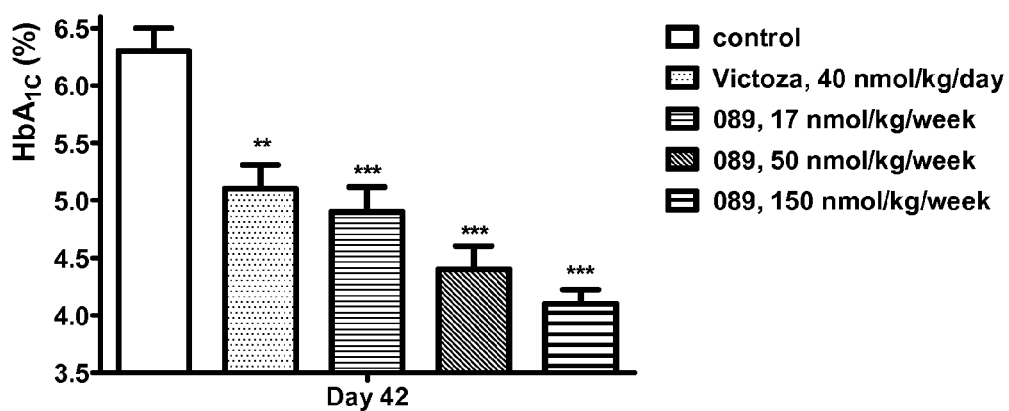
FIG. 8 represents a graph of $HbA_{1C}$ levels for the analog 089 with dose titration in dbldb mice on day 42, with liraglutide as the reference compound. More $HbA_{1C}$ reduction was observed in all the groups of the analog 089 than that of liraglutide.
Figure 9:
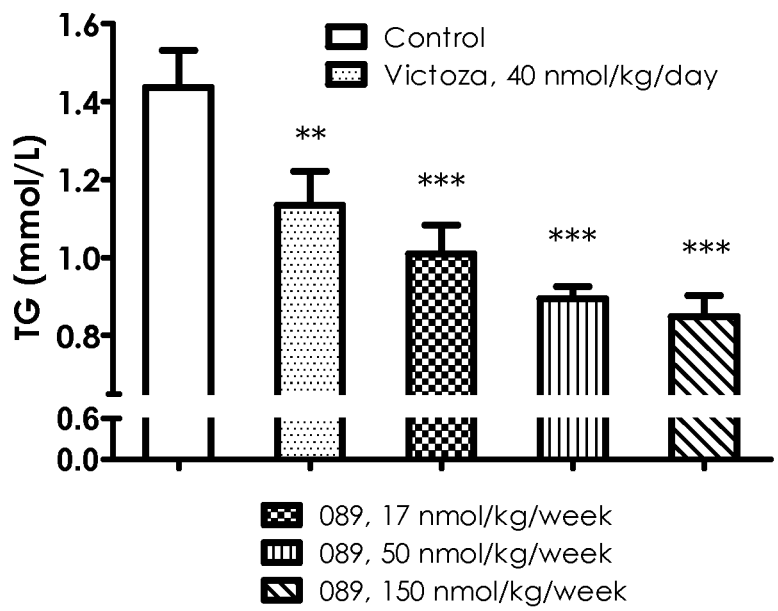
FIG. 9 represents a graph of serum TG levels for the analog 089 with dose titration in db/db mice on day 50, with liraglutide as the reference compound. More serum TG reduction was observed in all the groups of the analog 089 than that of liraglutide.
Figure 10:
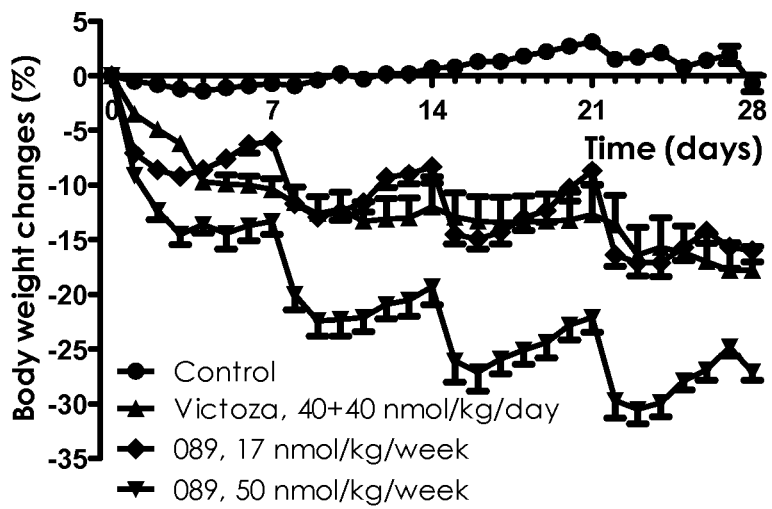
FIG. 10 represents a graph of body weight levels for the analog 089 with dose titration in DIO mice from day 0 to day 28, with liraglutide as the reference compound. More body weight reduction was observed in all the groups of the analog 089 than that of liraglutide.
Figure 11:
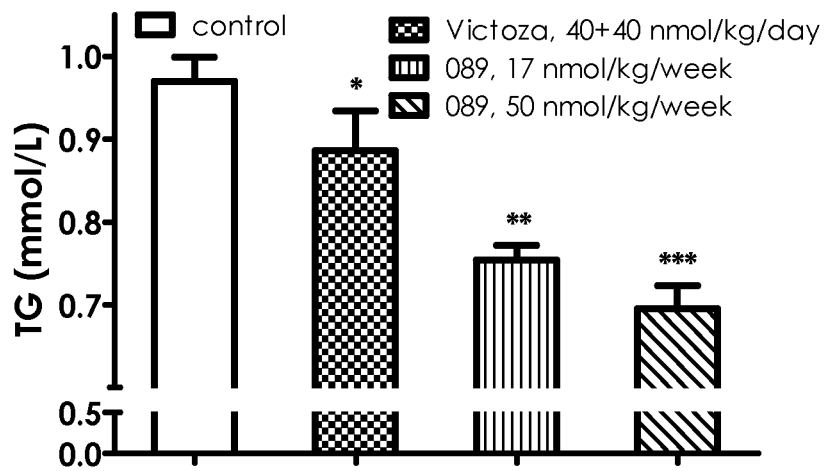
FIG. 11 represents a graph of serum TG levels for the analog 089 with dose titration in DIO mice on day 28, with liraglutide as the reference compound. More serum TG reduction was observed in all the groups of the analog 089 than that of liraglutide.
Figure 12:
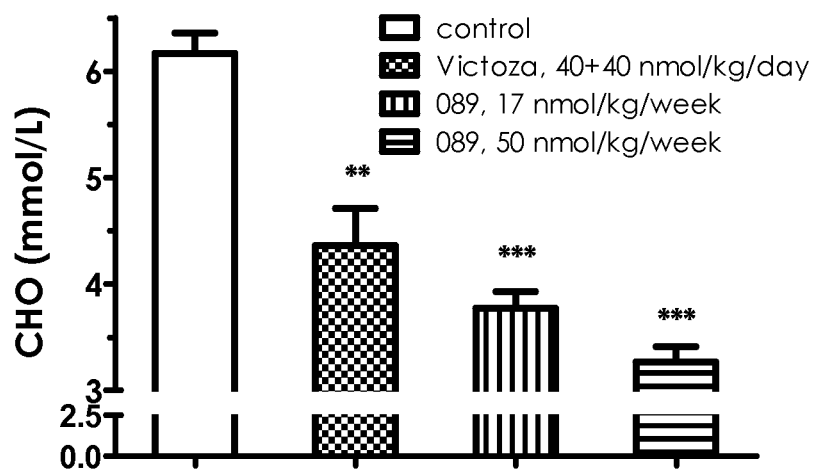
FIG. 12 represents a graph of serum CHO levels for the analog 089 with dose titration in DIO mice on day 28, with liraglutide as the reference compound. More serum CHO reduction was observed in all the groups of the analog 089 than that of liraglutide.
Figure 13:
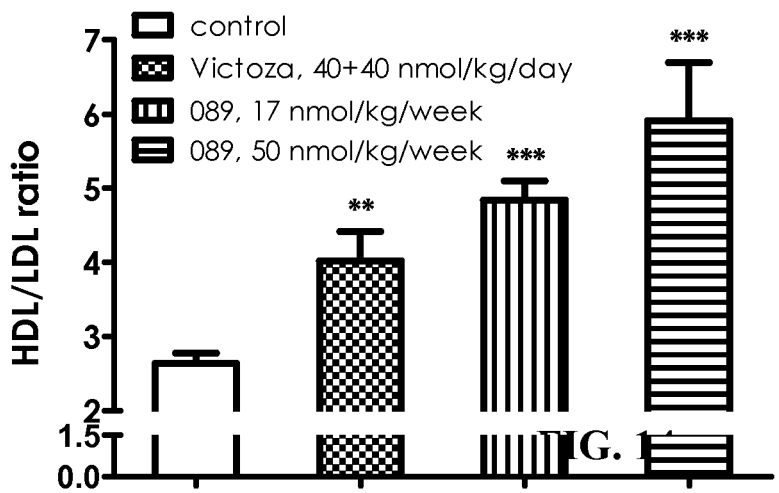
FIG. 13 represents a graph of serum HDL/LDL levels for the analog 089 with dose titration in DIO mice on day 28, with liraglutide as the reference compound. More improved HDL/LDL ratio was observed in all the groups of the analog 089 than that of liraglutide.
Figure 14:
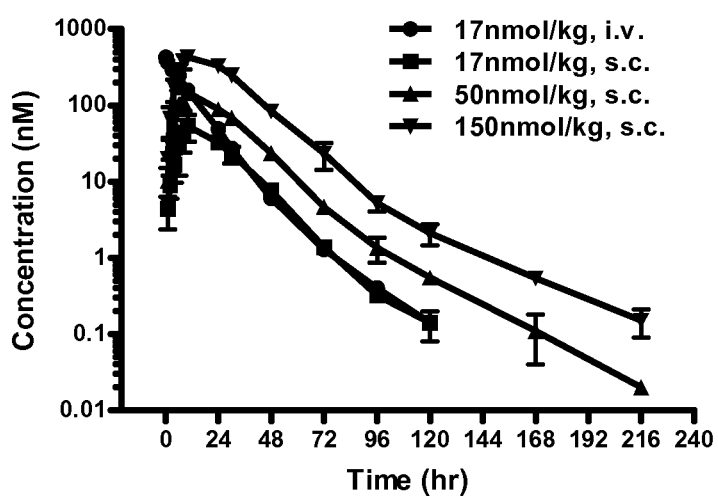
FIG. 14 represents a graph of pharmacokinetics study of the analog 089 in normal mice. The analog 089 showed a half life of 15 hrs by intravenous administration at 17 nmol/kg, and 11.9, 19.9, and 25.2 hrs at the doses of 17, 50 and 150 nmol/kg by subcutaneous administration, respectively. The bioavailability was about 30%.

(MW~40 k)
The analogs 088 and 089 were tested in vitro through cAMP induction in both GLP-1R and GIPR. These two PEGylated peptides both exhibited lower activations in GLP-1R, and GIPR in particular when compared to the lead compound. The analog 088 showed only 11% of GLP-1 activity against native GLP-1, and only 4.9% of GIP activity; meanwhile the analog 089 exhibited only 18.3% of GLP-1R activation against native GLP-1, and only 3.4% of GIPR activation against native GIP (see FIG. 5 and FIG. 6). The impaired efficacies in vitro indicated that both GLP-1R and GIPR in particular should be very sensitive to the ligand PEGylation.

The analogs 088 and 089 were evaluated in vivo as well in normal ICR mice to investigate their efficacies in blood glucose reduction and body weight loss. PEG conjugation definitely prolonged pharmaco-kinetic profile in vivo. The two compounds were administered through subcutaneous injection at the dose level of 40 nmol/kg on day 0 and day 3, respectively. The analogs 088 and 089 induced quite similar blood glucose lowering effect to one another, when compared to the control group; meanwhile, the analog 089 offered more body weight loss than the analog 088, especially after the second administration.

Further Modifications Through C-Terminal Extension and Fatty Acid Conjugation Based on the Lead Compound.

The analog 051 was further extended at C-terminus with positive-charged amino acid, such as Lys. The analog 066 was obtained when only one Lys substitution at the position 40 was introduced based on the sequence of the analog 051. The C-terminal introduction of six consecutive Lys offered the analog 071. Both the analog 066 and 071 were evaluated in vitro through cAMP induction in GLP-1R and GIPR. Unfortunately, C-terminal extension through positive-charged amino acid incorporation did not induce better efficacies in vitro when compared to the lead compound, the analog 051. The analog 066 showed only 43.7% of GLP-1 activity against native GLP-1, and only 50% of GIP activity against native GIP; meanwhile, the analog 071 exhibited only 25.1% of GLP-1R activation against native GLP-1, and only 22.1% of GIPR activation against native GIP. It appeared that longer C-terminal tail would induce lower efficacy in vitro.

Based on the sequence of the lead compound, the analog 051, lactam formation was also explored to stabilize the alpha-helical configuration at positions i and i+4. The analog 081 was obtained through lactam formation between positions 12 and 16, when $Ile^{12}$ was intentionally replaced by $Glu^{12}$. Similarly, the analog 085 was offered through lactam formation between positions 20 and 24, when $Arg^{20}$ and $Ala^{24}$ were replaced by $Lys^{20}$ and $Glu^{24}$, respectively. The analog 081 exhibited quite close efficacies in vitro to the analog 052-2 (124% of GLP-1 activity against native GLP-1, and 250% of GIP activity against native GIP). It also appeared that the lactam formation between positions 12 and 16 would be preferable to maintain satisfactory efficacies in vitro.

Fatty acid conjugation was re-considered to potentiate the efficacies of the lead compound, the analog 051. Based on the sequence of the analogs 066 and 071, palmitoyl group was conjugated to the epsilon-amine of C-terminal Lys ($Lys^{40}$ and $Lys^{44}$, respectively) to offer the analog 068 and 078 respectively. To clarify the detailed sequence, the new hybrid GIP/GLP-1 peptides were displayed as the following diagrammatic representations.

Unlike fatty acid conjugation to the analog 023, both the analogs 068 and 078 exhibited much better efficacies in vitro, especially in GLP-1R activation. The analog 068 showed 566% of GLP-1 activity against native GLP-1, and 319% of GIP activity against native GIP; meanwhile, the analog 078 showed 754% of GLP-1R activation against native GLP-1, and 352% of GIPR activation against native GIP. Obviously, GLP-1 activity was more dominant than GIP activity. Fatty acid conjugation to the lead compound, the analog 051, resulted in enhanced efficacies in vitro when compared to the free peptides.

The analog 068 was also compared to liraglutide side by side in vitro. The positive efficacies in both GLP-1R and GIPR of the analog 068 were confirmed; meanwhile, liraglutide was less potent than the analog 068 in GLP-1R, although it exhibited stronger GLP-1R activation than native GLP-1 at the same time. As previously expected, liraglutide did not stimulate GIPR at all, even at the concentration level of 1 µM. All these observations in vitro demonstrated that simultaneous stimulation of GLP-1R and GIPR was particularly advantageous for inducing better efficacies when compared to any single GLP-1R agonist.

With high efficacies in vitro, the analog 068 and 078 were subsequently evaluated in vivo through ipGTT in normal ICR mice, with liraglutide as the reference compound. At the dose level of 40 nmol/kg, the analog 068 induced more blood glucose reduction against glucose challenge than liraglutide, especially during the second glucose loading 5 hours later. Although the analog 078 exhibited quite similar hypoglycemic effect as the analog 068 during the first glucose administration, much weaker efficacy was observed when the second glucose challenge was loaded. It appeared that longer C-terminal tail did not potentiate the efficacies in vivo. The analog 068 was consequently selected as the candidate compound in our research profile due to its excellent profiles in vitro and in vivo.

Further Modifications Through Spacer Insertion Based on the Candidate Compound.

The spacer of gamma-Glu was also exploited to insert between the peptide chain and fatty acid moiety, like the profile of liraglutide. As the construction of liraglutide, the gamma-carboxylic group of the spacer was firstly coupled to the epsilon-amine of Lys at position 40, and the alpha-amine group of the spacer was then acylated by the palmitic acid. So, the alpha-carboxylic group of the spacer was maintained free finally. The spacer was also further extended through the introduction of one more gamma-Glu. To clarify the detailed sequence, the fatty acid conjugated analogs with gamma-Glu as the spacer were displayed as the following diagrammatic representations.

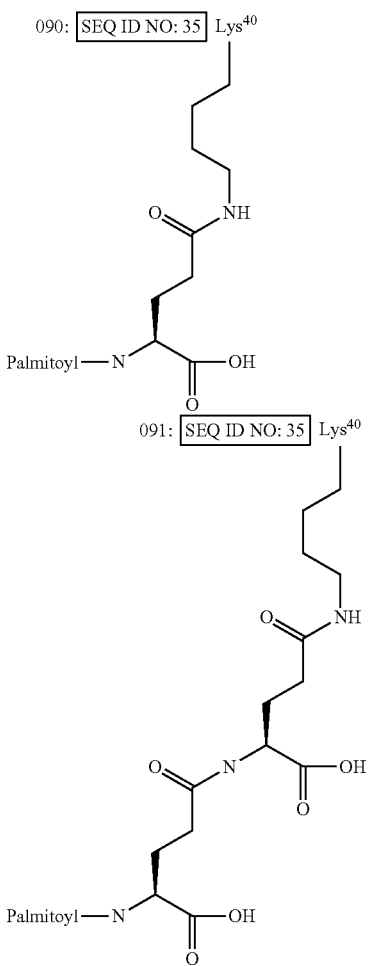

Although both the analogs 090 and 091 exhibited high potency in vitro, no significant difference between these two analogs was observed. The analog 090 showed 568% of GLP-1 activity against native GLP-1, and 1311% of GIP activity against native GIP; meanwhile, the analog 091 exhibited 921% of GLP-1R activation against native GLP-1, and 287% of GIPR activation against native GIP. When compared to the candidate compound, the analog 068, their difference was not prominent either.

The analogs 090 and 091 were subsequently evaluated in vivo through ipGTT in normal ICR mice with the analog 068 as the reference compound. At the dose level of 40 nmol/kg, all these three analogs exhibited pronounced but similar blood glucose lowering effect during two consecutive glucose administrations. The similar efficacies in vitro and in vivo indicated that the introduction of the spacer could not offer any advantage in the present profile.

When the $Arg^{20}$ substitution in the sequence of the analog 051 was replaced by Lys, palmitic acid was conjugated to the epsilon-amine group of $Lys^{20}$ with gamma-Glu and gamma-Glu-gamma-Glu as the spacers to offer the analogs 092 and 093, respectively. The palmitoyl group was conjugated to the epsilon-amine group of $Lys^{28}$ in the sequence of the analog 051 with gamma-Glu as the spacer to produce the analog 094. When compared to the structures of the analog 090 and 091, the fatty acid moieties were positioned to the central regions, instead of C-terminus, of our preferred sequence.

All these three analogs were tested in vitro through cAMP induction in both GLP-1R and GIPR. Although these three analogs showed quite similar and stronger GLP-1 activity against native GLP-1, they were much less potent than the analogs 090 and 091. The potencies in GLP-1R were reduced around 10 folds. In GIPR assay, quite similar situation was also observed, much less potency in GIPR activation than native GIP and the analogs 090 and 091, except the analog 093. The analog 093 showed almost the same GIPR activation as native GIP.

Hydrophilic Moieties Conjugation to the Candidate Compound.

Hydrophilic PEG moiety conjugation was also exploited to achieve prolonged pharmacokinetic profile in vivo. Michael addition reaction between maleimide group and free thiol was performed to accomplish the conjugation between the candidate compound and PEG moiety. Based on the sequence of the candidate compound, the analog 068, Ala substitution at position 24 was replaced by Cys to offer the free thiol group in the side chain. The analog 096 was subsequently obtained. Maleimide-activated PEG reagent (40 k version) was readily reacted to the thiol in the presence of slightly basic buffer. To clarify the detailed sequence, the $Cys^{24}$ substituted analog and PEG conjugated analog were displayed as the following diagrammatic representations.

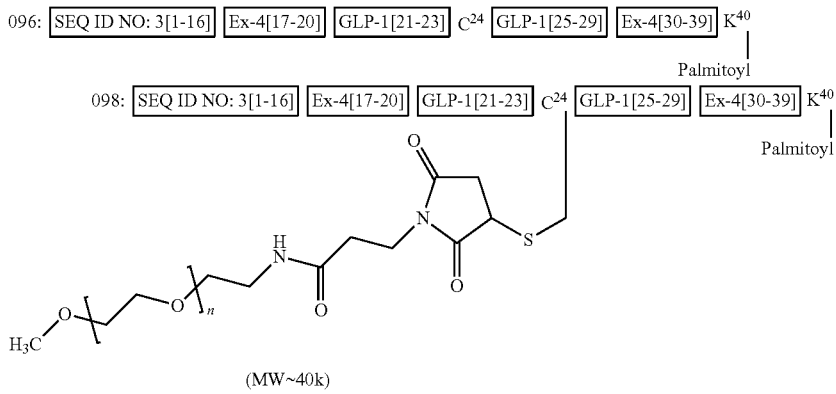

(MW~40k)

MW~40 k

The analogs 096 and 098 were evaluated in vitro through cAMP induction in both GLP-1R and GIPR. Generally speaking, the analogs 096 and 098 showed quite close but stronger GLP-1R activations than native GLP-1 (404.7% of GLP-1 activity against native GLP-1, and 463.3% of GLP-1 activity against native GLP-1 respectively), however they were slightly less potent than the candidate compound. The analog 096 showed only 42% of GIPR activation against native GIP; meanwhile the analog 098 exhibited 150% of GIPR activation against native GIP, almost as potent as the candidate compound. The preliminary activity in vitro indicated that $Cys^{24}$ substitution induced slightly lower but acceptable potencies in the both receptors, and PEG conjugation at the position 24 could maintain high potencies in vitro, especially in GIPR activation.

Anti-Diabetic Evaluation for the Candidate Compound in Db/Db Mice.

The candidate compound, the analog 068, was further evaluated in dbldb mice to examine its anti-diabetic properties, with liraglutide as the reference compound. The analog 068 and liraglutide were both administered through subcutaneous injection once daily.

Non-fasting glucose level was measured on day 0, day 14, and day 28, respectively. On day 0, the reduced blood glucose levels were observed in both liraglutide and the analog 068 groups. However, the analog 068 induced more blood glucose reduction than liraglutide even in the lower dose group, especially at 24 hours after the first injection. The dose-dependent manner of the analog 068 was not remarkable. On day 14, the initial blood glucose levels have been differentiated significantly after two-week therapy. Higher efficacies were observed in the groups of the analog 068 than that of liraglutide, although there was no statistical significance between the medium and high dose groups of the analog 068. On day 28, lower blood glucose levels were maintained in the groups of the analog 068 than that of liraglutide. The combined data (on day 0, 14, and 28) were compared side by side to establish the anti-diabetic profile for the analog 068.

The body weight and average cumulative food intake situations were also recorded during the first-week observation. When compared to the control group, the analog 068 induced more body weight loss than liraglutide even at the lower dose level, and perfect dose-dependency for the analog 068 was also observed. More food intake inhibitory effect was examined in the groups of the analog 068 than that of liraglutide. Apparently, the effect of body weight loss was correlated with the reduced food intake.

On day 8, blood lipid parameters were subsequently measured. Interestingly, the analog 068 induced more triglyceride reduction than liraglutide, especially in the lower dose group of the analog 068. As for the cholesterol level, the analog 068 induced similar cholesterol reduction as liraglutide, when compared to the control group. On day 21, high-density lipoprotein (HDL) cholesterol and low-density lipoprotein (LDL) cholesterol levels were also measured in all the groups. Neither the analog 068 nor liraglutide modified HDL cholesterol level when compared to the control group, although the high dose group of the analog 068 slightly raised HDL cholesterol level. Furthermore, the analog 068 induced more LDL cholesterol reduction than liraglutide, when compared to the control group.

On day 21, all the groups were challenged by exogenous insulin administration. That was the insulin tolerance test (ITT). The situation of insulin resistance in the control group was still maintained, and no blood glucose level reduction was observed in the control group. However, more blood glucose lowering effect against insulin challenge was examined in the analog 068 than that of liraglutide. Apparently, the situation of insulin resistance in the groups of the analog 068 was much more improved.

On day 35, ipGTT was additionally performed to evaluate the efficacies of the analog 068 and liraglutide. The analog 068 induced more blood glucose lowering activity against exogenous glucose challenge than liraglutide, except the low dose group.

Further evaluation for the analog 068 in dbldb mice demonstrated the obvious advantages of dual GLP-1R and GIPR agonists.

In vivo efficacy study for the analog 089 in dbldb mice and DIO mice was also investigated accordingly (see FIG. 7 to FIG. 13). Obviously, the analog 089 showed more advantages than the analog 068, because PEG conjugation offered once a week administration profile. PK studies for analog 089 in mice, rats, and monkeys were performed through antibody-based ELISA. Please check the sections of brief description of the drawings & examples for detailed information.

Any of the modifications of GIP analogs described in the present invention which maintain or increase GIP receptor activity, along with GLP-1 receptor activation (equivalent or even better than native GLP-1), increase stability, or reduce degradation can be applied individually or in combination. In some examples, the GIP analogs are soluble at a concentration of at least 2 mg/mL in water or PBS, and maintain at least 92% of the original peptide after 24 hours at 4° C. (pH=7.4).

Sterile pharmaceutical compositions comprising a pharmaceutical acceptable carrier or diluents and kits comprising devices are provided. Methods of inducing body weight loss or preventing body weight gain, comprising administering to a subject in need thereof such pharmaceutical compositions in an amount effective to induce body weight loss or prevent body weight gain are provided. Methods of treating diabetes, comprising administering to a subject in need thereof such pharmaceutical compositions in an amount effective to induce blood glucose reduction are provided.

All therapeutic methods, pharmaceutical compositions, kits and other similar examples described in the present invention contemplate that the use of the terms peptides, agonists, dual agonists, or analogs includes all pharmaceutically acceptable salts or esters thereof.

The present summary is not intended to define every aspect of the invention, and additional examples are described in other sections, such as the Detailed Description. The entire document is intended to be related as a unified disclosure, and it should be understood that all possible combinations of features described herein may be contemplated, even if the combination of features are not found together in the same sentence, or paragraph, or section of this invention.

EXAMPLES

The GIP analogs in the present invention may be prepared through standard solid-phase peptide synthesis, recombinant DNA techniques, or any other methods of preparing peptides and fusion proteins. Although certain non-naturally occurring amino acids can't be expressed by standard recombinant DNA techniques, techniques for their preparation are available so far. GIP analogs in the present invention that encompass non-peptide portions may be synthesized through standard organic chemistry reactions, in addition to standard peptide synthesis when necessary.

Example 1

General Protocol for Linear Peptide Synthesis

Peptides were produced by standard solid-phase peptide synthesis using the N-terminal Fmoc-protection strategy. Chain assembly was performed by manual synthesis according to standard Fmoc protocols. Fmoc Rink-Amide resin (1% DVB, 100~200 mesh, substitution at 0.34~0.44 mmol/g) from Tianjin Nankai Hecheng Sci. & Tech Co Ltd was exploited as the solid support. The following side-chain protected amino acids from Shanghai GL Biochem were used: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Glu(OAll)-OH, Fmoc-Gly-OH, Fmoc-Gly(Allyl)-OH, Fmoc-His(Trt)-OH, Fmoc-Ile-OH, Fmoc-Leu-OH, Fmoc-Lys(Boc)-OH, Fmoc-Lys(Alloc)-OH, Fmoc-Met-OH, Fmoc-Nle-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Boc-Tyr(tBu)-OH, Fmoc-Val-OH, Fmoc-Aib-OH. All chemicals (from various suppliers including Sigma Aldrich, J&K Scientific Ltd, Shanghai GL Biochem) were synthesis grade.

After synthesis, peptides were cleaved from the solid polymeric support and side chains were fully deprotected. This was achieved by the treatment of trifluoroacetic acid (TFA) in 2 hours, with containing 2.5% water and 2.5% 1,2-dimercaptoethane (EDT) to scavenge side-chain protecting groups. Peptide-TFA solutions were filtered from the resins and peptide was precipitated with chilled diethyl ether after TFA mainly removed. Peptides were isolated by centrifugation, washed with diethyl ether and dissolved in acetonitrile buffer.

Following cleavage from the resin, crude peptide extracts were analyzed by analytical reverse-phase HPLC. Analytical separations were conducted in 0.1% TFA with an acetonitrile gradient on a Waters Xterra@ MS system (1 mL/min, 214 nm, A buffer=0.1% TFA, B buffer=0.1% TFA/90% acetonitrile, gradient of 10% to 90% over 15 min) by using C18 column (50×2.1 mm) After analytical analysis, the crude extract was purified by semi-preparative chromatography in 0.1% TFA with an acetonitrile gradient on a Vydac C4 or C8 column (2.2×25 cm). Pure stuff was characterized by LC-MS, and then lyophilized to offer the target peptide.

Example 2

Synthesis of Aib$^2$-GIP(1-29)-Cys$^{30}$ and Similar MonoCys-Substituted Analogs 0.05 mmol Fmoc-Rink amide resin in a 10 mL reaction vessel, and standard Fmoc-chemistry solid-phase peptide synthesis procedures were performed through the following sequence, with DIC/HOBt as the coupling reagents.

Tyr-Aib-Glu-Gly-Thr-Phe-Ile-Ser-Asp-Tyr-Ser-Ile-Ala-Met-Asp-Lys-Ile-His-Gln-Gln-Asp-Phe-Val-Asn-Trp-Leu-Leu-Ala-Gln-Cys (NH$_2$) (SEQ ID NO: 22)

The following side chain protected amino acids were used: Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-His(Trt)-OH, Fmoc-Lys (Boc)-OH, Fmoc-Ser(tBu)-OH, Fmoc-Thr(tBu)-OH, Fmoc-Trp(Boc)-OH, Fmoc-Tyr(tBu)-OH.

When all the synthetic cycles were completed, the peptidyl resin was treated with 20% piperidine/dimethylformamide to remove the N-terminal Fmoc group, and then treated with final cleavage reagents (95% TFA, 2.5% H$_2$O, 2.5% EDT) for 2 hours. The solid resin was filtered, and the solution was concentrated through nitrogen bubble. The peptide was precipitated by chilled ethyl ether, and the crude stuff was then obtained by centrifuge. The crude peptide was dissolved in acetonitrile buffer, and then loaded onto semi-preparative reverse phase column. An acetonitrile gradient was run using a Waters HPLC system. The appropriate fractions were characterized by LC-MS, and then pooled together for lyophilization. An HPLC analysis of the product demonstrated a purity of more than 90%, and ESI-MS demonstrated the desired signals of the target peptide.

The analog 028, 087, and 096 were similarly prepared.

Example 3

Synthesis of the Analog 046 and Similar Fatty Acid Conjugated Peptides 0.05 mmol Fmoc-Rink amide resin in a 10 mL reaction vessel, and standard Fmoc-chemistry solid-phase peptide synthesis procedures were performed through the following sequence, with DIC/HOBt as the coupling reagents.

Tyr-Aib-Glu-Gly-Thr-Phe-Thr-Ser-Asp-Tyr-Ser-Ile-Tyr-Met-Glu-Lys-Glu-Ala-Val-Arg-Glu-Phe-Ile-Ala-Trp-Leu-Val-Lys(palmitoyl)-Gly (NH$_2$) (SEQ ID NO: 31)

The following side chain protected amino acids were used: Fmoc-Arg(Pbf)-OH, Fmoc-Asp(OtBu)-OH, Fmoc-Glu(OtBu)-OH, Fmoc-Lys (Boc)-OH, Fmoc-Lys(Alloc)-OH, Fmoc-Ser(tBu)-OH, Fmoc-Thr(tBu)-OH, Fmoc-Trp(Boc)-OH, Fmoc-Tyr(tBu)-OH.

When all the synthetic cycles were completed, the peptidyl resin was firstly treated with Pd(PPh$_3$)$_4$/dichloromethane for 1 hour to remove the Alloc protecting group, and palmitic acid was coupled to the epsilon-amine group of Lys at the position of 28. The resin was then treated by 20% piperidine/dimethylformamide to remove the N-terminal Fmoc group, and then treated with final cleavage reagents (95% TFA, 2.5% H$_2$O, 2.5% EDT) for 2 hours. The solid resin was filtered, and the solution was concentrated through nitrogen bubble. The peptide was precipitated by chilled ethyl ether, and the crude peptide was then obtained by centrifuge. The crude peptide was dissolved in acetonitrile buffer, and then loaded onto semi-preparative reverse phase column. An acetonitrile gradient was run using a Waters HPLC system. The appropriate fractions were characterized by LC-MS, and then pooled together for lyophilization. An HPLC analysis of the product demonstrated a purity of more than 90%, and ESI-MS demonstrated the desired signals of the target peptide.

The analogs 047 was similarly prepared.

Example 4

Synthesis of the Analog 065 and Similar Maleimido Residue Conjugated Peptides 0.05 mmol Fmoc-Rink amide resin in a 10 mL reaction vessel, and standard Fmoc-chemistry solid-phase peptide synthesis procedures were performed through the following sequence, with DIC/HOBt as the coupling reagents.

Tyr-Aib-Glu-Gly-Thr-Phe-Thr-Ser-Asp-Tyr-Ser-Ile-Tyr-Met-Glu-Lys-Glu-Ala-Val-Arg-Glu-Phe-Ile-Ala-Trp-Leu-Val-Lys(3-Maleimidopropionic acyl)-Gly(NH$_2$) (SEQ ID NO: 49)

The following side chain protected amino acids were used: Fmoc-Arg(Pbf)-OH, Fmoc-Asp(OtBu)-OH, Fmoc- Glu(OtBu)-OH, Fmoc-Lys (Boc)-OH, Fmoc-Lys(Alloc)-OH, Fmoc-Ser(tBu)-OH, Fmoc-Thr(tBu)-OH, Fmoc-Trp (Boc)-OH, Fmoc-Tyr(tBu)-OH.

When all the synthetic cycles were completed, the peptidyl resin was firstly treated with Pd(PPh$_3$)$_4$/dichloromethane for 1 hour to remove the Alloc protecting group, and 3-maleimidopropionic acid was coupled to the epsilon-amine group of Lys at the position of 28. The resin was then treated by 20% piperidine/dimethylformamide to remove the N-terminal Fmoc group, and then treated with final cleavage reagents (95% TFA, 2.5% H$_2$O, 2.5% EDT) for 2 hours. The solid resin was filtered, and the solution was concentrated through nitrogen bubble. The peptide was precipitated by chilled ethyl ether, and the crude stuff was then obtained by centrifuge. The crude peptide was dissolved in acetonitrile buffer, and then loaded onto semi-preparative reverse phase column. An acetonitrile gradient was run using a Waters HPLC system. The appropriate fractions were characterized by LC-MS, and then pooled together for lyophilization. An HPLC analysis of the product demonstrated a purity of more than 90%, and ESI-MS demonstrated the desired signals of the target peptide.

The analogs, 069, and 079 were similarly prepared.

Example 5

Synthesis of the Analog 052-2 and Similar Analogs Containing Lactam Bridge Formations 0.05 mmol Fmoc-Rink amide resin in a 10 mL reaction vessel, and standard Fmoc-chemistry solid-phase peptide synthesis procedures were performed through the following sequence, with DIC/HOBt as the coupling reagents.

Tyr-Aib-Glu-Gly-Thr-Phe-Thr-Ser-Asp-Tyr-Ser-Glu-
Tyr-Met-Glu-Lys-Glu-Ala-Val-Arg-Glu-Phe-Ile-
Ala-Trp-Leu-Val-Lys-Gly(NH$_2$)[lactam bridge
formation between Glu$^{12}$ and Lys$^{16}$] (SEQ ID NO: 37)

The following side chain protected amino acids were used: Fmoc-Arg(Pbf)-OH, Fmoc-Asp(OtBu)-OH, Fmoc-Glu(OtBu)-OH, Fmoc-Glu(OAll)-OH, Fmoc-Lys (Boc)-OH, Fmoc-Lys(Alloc)-OH, Fmoc-Ser(tBu)-OH, Fmoc-Thr (tBu)-OH, Fmoc-Trp(Boc)-OH, Fmoc-Tyr(tBu)-OH.

When all the synthetic cycles were completed, the peptidyl resin was firstly treated with Pd(PPh$_3$)$_4$/dichloromethane for 1 hour to remove the Alloc/OAll protecting groups, and latam bridge was formed under the coupling reagent of PyBOP/DIEA. The resin was then treated by 20% piperidine/dimethylformamide to remove the N-terminal Fmoc group, and then treated with final cleavage reagents (95% TFA, 2.5% H$_2$O, 2.5% EDT) for 2 hours. The solid resin was filtered, and the solution was concentrated through nitrogen bubble. The peptide was precipitated by chilled ethyl ether, and the crude stuff was then obtained by centrifuge. The crude peptide was dissolved in acetonitrile buffer, and then loaded onto semi-preparative reverse phase column. An acetonitrile gradient was run using a Waters HPLC system. The appropriate fractions were characterized by LC-MS, and then pooled together for lyophilization. An HPLC analysis of the product demonstrated a purity of more than 90%, and ESI-MS demonstrated the desired signals of the target peptide.

The analogs 053-2, 081, 084, and 085 were similarly prepared.

Example 6

Synthesis of the Analog 090 and Similar Analogs with Gamma-Glu as the Spacer 0.05 mmol Fmoc-Rink amide resin in a 10 mL reaction vessel, and standard Fmoc-chemistry solid-phase peptide synthesis procedures were performed through the following sequence, with DIC/HOBt as the coupling reagents.

Tyr-Aib-Glu-Gly-Thr-Phe-Thr-Ser-Asp-Tyr-Ser-Ile-
Tyr-Met-Glu-Lys-Glu-Ala-Val-Arg-Glu-Phe-Ile-
Ala-Trp-Leu-Val-Lys-Gly-Gly-Pro-Ser-Ser-Gly-
Ala-Pro-Pro-Pro-Ser-Lys(gamma-Glu-palmitoyl)
(NH$_2$) (SEQ ID NO: 66)

The following side chain protected amino acids were used: Fmoc-Arg(Pbf)-OH, Fmoc-Asp(OtBu)-OH, Fmoc-Glu(OtBu)-OH, Fmoc-Glu-OtBu, Fmoc-Lys (Boc)-OH, Fmoc-Lys(Alloc)-OH, Fmoc-Ser(tBu)-OH, Fmoc-Thr(tBu)-OH, Fmoc-Trp(Boc)-OH, Fmoc-Tyr(tBu)-OH, Boc-Tyr (tBu)-OH.

The last cycle was accomplished by the coupling of Boc-Tyr(tBu)-OH. When all the synthetic cycles were completed, the peptidyl resin was firstly treated with Pd(PPh$_3$)$_4$/dichloromethane for 1 hour to remove the Alloc protecting group, and gamma glutamyl was coupled to the epsilon-amine group of Lys at the position of 40. The resin was then treated by 20% piperidine/dimethylformamide to remove the Fmoc group, and then palmitic acid was coupled to the alpha-amine group of the spacer. The resin was finally treated with cleavage reagents (95% TFA, 2.5% H$_2$O, 2.5% EDT) for 2 hours. The solid resin was filtered, and the solution was concentrated through nitrogen bubble. The peptide was precipitated by chilled ethyl ether, and the crude stuff was then obtained by centrifuge. The crude peptide was dissolved in acetonitrile buffer, and then loaded onto semi-preparative reverse phase column. An acetonitrile gradient was run using a Waters HPLC system. The appropriate fractions were characterized by LC-MS, and then pooled together for lyophilization. An HPLC analysis of the product demonstrated a purity of more than 90%, and ESI-MS demonstrated the desired signals of the target peptide.

The analogs 091, 092, 093, 094, and 095 were similarly prepared.

Example 7

General PEGylation Protocol (Cys-Maleimido)

Generally, the GIP analog 087 containing Cys substitution is dissolved in phosphate buffered saline (~10 mg/mL) and equivalent maleimido-activated methoxyPEG reagent is added and the reaction stirred at room temperature while monitoring reaction progress through analytical HPLC. After 10-24 hours, the reaction mixture is acidified and loaded onto a preparative reverse phase column for purification using 0.1% TFA/cetonitrile gradient. The appropriate fractions were combined and lyophilized to produce the desired PEGylated peptides.

The analog 088 and 089 were similarly prepared.

The following list described all the GIP analogs synthesized in the present invention.

Native GIP:
(SEQ ID NO: 1)
Tyr-Ala-Glu-Gly-Thr-Phe-Ile-Ser-Asp-Tyr-Ser-Ile-Ala-Met-Asp-Lys-Ile-His-
Gln-Gln-Asp-Phe-Val-Asn-Trp-Leu-Leu-Ala-Gln(NH$_2$)

Analog 002:
(SEQ ID NO: 2)
Tyr-Aib-Glu-Gly-Thr-Phe-Thr-Ser-Asp-Tyr-Ser-Ile-Ala-Met-Glu-Lys-Ile-His-
Gln-Gln-Asp-Phe-Val-Asn-Trp-Leu-Leu-Ala-Gln(NH$_2$)

Analog 003:
(SEQ ID NO: 3)
Tyr-Aib-Glu-Gly-Thr-Phe-Thr-Ser-Asp-Tyr-Ser-Ile-Tyr-Met-Glu-Lys-Ile-His-
Gln-Gln-Asp-Phe-Val-Asn-Trp-Leu-Leu-Ala-Gln(NH$_2$)

Analog 004:
(SEQ ID NO: 4)
Tyr-Aib-Glu-Gly-Thr-Phe-Thr-Ser-Asp-Tyr-Ser-Ile-Phe(4-F)-Met(oxidation)-
Glu-Lys-Ile-His-Gln-Gln-Asp-Phe-Val-Asn-Trp-Leu-Leu-Ala-Gln(NH$_2$)

Analog 005:
(SEQ ID NO: 5)
Tyr-Aib-Glu-Gly-Thr-Phe-Thr-Ser-Asp-Tyr-Ser-Ile-Phe(4-NO$_2$)-Met(oxidation)-
Glu-Lys-Ile-His-Gln-Gln-Asp-Phe-Val-Asn-Trp-Leu-Leu-Ala-Gln(NH$_2$)

Analog 006:
(SEQ ID NO: 6)
Tyr-Aib-Glu-Gly-Thr-Phe-Ile-Ser-Asp-Tyr-Ser-Ile-Ala-Met(oxidation)-Glu-
Lys-Ile-His-Gln-Gln-Asp-Phe-Val-Asn-Trp-Leu-Leu-Ala-Gln(NH$_2$)

Analog 007:
(SEQ ID NO: 7)
Tyr-Aib-Glu-Gly-Thr-Phe-Thr-Ser-Asp-Tyr-Ser-Ile-Phe-Met(oxidation)-Glu-
Lys-Ile-His-Gln-Gln-Asp-Phe-Val-Asn-Trp-Leu-Leu-Ala-Gln(NH$_2$)

Analog 008:
(SEQ ID NO: 8)
Tyr-Aib-Glu-Gly-Thr-Phe-Thr-Ser-Asp-Tyr-Ser-Ile-Phe(4-NO$_2$)-Nle-Glu-Lys-
Ile-His-Gln-Gln-Asp-Phe-Val-Asn-Trp-Leu-Leu-Ala-Gln(NH$_2$)

Analog 009:
(SEQ ID NO: 9)
Tyr-Aib-Glu-Gly-Thr-Phe-Thr-Ser-Asp-Tyr-Ser-Ile-Phg-Nle-Glu-Lys-Ile-His-
Gln-Gln-Asp-Phe-Val-Asn-Trp-Leu-Leu-Ala-Gln(NH$_2$)

Analog 010:
(SEQ ID NO: 10)
Tyr-Aib-Glu-Gly-Thr-Phe-Ile-Ser-Asp-Tyr-Ser-Ile-Ala-Nle-Glu-Lys-Ile-His-
Gln-Gln-Asp-Phe-Val-Asn-Trp-Leu-Leu-Ala-Gln(NH$_2$)

Analog 011:
(SEQ ID NO: 11)
Tyr-Aib-Glu-Gly-Thr-Phe-Thr-Ser-Asp-Tyr-Ser-Ile-Phe-Nle-Glu-Lys-Ile-His-
Gln-Gln-Asp-Phe-Val-Asn-Trp-Leu-Leu-Ala-Gln(NH$_2$)

Analog 012:
(SEQ ID NO: 12)
Tyr-Aib-Glu-Gly-Thr-Phe-Thr-Ser-Asp-Tyr-Ser-Ile-Tyr-Nle-Glu-Lys-Ile-His-
Gln-Gln-Asp-Tyr-Val-Asn-Trp-Leu-Leu-Ala-Gln(NH$_2$)

Analog 013:
(SEQ ID NO: 13)
Tyr-Aib-Glu-Gly-Thr-Phe-Thr-Ser-Asp-Tyr-Ser-Ile-Tyr-Nle-Glu-Lys-Ile-His-
Gln-Gln-Asp-Tyr(4-Me)-Val-Asn-Trp-Leu-Leu-Ala-Gln(NH$_2$)

Analog 015:
(SEQ ID NO: 14)
Tyr-Aib-Glu-Gly-Thr-Phe-Thr-Ser-Asp-Tyr-Ser-Ile-Tyr-Nle-Glu-Lys-Ile-His-
Gln-Gln-Asp-Phe(4-F)-Val-Asn-Trp-Leu-Leu-Ala-Gln(NH$_2$)

Analog 016:
(SEQ ID NO: 15)
Tyr-Aib-Glu-Gly-Thr-Phe-Thr-Ser-Asp-Tyr-Ser-Ile-Phe(4-NO$_2$)-Met-Glu-Lys-
Ile-His-Gln-Gln-Asp-Phe-Val-Asn-Trp-Leu-Leu-Ala-Gln(NH$_2$)

Analog 020:
(SEQ ID NO: 16)
Tyr-Aib-Glu-Gly-Thr-Phe-Thr-Ser-Asp-Tyr-Ser-Ile-Tyr-Nle-Glu-Lys-Glu-Ala-
Gln-Gln-Asp-Phe-Val-Asn-Trp-Leu-Leu-Ala-Gln(NH$_2$)

-continued

Analog 021:
(SEQ ID NO: 17)
Tyr-Aib-Glu-Gly-Thr-Phe-Thr-Ser-Asp-Tyr-Ser-Ile-Tyr-Nle-Glu-Lys-Ile-His-
Gln-Gln-Asp-Phe-Val-Asn-Trp-Leu-Val-Arg-Gln(NH$_2$)

Analog 023:
(SEQ ID NO: 18)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly(NH$_2$)

Analog 024:
(SEQ ID NO: 19)
Tyr-Aib-Glu-Gly-Thr-Phe-Thr-Ser-Asp-Tyr-Ser-Ile-Tyr-Met-Glu-Lys-Glu-Ala-
Val-Arg-Leu-Phe-Ile-Glu-Trp-Leu-Lys-Asn-Gly(NH$_2$)

Analog 025:
(SEQ ID NO: 20)
Tyr-Aib-Glu-Gly-Thr-Phe-Thr-Ser-Asp-Tyr-Ser-Ile-Tyr-Met-Glu-Lys-Gln-Ala-
Ala-Lys-Glu-Phe-Ile-Ala-Trp-Leu-Val-Lys-Gly(NH$_2$)

Analog 026:
(SEQ ID NO: 21)
Tyr-Aib-Glu-Gly-Thr-Phe-Thr-Ser-Asp-Tyr-Ser-Ile-Tyr-Met-Glu-Lys-Gln-Ala-
Ala-Lys-Leu-Phe-Ile-Glu-Trp-Leu-Lys-Asn-Gly(NH$_2$)

Analog 028:
(SEQ ID NO: 22)
Tyr-Aib-Glu-Gly-Thr-Phe-Ile-Ser-Asp-Tyr-Ser-Ile-Ala-Met-Asp-Lys-Ile-His-
Gln-Gln-Asp-Phe-Val-Asn-Trp-Leu-Leu-Ala-Gln-Cys(NH$_2$)

Analog 029:
(SEQ ID NO: 23)
Tyr-Aib-Glu-Gly-Thr-Phe-Ile-Ser-Asp-Tyr-Ser-Ile-Ala-Met-Asp-Lys-Ile-His-
Gln-Gln-Asp-Phe-Val-Cys-Trp-Leu-Leu-Ala-Gln(NH$_2$)

Analog 030:
(SEQ ID NO: 24)
Tyr-Aib-Glu-Gly-Thr-Phe-Thr-Ser-Asp-Tyr-Ser-Ile-Tyr-Met-Glu-Lys-Glu-Ala-
Ala-Gln-Asp-Phe-Val-Asn-Trp-Leu-Leu-Ala-Gln(NH$_2$)

Analog 031:
(SEQ ID NO: 25)
Tyr-Aib-Glu-Gly-Thr-Phe-Thr-Ser-Asp-Tyr-Ser-Ile-Tyr-Met-Glu-Lys-Glu-Ala-
Ile-Gln-Asp-Phe-Val-Asn-Trp-Leu-Leu-Ala-Gln(NH$_2$)

Analog 032:
(SEQ ID NO: 26)
Tyr-Aib-Glu-Gly-Thr-Phe-Thr-Ser-Asp-Tyr-Ser-Ile-Tyr-Met-Glu-Lys-Glu-Ala-
Leu-Gln-Asp-Phe-Val-Asn-Trp-Leu-Leu-Ala-Gln(NH$_2$)

Analog 034:
(SEQ ID NO: 27)
Tyr-Aib-Glu-Gly-Thr-Phe-Thr-Ser-Asp-Tyr-Ser-Ile-Tyr-Met-Glu-Lys-Glu-Ala-
Val-Gln-Asp-Phe(4-Cl)-Val-Asn-Trp-Leu-Leu-Ala-Gln(NH$_2$)

Analog 040:
(SEQ ID NO: 28)
Tyr-Aib-Glu-Gly-Thr-Phe-Thr-Ser-Asp-Tyr-Ser-Ile-Tyr-Met-Glu-Lys-Glu-Ala-
Val-Lys-Asp-Phe(4-Cl)-Val-Asn-Trp-Leu-Leu-Ala-Gln(NH$_2$)

Analog 043:
(SEQ ID NO: 29)
Tyr-Aib-Glu-Gly-Thr-Phe-Thr-Ser-Asp-Tyr-Ser-Ile-Pal-Met-Glu-Lys-Ile-His-
Gln-Gln-Asp-Phe(4-Cl)-Val-Asn-Trp-Leu-Leu-Ala-Gln(NH$_2$)

Analog 044:
(SEQ ID NO: 30)
Tyr-Aib-Glu-Gly-Thr-Phe-Thr-Ser-Asp-Tyr-Ser-Ile-Tyr-Met-Glu-Lys-Ile-His-
Gln-Lys-Asp-Phe(4-Cl)-Val-Asn-Trp-Leu-Leu-Ala-Gln(NH$_2$)

Analog 046:
(SEQ ID NO: 31)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys(palmitoyl)-Gly(NH$_2$)

Analog 047:
(SEQ ID NO: 32)
Tyr-Aib-Glu-Gly-Thr-Phe-Thr-Ser-Asp-Tyr-Ser-Ile-Tyr-Met-Glu-Lys-Gln-Ala-
Ala-Lys-Glu-Phe-Ile-Ala-Trp-Leu-Val-Lys(palmitoyl)-Gly(NH$_2$)

-continued

Analog 048:
(SEQ ID NO: 33)
Tyr-Aib-Glu-Gly-Thr-Phe-Thr-Ser-Asp-Tyr-Ser-Ile-Tyr-Met-Glu-Lys-Glu-Ala-
Val-Arg-Leu-Phe-Ile-Glu-Trp-Leu-Lys(palmitoyl)-Asn-Gly(NH$_2$)

Analog 049:
(SEQ ID NO: 34)
Tyr-Aib-Glu-Gly-Thr-Phe-Thr-Ser-Asp-Tyr-Ser-Ile-Tyr-Met-Glu-Lys-Gln-Ala-
Ala-Lys-Leu-Phe-Ile-Glu-Trp-Leu-Lys(palmitoyl)-Asn-Gly(NH$_2$)

Analog 051:
(SEQ ID NO: 35)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly-Gly-Pro-Ser-Ser-Gly-Ala-Pro-
Pro-Pro-Ser(NH$_2$)

Analog 052-1:
(SEQ ID NO: 36)
Tyr-Aib-Glu-Gly-Thr-Phe-Thr-Ser-Asp-Tyr-Ser-Glu-Tyr-Met-Glu-Lys-Glu-Ala-
Val-Arg-Glu-Phe-Ile-Ala-Trp-Leu-Val-Lys-Gly(NH$_2$)

Analog 052-2:
(SEQ ID NO: 37)
Tyr-Aib-Glu-Gly-Thr-Phe-Thr-Ser-Asp-Tyr-Ser-Glu-Tyr-Met-Glu-Lys-Glu-Ala-
Val-Arg-Glu-Phe-Ile-Ala-Trp-Leu-Val-Lys-Gly(NH$_2$)
[lactam formation between 12 and 16]

Analog 053-1:
(SEQ ID NO: 38)
Tyr-Aib-Glu-Gly-Thr-Phe-Thr-Ser-Asp-Tyr-Ser-Ile-Tyr-Met-Glu-Lys-Glu-Ala-
Val-Glu-Glu-Phe-Ile-Ala-Trp-Leu-Val-Lys-Gly(NH$_2$)

Analog 053-2:
(SEQ ID NO: 39)
Tyr-Aib-Glu-Gly-Thr-Phe-Thr-Ser-Asp-Tyr-Ser-Ile-Tyr-Met-Glu-Lys-Glu-Ala-
Val-Glu-Glu-Phe-Ile-Ala-Trp-Leu-Val-Lys-Gly(NH$_2$)
[lactam formation between 16 and 20]

Analog 054-1:
(SEQ ID NO: 40)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Glu-Trp-Leu-Val-Lys-Gly(NH$_2$)

Analog 056:
(SEQ ID NO: 41)
Tyr-Aib-Glu-Gly-Thr-Phe-Thr-Ser-Asp-Tyr-Ser-Ile-Tyr-Met-Glu-Lys-Glu-Ala-
Ala-Arg-Glu-Phe-Ile-Ala-Trp-Leu-Val-Lys-Gly(NH$_2$)

Analog 057:
(SEQ ID NO: 42)
Tyr-Aib-Glu-Gly-Thr-Phe-Thr-Ser-Asp-Tyr-Ser-Ile-Tyr-Met-Glu-Lys-Glu-Ala-
Val-Lys-Glu-Phe-Ile-Ala-Trp-Leu-Val-Lys-Gly(NH$_2$)

Analog 058:
(SEQ ID NO: 43)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly-Lys-Gly(NH$_2$)

Analog 059:
(SEQ ID NO: 44)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly-Arg-Gly(NH$_2$)

Analog 060:
(SEQ ID NO: 45)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly-Lys-Lys-Lys-Lys-Lys(NH$_2$)

Analog 062:
(SEQ ID NO: 46)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe(4-Cl)-Ile-Ala-Trp-Leu-Val-Lys-Gly(NH$_2$)

Analog 063:
(SEQ ID NO: 47)
Tyr-Aib-Glu-Gly-Thr-Phe-Thr-Ser-Asp-Tyr-Ser-Ile-Tyr-Met-Glu-Lys-Glu-Ala-
Val-Arg-Glu-Nal-Ile-Ala-Trp-Leu-Val-Lys-Gly(NH$_2$)

-continued

Analog 064: (SEQ ID NO: 48)
Tyr-Aib-Glu-Gly-Thr-Phe-Thr-Ser-Asp-Tyr-Ser-Ile-Pal-Met-Glu-Lys-Glu-Ala-
Val-Arg-Glu-Phe-Ile-Ala-Trp-Leu-Val-Lys-Gly(NH$_2$)

Analog 065: (SEQ ID NO: 49)
Tyr-Aib-Glu-Gly-Thr-Phe-Thr-Ser-Asp-Tyr-Ser-Ile-Tyr-Met-Glu-Lys-Glu-Ala-
Val-Arg-Glu-Phe-Ile-Ala-Trp-Leu-Val-Lys-Gly(NH$_2$)

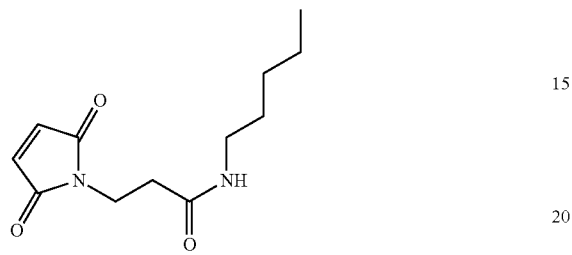

Analog 066: (SEQ ID NO: 50)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(NH$_2$)

Analog 067: (SEQ ID NO: 51)
Tyr-Aib-Glu-Gly-Thr-Phe-Thr-Ser-Asp-Tyr-Ser-Ile-Tyr-Met-Glu-Lys-Glu-
Ala-Val-Lys(palmitoyl)-Glu-Phe-Ile-Ala-Trp-Leu-Val-Lys-Gly(NH$_2$)

Analog 068: (SEQ ID NO: 52)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(palmitoyl)(NH$_2$)

Analog 069: (SEQ ID NO: 53)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(NH$_2$)

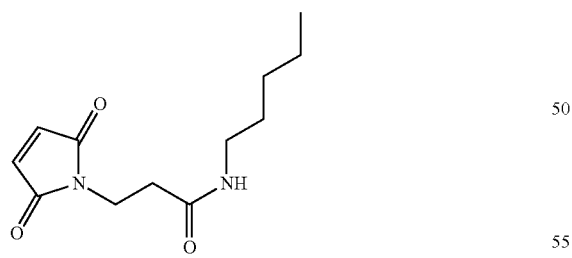

Analog 071: (SEQ ID NO: 54)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys-Lys-Lys-Lys-Lys(NH$_2$)

-continued

Analog 074:
(SEQ ID NO: 55)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(biotin)(NH$_2$)

Analog 075:
(SEQ ID NO: 56)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Arg-Arg-Arg-Arg-
Arg(NH$_2$)

Analog 078:
(SEQ ID NO: 57)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys-Lys-Lys-Lys-Lys(palmitoyl)(NH$_2$)

Analog 079:
(SEQ ID NO: 58)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys-Lys-Lys-Lys-Lys-Lys(NH$_2$)

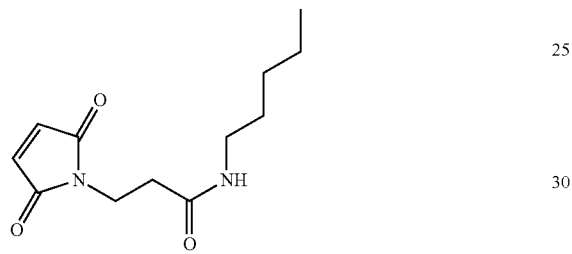

Analog 080:
(SEQ ID NO: 59)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys-Lys-Lys-Lys-Lys-Lys(biotin)(NH$_2$)

Analog 081:
(SEQ ID NO: 60)
Tyr-Aib-Glu-Gly-Thr-Phe-Thr-Ser-Asp-Tyr-Ser-Glu-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser(NH$_2$)
[lactam formation between 12 and 16]

Analog 084:
(SEQ ID NO: 61)
Tyr-Aib-Glu-Gly-Thr-Phe-Thr-Ser-Asp-Tyr-Ser-Glu-Tyr-Met-Glu-Lys-Glu-
Ala-Val-Arg-Glu-Phe-Ile-Ala-Trp-Leu-Val-Lys-Gly-Lys(palmitoyl)(NH$_2$)
[lactam formation between 12 and 16]

Analog 085:
(SEQ ID NO: 62)
Tyr-Aib-Glu-Gly-Thr-Phe-Thr-Ser-Asp-Tyr-Ser-Ile-Tyr-Met-Glu-Lys-Glu-
Ala-Val-Lys-Glu-Phe-Ile-Glu-Trp-Leu-Val-Lys-Gly-Gly-Pro-Ser-Ser-Gly-
Ala-Pro-Pro-Pro-Ser(NH$_2$)
[lactam formation between 20 and 24]

Analog 087:
(SEQ ID NO: 63)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(NH$_2$)

Analog 088:
(SEQ ID NO: 64)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(20k PEG)(NH$_2$)

-continued

Analog 089:
(SEQ ID NO: 65)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(40k PEG)(NH$_2$)

Analog 090:
(SEQ ID NO: 66)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(gamma-Glu-palmitoyl)(NH$_2$)

Analog 091:
(SEQ ID NO: 67)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(gamma-Glu-gamma-Glu-palmitoyl)(NH$_2$)

Analog 092:
(SEQ ID NO: 68)
Tyr-Aib-Glu-Gly-Thr-Phe-Thr-Ser-Asp-Tyr-Ser-Ile-Tyr-Met-Glu-Lys-Glu-
Ala-Val-Lys(gamma-Glu-palmitoyl)-Glu-Phe-Ile-Ala-Trp-Leu-Val-Lys-Gly-
Gly-Pro-Ser-Ser-Gly-Ala-Pro-Pro-Pro-Ser(NH$_2$)

Analog 093:
(SEQ ID NO: 69)
Tyr-Aib-Glu-Gly-Thr-Phe-Thr-Ser-Asp-Tyr-Ser-Ile-Tyr-Met-Glu-Lys-Glu-
Ala-Val-Lys(gamma-Glu-gamma-Glu-palmitoyl)-Glu-Phe-Ile-Ala-Trp-Leu-
Val-Lys-Gly-Gly-Pro-Ser-Ser-Gly-Ala-Pro-Pro-Pro-Ser(NH$_2$)

Analog 094:
(SEQ ID NO: 70)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys(gamma-Glu-palmitoyl)-Gly-
Gly-Pro-Ser-Ser-Gly-Ala-Pro-Pro-Pro-Ser(NH$_2$)

Analog 095:
(SEQ ID NO: 71)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys(γ-Glu-γ-Glu-palmitoyl)-
Gly-Gly-Pro-Ser-Ser-Gly-Ala-Pro-Pro-Pro-Ser(NH$_2$)

Analog 096:
(SEQ ID NO: 72)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Cys-Trp-Leu-Val-Lys-Gly-Gly-Pro-Ser-Ser-Gly-
Ala-Pro-Pro-Pro-Ser-Lys(palmitoyl)(NH$_2$)

Analog 097:
(SEQ ID NO: 73)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Cys(20k PEG)-Trp-Leu-Val-Lys-Gly-Gly-Pro-Ser-
Ser-Gly-Ala-Pro-Pro-Pro-Ser-Lys(p almitoyl)(NH$_2$)

Analog 098:
(SEQ ID NO: 74)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Cys(40k PEG)-Trp-Leu-Val-Lys-Gly-Gly-Pro-Ser-
Ser-Gly-Ala-Pro-Pro-Pro-Ser-Lys(palmitoyl)(NH$_2$)

Analog 099:
(SEQ ID NO: 75)
Tyr-Aib-Glu-Gly-Thr-Phe-Thr-Ser-Asp-Tyr-Ser-Glu-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(palmitoyl)(NH$_2$)
[lactam formation between 12 and 16]

Analog 100:
(SEQ ID NO: 76)
Tyr-Aib-Glu-Gly-Thr-Phe-Thr-Ser-Asp-Tyr-Ser-Ile-Tyr-Met-Glu-Lys-Glu-
Ala-Val-Glu-Glu-Phe-Ile-Ala-Trp-Leu-Val-Lys-Gly-Gly-Pro-Ser-Ser-Gly-
Ala-Pro-Pro-Pro-Ser-Lys(palmitoyl)(NH$_2$)
[lactam formation between 16 and 20]

Analog 101:
(SEQ ID NO: 77)
Tyr-Aib-Glu-Gly-Thr-Phe-Thr-Ser-Asp-Tyr-Ser-Ile-Tyr-Met-Glu-Lys-Glu-
Ala-Val-Lys-Glu-Phe-Ile-Glu-Trp-Leu-Val-Lys-Gly-Gly-Pro-Ser-Ser-Gly-
Ala-Pro-Pro-Pro-Ser-Lys(palmitoyl)(NH$_2$)
[lactam formation between 20 and 24]

-continued

Analog 102:
(SEQ ID NO: 78)
Tyr-Aib-Glu-Gly-Thr-Phe-Thr-Ser-Asp-Tyr-Ser-Ile-Tyr-Met-Glu-Lys-Glu-
Ala-Val-Lys-Glu-Phe-Ile-Glu-Trp-Leu-Val-Lys-Gly-Gly-Pro-Ser-Ser-Gly-
Ala-Pro-Pro-Pro-Ser-Lys(palmitoyl)(NH$_2$)
[lactam formation between 24 and 28]

Analog 104:
(SEQ ID NO: 79)
Tyr-Aib-Glu-Gly-Thr-Phe-Thr-Ser-Asp-Tyr-Ser-Ile-Tyr-Nle-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(palmitoyl)(NH$_2$)

Analog 105:
(SEQ ID NO: 80)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Cys-Trp-Leu-Val-Lys-Gly-Gly-Pro-Ser-Ser-Gly-
Ala-Pro-Pro-Pro-Ser-Lys(NH$_2$)

Analog 106:
(SEQ ID NO: 81)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(hexadecanedioic acyl)(NH$_2$)

Analog 107:
(SEQ ID NO: 82)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Cys-Trp-Leu-Val-Lys-Gly-Gly-Pro-Ser-Ser-Gly-
Ala-Pro-Pro-Pro-Ser(NH$_2$)

Analog 108:
(SEQ ID NO: 83)
Tyr-Aib-Glu-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser(cholic acyl)(NH$_2$)

Analog 114:
(SEQ ID NO: 84)
Tyr-Aib-Glu-Gly-Thr-Phe-Ile-Ser-Asp-Tyr-Ser-Ile-Tyr-Met-Glu-Lys-Glu-
Ala-Val-Arg-Glu-Phe-Ile-Cys-Trp-Leu-Val-Lys-Gly-Gly-Pro-Ser-Ser-Gly-
Ala-Pro-Pro-Pro-Lys(palmitoyl)(NH$_2$)

Analog 115:
(SEQ ID NO: 85)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Cys-Trp-Leu-Val-Lys-Gly-Gly-Pro-Ser-Ser-Gly-
Ala-Pro-Pro-Pro-Lys(palmitoyl)(NH$_2$)

Analog 116:
(SEQ ID NO: 86)
Tyr-Aib-Glu-Gly-Thr-Phe-Ile-Ser-Asp-Tyr-Ser-Ile-Tyr-Met-Glu-Lys-Glu-
Ala-Val-Arg-Glu-Phe-Ile-Cys(40k PEG)-Trp-Leu-Val-Lys-Gly-Gly-Pro-Ser-
Ser-Gly-Ala-Pro-Pro-Pro-Lys(palmitoyl)(NH$_2$)

Analog 117:
(SEQ ID NO: 87)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Cys(40k PEG)-Trp-Leu-Val-Lys-Gly-Gly-Pro-Ser-
Ser-Gly-Ala-Pro-Pro-Pro-Lys(palmitoyl)(NH$_2$)

Analog 120:
(SEQ ID NO: 88)
Tyr-Aib-Gln-Gly-Thr-Phe-Thr-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(palmitoyl)(NH$_2$)

Analog 121:
(SEQ ID NO: 89)
Tyr-Aib-Glu-Gly-Thr-Phe-Ile-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(NH$_2$)

Analog 122:
(SEQ ID NO: 90)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(NH$_2$)

-continued

Analog 123:
(SEQ ID NO: 91)
Tyr-Aib-Glu-Gly-Thr-Phe-Ile-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(40k PEG)(NH₂)

Analog 124:
(SEQ ID NO: 92)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(40k PEG)(NH₂)

Analog 125:
(SEQ ID NO: 93)
Tyr-Aib-Gln-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(NH₂)

Analog 126:
(SEQ ID NO: 94)
Tyr-Aib-Gln-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(40 k PEG)(NH₂)

Analog 127:
(SEQ ID NO: 95)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Lys(40 k PEG)(NH₂)

Analog 128:
(SEQ ID NO: 96)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Ala-Trp-Leu-Val-Lys-Gly-Gly-Pro-Ser-Ser-Gly-
Ala-Pro-Pro-Pro-Ser-Cys(palmitoyl)(NH₂)

Analog 129:
(SEQ ID NO: 97)
Tyr-Aib-Glu-Gly-Thr-Phe-Ser-Ser-Asp-Tyr-Ser-Ile-Tyr-Met-Glu-Lys(Biotin)-
Glu-Ala-Val-Arg-Glu-Phe-Ile-Ala-Trp-Leu-Val-Lys(Biotin)-Gly-Gly-Pro-
Ser-Ser-Gly-Ala-Pro-Pro-Pro-Ser-Lys(NH₂)

Analog 133:
(SEQ ID NO: 98)
Tyr-Aib-Glu-Gly-Thr-Phe-Ser-Ser-Asp-Tyr-Ser-Ile-Tyr-Met-Glu-Lys-Glu-
Ala-Val-Arg-Glu-Phe-Ile-Cys(40k PEG)-Trp-Leu-Val-Lys-Gly-Gly-Pro-Ser-
Ser-Gly-Ala-Pro-Pro-Pro-Ser-Lys(NH₂)

Exentin-4:
(SEQ ID NO: 99)
His-Gly-Glu-Gly-Thr-Phe-Thr-Ser-Asp-Leu-Ser-Lys-Gln-Met-Glu-Glu-Glu-
Ala-Val-Arg-Leu-Phe-Ile-Glu-Trp-Leu-Lys-Asn-Gly-Gly-Pro-Ser-Ser-Gly-
Ala-Pro-Pro-Pro-Ser GLP-1:
(SEQ ID NO: 100)
His-Ala-Glu-Gly-Thr-Phe-Thr-Ser-Asp-Val-Ser-Ser-Tyr-Leu-Glu-Gly-Gln-
Ala-Ala-Lys-Glu-Phe-Ile-Ala-Trp-Leu-Val-Lys-Gly-Arg The peptide characterization information was listed in Table 2.

TABLE 2

| Analog Number | HPLC Retention time (total time) | MW | MS data |
|---|---|---|---|
| 002 | 9.482 min (15 min) | 3419.85 | [M + 2H]²⁺ = 1710.0; [M + 3H]³⁺ = 1140.5; [M + 4H]⁴⁺ = 855.7 |
| 003 | 9.552 min (15 min) | 3511.95 | [M + 2H]²⁺ = 1756.0; [M + 3H]³⁺ = 1171.4; [M + 4H]⁴⁺ = 878.8 |
| 004 | 10.042 min (15 min) | 3529.94 | [M + 2H]²⁺ = 1765.5; [M + 3H]³⁺ = 1177.3; [M + 4H]⁴⁺ = 883.3 |

TABLE 2-continued

| Analog Number | HPLC Retention time (total time) | MW | MS data |
|---|---|---|---|
| 005 | 10.042 min (15 min) | 3556.94 | [M + 2H]²⁺ = 1779.0; [M + 3H]³⁺ = 1186.2; [M + 4H]⁴⁺ = 890.0 |
| 006 | 9.919 min (15 min) | 3433.87 | [M + 2H]²⁺ = 1717.1; [M + 3H]³⁺ = 1145.4; [M + 4H]⁴⁺ = 859.3 |
| 007 | 10.004 min (15 min) | 3511.95 | [M + 2H]²⁺ = 1756.6; [M + 3H]³⁺ = 1171.1; [M + 4H]⁴⁺ = 879.1 |
| 008 | 10.220 min (15 min) | 3522.91 | [M + 2H]²⁺ = 1761.9; [M + 3H]³⁺ = 1175.1; [M + 4H]⁴⁺ = 881.7 |

TABLE 2-continued

| Analog Number | HPLC Retention time (total time) | MW | MS data |
|---|---|---|---|
| 009 | 10.094 min (15 min) | 3463.88 | $[M + 2H]^{2+} = 1731.9$; $[M + 3H]^{3+} = 1155.0$; $[M + 4H]^{4+} = 866.9$ |
| 010 | 10.144 min (15 min) | 3399.84 | $[M + 2H]^{2+} = 1701.9$; $[M + 3H]^{3+} = 1133.9$; $[M + 4H]^{4+} = 851.0$; $[M + 5H]^{5+} = 681.1$ |
| 011 | 10.176 min (15 min) | 3477.91 | $[M + 2H]^{2+} = 1739.6$; $[M + 3H]^{3+} = 1160.0$; $[M + 4H]^{4+} = 870.7$ |
| 012 | 9.857 min (15 min) | 3509.91 | $[M + 2H]^{2+} = 1755.1$; $[M + 3H]^{3+} = 1170.6$; $[M + 4H]^{4+} = 878.3$ |
| 013 | 10.110 min (15 min) | 3523.93 | $[M + 2H]^{2+} = 1762.1$; $[M + 3H]^{3+} = 1175.4$; $[M + 4H]^{4+} = 881.8$ |
| 015 | 9.960 min (11 min) | 3511.90 | $[M + 2H]^{2+} = 1756.6$; $[M + 3H]^{3+} = 1171.3$; $[M + 4H]^{4+} = 878.8$ |
| 016 | 10.151 min (15 min) | 3540.94 | $[M + 2H]^{2+} = 1770.5$; $[M + 3H]^{3+} = 1180.8$; $[M + 4H]^{4+} = 886.3$ |
| 020 | 10.352 min (15 min) | 3443.80 | $[M + 2H]^{2+} = 1722.1$; $[M + 3H]^{3+} = 1148.6$; $[M + 4H]^{4+} = 861.9$ |
| 021 | 9.778 min (15 min) | 3564.99 | $[M + 2H]^{2+} = 1782.1$; $[M + 3H]^{3+} = 1188.9$; $[M + 4H]^{4+} = 892.1$ |
| 023 | 4.353 min (10 min) | 3417.92 | $[M + 2H]^{2+} = 1709.0$; $[M + 3H]^{3+} = 1139.8$; $[M + 4H]^{4+} = 855.3$ |
| 024 | 4.360 min (10 min) | 3474.97 | $[M + 2H]^{2+} = 1738.1$; $[M + 3H]^{3+} = 1159.0$; $[M + 4H]^{4+} = 869.5$ |
| 025 | 4.760 min (10 min) | 3360.86 | $[M + 2H]^{2+} = 1680.5$; $[M + 3H]^{3+} = 1120.9$; $[M + 4H]^{4+} = 841.1$ |
| 026 | 4.857 min (10 min) | 3417.92 | $[M + 2H]^{2+} = 1709.1$; $[M + 3H]^{3+} = 1140.0$; $[M + 4H]^{4+} = 855.3$ |
| 028 | 4.729 min (12 min) | 3521.02 | $[M + 2H]^{2+} = 1760.6$; $[M + 3H]^{3+} = 1174.2$; $[M + 4H]^{4+} = 881.1$ |
| 029 | 7.069 min (15 min) | 3406.91 | $[M + 2H]^{2+} = 1704.0$; $[M + 3H]^{3+} = 1136.3$; $[M + 4H]^{4+} = 852.6$ |
| 030 | 5.059 min (12 min) | 3404.79 | $[M + 2H]^{2+} = 1702.9$; $[M + 3H]^{3+} = 1135.5$; $[M + 4H]^{4+} = 852.0$ |
| 031 | | 3446.87 | $[M + 2H]^{2+} = 1724.0$; $[M + 3H]^{3+} = 1149.7$; $M + 4H]^{4+} = 862.7$; |
| 034 | 5.552 min (10 min) | 3467.29 | $[M + 2H]^{2+} = 1733.9$; $[M + 3H]^{3+} = 1156.3$; $[M + 4H]^{4+} = 867.7$ |
| 040 | 4.482 min (10 min) | 3467.33 | $[M + 2H]^{2+} = 1734.0$; $[M + 3H]^{3+} = 1156.5$; $[M + 4H]^{4+} = 867.7$ |
| 043 | 6.379 min (12 min) | 3531.38 | $[M + 2H]^{2+} = 1766.0$; $[M + 3H]^{3+} = 1177.8$; $[M + 4H]^{4+} = 883.7$ |
| 046 | 16.928 min (20 min) | 3656.33 | $[M + 2H]^{2+} = 1828.5$; $[M + 3H]^{3+} = 1219.4$; $[M + 4H]^{4+} = 915.0$ |
| 047 | 7.127 min (10 min) | 3599.28 | $[M + 2H]^{2+} = 1800.2$; $[M + 3H]^{3+} = 1200.5$; $[M + 4H]^{4+} = 900.7$ |
| 048 | 7.404 min (10 min) | 3713.38 | $[M + 3H]^{3+} = 1238.2$; $[M + 4H]^{4+} = 929.2$ |
| 049 | 21.892 min (30 min) | 3656.33 | $[M + 2H]^{2+} = 1828.2$; $[M + 3H]^{3+} = 1219.0$; $[M + 4H]^{4+} = 915.0$ |
| 051 | 18.947 min (30 min) | 4252.81 | $[M + 3H]^{3+} = 1418.1$; $[M + 4H]^{4+} = 1064.0$; $[M + 5H]^{5+} = 851.6$ |
| 052-1 | 17.520 min (25 min) | 3433.87 | $[M + 3H]^{3+} = 1145.3$; $[M + 4H]^{4+} = 859.4$; $[M + 5H]^{5+} = 687.8$ |
| 052-2 | 19.789 min (30 min) | 3415.86 | $[M + 3H]^{3+} = 1139.5$; $[M + 4H]^{4+} = 854.2$ |
| 053-1 | 20.460 min (30 min) | 3390.84 | $[M + 2H]^{2+} = 1695.4$; $[M + 3H]^{3+} = 1131.0$; $[M + 4H]^{4+} = 848.6$ |
| 053-2 | 21.163 min (30 min) | 3372.83 | $[M + 2H]^{2+} = 1686.4$; $[M + 3H]^{3+} = 1125.0$; $[M + 4H]^{4+} = 844.2$ |
| 054-1 | 17.775 min (25 min) | 3475.95 | $[M + 3H]^{3+} = 1159.2$; $[M + 4H]^{4+} = 869.9$ |
| 057 | 7.479 min (15 min) | 3389.9 | $[M + 3H]^{3+} = 1130.7$; $[M + 4H]^{4+} = 848.5$ |
| 060 | 16.558 min (25 min) | 4058.79 | $[M + 3H]^{3+} = 1353.8$; $[M + 4H]^{4+} = 1015.6$; $[M + 5H]^{5+} = 812.7$ |
| 065 | 7.313 min (12 min) | 3569.04 | $[M + 3H]^{3+} = 1190.3$; $[M + 4H]^{4+} = 893.2$ |
| 066 | 2.036 min (5 min) | 4380.98 | $[M + 3H]^{3+} = 1460.8$; $[M + 4H]^{4+} = 1096.1$ |
| 067 | 7.395 min (10 min) | 3628.32 | $[M + 3H]^{3+} = 1210.1$; $[M + 4H]^{4+} = 908.0$ |
| 068 | 21.065 min (30 min) | 4619.4 | $[M + 3H]^{3+} = 1540.5$; $[M + 4H]^{4+} = 1155.6$; $[M + 5H]^{5+} = 924.9$ |
| 069 | 18.348 min (30 min) | 4532.1 | $[M + 3H]^{3+} = 1511.3$; $[M + 4H]^{4+} = 1133.8$; $[M + 5H]^{5+} = 907.6$ |
| 071 | 17.443 min (30 min) | 5021.86 | $[M + 3H]^{3+} = 1674.3$; $[M + 4H]^{4+} = 1256.2$; $[M + 5H]^{5+} = 1005.3$ |
| 074 | 18.290 min (30 min) | 4607.28 | $[M + 3H]^{3+} = 1536.4$; $[M + 4H]^{4+} = 1152.5$ |
| 075 | 3.770 min (10 min) | 4355.05 | $[M + 3H]^{3+} = 1452.5$; $[M + 4H]^{4+} = 1089.6$; $[M + 5H]^{5+} = 872.0$ |
| 078 | 19.728 min (30 min) | 5260.28 | $[M + 4H]^{4+} = 1315.7$; $[M + 5H]^{5+} = 1052.9$; $[M + 6H]^{6+} = 877.7$; $[M + 7H]^{7+} = 758.8$ |
| 079 | 9.565 min (30 min) | 5172.98 | $[M + 4H]^{4+} = 1293.9$; $[M + 5H]^{5+} = 1035.5$; $[M + 6H]^{6+} = 863.1$; $[M + 7H]^{7+} = 739.9$; $[M + 8H]^{8+} = 647.6$ |
| 080 | 9.534 min (30 min) | 5248.16 | $[M + 4H]^{4+} = 1312.5$; $[M + 5H]^{5+} = 1050.4$; $[M + 6H]^{6+} = 875.6$; $[M + 7H]^{7+} = 750.8$; $[M + 8H]^{8+} = 656.9$ |
| 081 | 8.349 min (15 min) | 4250.75 | $[M + 3H]^{3+} = 1417.4$; $[M + 4H]^{4+} = 1074.2$; $[M + 5H]^{5+} = 851.1$ |
| 084 | 8.977 min (12 min) | 3782.45 | $[M + 3H]^{3+} = 1261.6$; $[M + 4H]^{4+} = 946.7$; $[M + 5H]^{5+} = 757.7$ |
| 085 | 5.154 min (10 min) | 4264.81 | $[M + 3H]^{3+} = 1422.1$; $[M + 4H]^{4+} = 1067.0$; $[M + 5H]^{5+} = 854.0$ |
| 087 | 7.335 min (15 min) | 4355.95 | $[M + 3H]^{3+} = 1452.2$; $[M + 4H]^{4+} = 1089.8$; $[M + 5H]^{5+} = 872.2$ |
| 088 | 5.181 min (10 min) | 24355.95 | To be determined by MALDI-TOF |
| 089 | 7.440 min (15 min) | 44355.95 | To be determined by MALDI-TOF |
| 090 | 8.778 min (15 min) | 4748.52 | $[M + 4H]^{4+} = 1187.8$; $[M + 5H]^{5+} = 950.6$; $[M + 6H]^{6+} = 792.6$ |
| 091 | 8.690 min (15 min) | 4877.63 | $[M + 4H]^{4+} = 1220.1$; $[M + 5H]^{5+} = 976.6$; $[M + 6H]^{6+} = 813.6$ |

TABLE 2-continued

| Analog Number | HPLC Retention time (total time) | MW | MS data |
|---|---|---|---|
| 092 | 8.775 min (15 min) | 4592.33 | $[M + 3H]^{3+}$ = 1531.7; $[M + 4H]^{4+}$ = 1149.2 |
| 093 | 8.655 min (15 min) | 4721.44 | $[M + 3H]^{3+}$ = 1574.7; $[M + 4H]^{4+}$ = 1181.4 |
| 094 | 8.360 min (15 min) | 4620.34 | $[M + 2H]^{2+}$ = 2311.1; $[M + 3H]^{3+}$ = 1541.0; $[M + 4H]^{4+}$ = 1156.2 |
| 096 | 8.504 min (15 min) | 4651.46 | $[M + 3H]^{3+}$ = 1551.1; $[M + 4H]^{4+}$ = 1163.9; $[M + 5H]^{5+}$ = 931.5 |
| 098 | 8.087 min (15 min) | 44651.46 | To be determined by MALDI-TOF |
| 099 | 15.367 min (20 min) | 4617.34 | $[M + 3H]^{3+}$ = 1539.9; $[M + 4H]^{4+}$ = 1155.4; $[M + 5H]^{5+}$ = 924.5 |
| 100 | 2.193 min (5 min) | 4574.31 | $[M + 4H]^{4+}$ = 1144.6; $[M + 5H]^{5+}$ = 916.0; $[M + 6H]^{6+}$ = 763.7 |
| 101 | 3.195 min (5 min) | 4631.41 | $[M + 3H]^{4+}$ = 1558.8; $[M + 4H]^{5+}$ = 927.5 |
| 102 | 2.178 min (5 min) | 4631.41 | $[M + 3H]^{4+}$ = 1558.8; $[M + 4H]^{5+}$ = 927.5; $[M + 5H]^{6+}$ = 773.1 |
| 104 | 2.141 min (5 min) | 4601.36 | $[M + 3H]^{3+}$ = 1534.8; $[M + 4H]^{4+}$ = 1151.3; $[M + 5H]^{5+}$ = 921.4; $[M + 6H]^{6+}$ = 768.2 |
| 105 | 2.049 min (5 min) | 4413.07 | $[M + 3H]^{3+}$ = 1471.7; $[M + 4H]^{4+}$ = 1104.3; $[M + 5H]^{5+}$ = 883.8; $[M + 6H]^{6+}$ = 736.8 |
| 106 | 6.692 min (10 min) | 4649.38 | $[M + 3H]^{3+}$ = 1550.7; $[M + 4H]^{4+}$ = 1163.3; $[M + 5H]^{5+}$ = 931.0; $[M + 6H]^{6+}$ = 776.2 |
| 108 | | 4771.27 | $[M + 4H]^{4+}$ = 1193.9; $[M + 5H]^{5+}$ = 955.5; $[M + 6H]^{6+}$ = 796.5 |
| 114 | | 4663.52 | $[M + 4H]^{4+}$ = 1166.8; $[M + 5H]^{5+}$ = 933.8; $[M + 6H]^{6+}$ = 778.6 |
| 115 | 2.976 min (5 min) | 4637.44 | $[M + 4H]^{4+}$ = 1160.2; $[M + 5H]^{5+}$ = 928.6; $[M + 6H]^{6+}$ = 774.2 |
| 120 | 2.937 min (5 min) | 4618.41 | $[M + 4H]^{4+}$ = 1155.5; $[M + 5H]^{5+}$ = 924.9; $[M + 6H]^{6+}$ = 771.1 |
| 121 | 2.219 min (5 min) | 4368.00 | $[M + 3H]^{3+}$ = 1456.6; $[M + 4H]^{4+}$ = 1092.9; $[M + 5H]^{5+}$ = 874.8; $[M + 6H]^{6+}$ = 730.1 |
| 122 | | 4341.92 | $[M + 3H]^{3+}$ = 1448.3; $[M + 4H]^{4+}$ = 1086.4; $[M + 5H]^{5+}$ = 469.5; $[M + 6H]^{6+}$ = 725.0 |

Example 8

General cAMP Induction Assay Protocol

Principle of the Assay

The cAMP in the sample or standard competes with horseradish peroxidase (HRP)-labeled cAMP conjugate for binding sites on the anti-cAMP antibodies. In the absence of cAMP, most of the HRP-cAMP conjugate is bound to the antibody. Increasing concentrations of cAMP competitively decrease the amount of bound conjugate, thus decreasing measured HRP activity.

Materials and Equipment

Assay kit: CatchPoint™ Cyclic-AMP Fluorescent Assay Kit (Molecular Devices, Product # R8088)

Cell lines: CHO hGLP1R, CHO hGIPR

Growth media: α-MEM (Gibco, 12561-056) with 10% FBS (Gibco, 10099), 1 mg/ml G418 (invitrogen, 10031035) and 10 nM MTX (sigma, M4010).

Reagents: IBMX (Sigma, 15879); Forskolin (Sigma, F6886); KRB buffer (Sigma, P/N K4002+15 mM $NaHCO_3$); DPBS (GIBCO, REF 14190-136); 3% $H_2O_2$ (Beijing Shiji); DMSO (Sigma, D2650); trypsin (Gibco, 15400); Distilled or deionized water; 96 well plate (Falcon, 353072); native ligands (GLP-1 and GIP) were ordered from Shanghai GL Biochem Ltd.

Equipments: Clean bench (ESCO, SVE-4A1); $CO_2$ incubator (Thermo, 3111); Automated cell counter (Invitrogen, Coutess™); Micropipettes (Eppendorf); Microplate vortex mixer (TAITEC, M.BR-022UP); Microplate reader with fine filters: excitation 530 nM and emission 590 nM (Teacon, infinite F200)

Assay Procedure:

Cell seeding: CHO hGLP1R or CHO hGIPR cells: 10,000 cells/well/100 uL at 37° C. 5% $CO_2$ overnight.

Cell Lysate Preparation:

Gently aspirate off media and wash the cells with KRBG Buffer, 100 uL/well.

Gently aspirate off the KRBG and add 100 uL of 1.5× Stimulation Buffer (0.75 mM IBMX in KRBG Buffer; make fresh on day of experiment). Incubate the plate for 10 min at room temperature. Then add the KRBG buffer with 3× final concentration of the tested samples (5-foled series diluted from 5,000 nM), 50 uL/well. Incubate the plate at 37° C. 5% $CO_2$ for 30 min.

Add 50 uL of Lysis buffer to each well and put the plate on a shaker for 10 min.

cAMP Detection and Data Analysis

Place 40 uL of samples and analyze in appropriate wells. And test the cAMP concentration in each sample by following the manufacture's instruction.

Detect the fluorescence signal at Ex: 490 nm and Em: 530 nm. Transfer the FI signal to cAMP concentration by the cAMP standard curve. The Dose-response curve and $EC_{50}$ were obtained by logistic fitting of Origin 8.

All the synthesized GIP analogs were evaluated in vitro through GLP-1R and GIPR-mediated cAMP-induction assays with the protocol mentioned above, and the $EC_{50}$ values of each peptide were shown in Table 3.

TABLE 3

| | GLP-1 Receptor | | | GIP Receptor | | |
|---|---|---|---|---|---|---|
| Compound | $EC_{50}$ (nM) | Native GLP-1 | Relative Potency | $EC_{50}$ (nM) | Native GIP | Relative Potency |
| GLP-1 | 0.957 | 0.957 | 100 | / | / | / |
| GIP | / | / | / | 0.118 | 0.118 | 100 |
| exendin-4 | 0.725 | 0.957 | 132 | / | / | / |
| liraglutide | 0.315 | 1.359 | 431.4 | / | / | / |

TABLE 3-continued

| Compound | GLP-1 Receptor | | | GIP Receptor | | |
|---|---|---|---|---|---|---|
| | $EC_{50}$ (nM) | Native GLP-1 | Relative Potency | $EC_{50}$ (nM) | Native GIP | Relative Potency |
| 002 | 995 | 1.836 | / | 11.09 | 145 | / |
| 003 | 483 | 0.957 | / | 0.18 | 0.14 | 77.7 |
| 004 | 926 | 11.7 | / | 14.6 | 13.32 | / |
| 005 | >2,000 | 11.7 | / | 76.51 | 13.32 | / |
| 006 | >2,000 | 1.836 | / | 6.66 | 145 | / |
| 007 | 836 | 11.7 | / | 19.04 | 13.32 | / |
| 008 | 1,581 | 11.7 | / | 24.21 | 13.32 | / |
| 009 | >2,000 | 11.7 | / | 22.21 | 13.32 | / |
| 010 | >2,000 | 1.836 | / | 11.52 | 145 | / |
| 011 | 1,477 | 11.7 | / | 693 | 13.32 | / |
| 016 | 1,669 | 11.7 | / | 18.32 | 13.32 | / |
| 020 | 830 | 11.7 | / | 0.27 | 0.14 | 51.8 |
| 021 | 217 | 11.7 | / | 2.3 | 0.5 | 21.7 |
| 023 | 1.276 | 0.957 | 75 | 0.088 | 0.094 | 106.8 |
| 024 | 0.309 | 1.094 | 354 | 0.1 | 0.5 | 500 |
| 025 | 0.837 | 1.094 | 131 | 1.5 | 0.5 | 33.3 |
| 026 | 0.380 | 1.094 | 288 | 4.2 | 0.5 | 11.9 |
| 046 | 6.523 | 0.957 | 14.7 | 1.1 | 0.094 | 8.5 |
| 051 | 0.599 | 0.957 | 159.8 | 0.19 | 0.17 | 89.5 |
| 052-1 | 2.5 | 26.46 | / | 0.57 | 0.21 | 36.8 |
| 052-2 | 0.824 | 1.094 | 132.8 | 0.064 | 0.094 | 146.8 |
| 053-1 | 12.72 | 26.46 | / | 0.5 | 0.17 | 34 |
| 053-2 | 2.955 | 1.094 | 37 | 0.48 | 0.17 | 35.4 |
| 054-1 | 2.99 | 26.46 | / | 0.27 | 0.21 | 77.7 |
| 057 | 4.23 | 26.46 | / | 0.57 | 0.21 | 36.8 |
| 060 | 2.974 | 1.094 | 36.8 | 2.5 | 0.21 | 8.4 |
| 066 | 2.505 | 1.094 | 43.7 | 0.34 | 0.17 | 50 |
| 067 | 7.874 | 1.094 | 13.9 | 3.7 | 0.17 | 4.6 |
| 068 | 0.169 | 0.957 | 566 | 0.037 | 0.118 | 38.9 |
| 071 | 3.803 | 0.957 | 25.1 | 0.77 | 0.17 | 22.1 |
| 074 | 1.055 | 0.957 | 90.7 | 0.43 | 0.17 | 39.5 |
| 075 | 1.407 | 1.094 | 77.7 | 1.45 | 0.12 | 8.3 |
| 078 | 0.145 | 1.094 | 754 | 0.019 | 0.067 | 352.6 |
| 080 | 1.111 | 1.094 | 98.5 | 0.10 | 0.067 | 67 |
| 081 | 0.770 | 0.957 | 124.3 | 0.044 | 0.11 | 250 |
| 084 | 4.799 | 1.069 | 22.2 | 1.338 | 0.118 | 8.8 |
| 088 | 8.723 | 0.957 | 11 | 0.98 | 0.048 | 4.9 |
| 089 | 5.218 | 0.957 | 18.3 | 1.4 | 0.048 | 3.4 |
| 090 | 0.188 | 1.069 | 568.6 | 0.009 | 0.118 | 1311 |
| 091 | 0.116 | 1.069 | 921.5 | 0.041 | 0.118 | 287.8 |
| 092 | 0.39 | 1.00 | 256.4 | 0.15 | 0.04 | 26.6 |
| 093 | 0.43 | 1.00 | 232.5 | 0.03 | 0.04 | 133.3 |
| 094 | 0.67 | 1.00 | 149.2 | 0.85 | 0.04 | 4.7 |
| 096 | 0.253 | 1.024 | 404.7 | 0.100 | 0.042 | 42 |
| 098 | 0.221 | 1.024 | 463.3 | 0.028 | 0.042 | 150 |
| 101 | 0.056 | 0.352 | 628.6 | 0.021 | 0.069 | 328.6 |
| 102 | 0.069 | 0.352 | 510.1 | 0.015 | 0.069 | 460 |
| 105 | 3.94 | 0.46 | 11.7 | 0.4 | 0.06 | 15.0 |
| 106 | 0.922 | 1.455 | 157.8 | 0.097 | 0.065 | 67.0 |
| 116 | 6.650 | 1.102 | 16.6 | 0.045 | 0.242 | 537.8 |
| 117 | 0.569 | 1.102 | 193.7 | 0.301 | 0.242 | 80.4 |
| 120 | 0.253 | 1.484 | 586.6 | 0.039 | 0.115 | 294.9 |
| 127 | 22.761 | 1.172 | 5.1 | 3.058 | 0.047 | 1.5 |
| 128 | 247.211 | 0.969 | 0.39 | 355.466 | / | / |
| 133 | 36.6 | 0.46 | 1.3 | 29.96 | 0.06 | 0.2 |

Example 9

General Protocol for Evaluation in ICR Mice

Animal

Male ICR mice (23-25 g) were obtained from Vital River Laboratories (VRL), Beijing. Animals were cared for in accordance with the principles of the Guide to the Care and Use of Experimental Animals of Beijing Hanmi Pharm Co Ltd. Mice were kept on a 12-h light, 12-h dark cycle. Animals were fed a standard diet which was bought from Ke ao xie li animal food Co Ltd, and had free access to water. Before the experiment, mice were randomly grouped into control group and drugs treated groups.

Materials

Glucose was bought from Tianjin Fuchen chemical reagent factory; Glucometer (ACCU-CHEK® Active) and the blood glucose testing strips were bought form Roche (Shanghai) Co Ltd.

Intraperitoneal Glucose Tolerance Test (ipGTT):

Overnight-fasted mice (16 h) were administered with the sample peptides (up to 1000 nM) or vehicle by subcutaneous injection after blood glucose examination (−30 min) 30 minutes later, 0 min blood glucose was tested. Then 3 g/kg glucose was administered by intraperitoneal injection, and blood glucose was examined at 15, 30, 60 and 120 min after the glucose load. After the glucose test, the data were collected and analyzed. AUC (mmol/L*h)=$(BG_{-30}+BG_0) \times 30/2/60+(BG_0+BG_{15}) \times 15/2/60+(BG_{15}+BG_{30}) \times 15/2/60+$ $(BG_{30}+BG_{60})\times 30/2/60+(BG_{60}+BG_{120})\times 60/2/60$ ($BG_{-30}$, $BG_0$ were 30 minutes and 0 minutes blood glucose before glucose load respectively, and $BG_{15}$, $BG_{30}$, $BG_{60}$ and $BG_{120}$ were 15, 30, 60 and 120 minutes blood glucose after glucose load).

Example 10

General Protocol for Evaluation in Db/Db Mice

Animal

Male BKS.Cg-Dock7$^m$+/+Lepr$^{db}$/J mice (db/db, 6-8 weeks old) were obtained from Model animal research center of Nanjing university. Animals were cared for in accordance with the principles of the Guide to the Care and Use of Experimental Animals of Beijing Hanmi Pharm Co Ltd. Mice were kept on a 12-h light, 12-h dark cycle and were acclimated for 10 days before use Animals were fed a standard diet which was bought from Ke ao xie li animal food Co Ltd, and had free access to water. Before the experiment, mice were randomly grouped into control group and drugs treated groups.

Materials and Methods

Glucose was bought from Tianjin Fuchen chemical reagent factory. Humulin® R was bought from Lilly. Glucometer (ACCU-CHEK® Active) and the blood glucose testing strips were bought form Roche (Shanghai) Co Ltd. Blood cholesterol, triglyceride, high density lipoprotein cholesterol (HDL-c) and low density lipoprotein cholesterol (LDL-c) testing kits were bought from Biosin Bio-technology and Science Inc, Beijing.

Non-Fasting Blood Glucose 0 min blood glucose was tested at 9:30 AM in the morning. Then, mice were administered with the sample peptides (up to 1000 nM) by subcutaneous injection. Blood glucose was tested every 2 hours after drugs administration for 10 hours. And the blood glucose of the last time point was tested 24 hours after drugs administration.

Intraperitoneal Glucose Tolerance Test (ipGTT)

Mice were fasted 12 hours before the experiment. 0 min blood glucose was tested 30 minutes after drugs administration. Then, mice were administered with 1 g/kg dose of glucose by intraperitoneal injection. Blood glucose was tested at 15, 30, 60 and 120 min after glucose load.

Insulin Tolerance Test (ITT)

Mice were fasted 4 hours in the morning, and 0 min blood glucose was tested. After that, 0.4 U/kg Humulin® R was administered by subcutaneous injection, and 15, 30, 60 and 120 min blood glucose was tested.

Blood Lipid Profile Test

Blood cholesterol, triglyceride, high density lipoprotein cholesterol (HDL-c) and low density lipoprotein cholesterol (LDL-c) were tested by using the kits under the manufacture's instruction.

Example 11

General Protocol for Biotin Labeling Anti-GLPHGIP Monoclonal Antibody

Materials

Reagents: biotin labeling kit (Roche Applied Science, 11418165001); anti-GLP1/GIP monoclonal antibody (Cowin Biotech, 20120129).

Equipments: microplate shaker (Thermo Scientific, 4625-1CEQ); spectrophotometer (Shimadzu, UV-2450).

Procedure

Preparation of the solutions:

Blocking solution: Dissolve the contents of the bottle blocking reagent in 300 mL distilled water. Completely dissolve the reagent.

PBS solution: Dissolve the contents of the bottle PBS in 1 liter distilled water. Completely dissolve the reagent.

Biotin-7-NHS solution: The solution must be prepared freshly before labeling. Add 250 uL DMSO to the vial which includes biotin-7-NHS and vortex the solution several times. The resulting concentration of the biotin-7-NHS solution is 20 mg/mL.

Protein labeling with biotin-7-NHS:

Transfer 1 mL of anti-GLP1/GIP antibody solution (1 mg/mL, PBS formulated) to the 1.5 mL EP tube. Dilute 10 uL biotin-7-NHS solution (20 mg/mL) 1:10 with DMSO. Add 15 uL of this biotin-7-NHS solution (2 mg/ml) to the EP tube containing 1 mL of anti-GLP1/GIP antibody solution. Wrap the tube with aluminum foil to protect from light. Incubate the tube on a horizontal orbital microplate shaker set at 500 rpm±50 rpm for 2 hours at room temperature.

Preparation of the Sephadex G-25 column:

While the anti-GLP1/GIP antibody is incubated with biotin-7-NHS, prepare the Sephadex G-25 column Fix the column with a cramp at a stand and place an at least 100 mL containing beaker under the column Open outlet of the column at the bottom with scissors, remove the cap from the top of the column and let the content flow out. Add 5 mL Blocking solution to the column and let run through. Rinse the column afterwards with 30 mL PBS solution in total (5 mL×6 times) and let it flow through. The column should not run dry. The Sehadex G-25 column is now ready to use.

Column chromatography:

Purify the biotin labeled anti-GLP1/GIP antibody from the incubation mixture as followed;

Apply reaction mixture to the column and let it flow though.

Add 1.5 mL PBS solution to the column and let it flow through.

Add additional 3.5 mL of PBS solution to the column for labeled anti-GLP1/GIP antibody elution.

Flow out the first 10 drops.

Collect the second 20 drops to the new 1.5 mL EP tube. This fraction is the biotin labeled anti-GLP1/GIP antibody.

After collection of 20 drops, the Sephadex G-25 column should be discarded.

Concentration determination:

Dilute the labeled protein by 5 fold with PBS solution. (for example, add 20 ul labeled protein to 80 ul PBS solution. The exact volume was in proportion to the volume of crystal cuvette for spectrophotometer.) Measure the optical density at 280 nm. (Plastic cuvette should not be used.) The spectrophotometer should be calibrated with blank using PBS solution.

Determinate the labeled anti-GLP1/GIP antibody concentration (The concentration: O.D. 280 nm/1.35×5 (dilution factor)=X mg/mL). 1.35 is extinction coefficient value of anti-GLP1/GIP antibody.

Example 12

General Protocol for Digoxin Labeling Anti-GLPHGIP Polyclonal Antibody

Materials

Reagents: Digoxigenin-3-O-methylcarbonyl-ε-aminocaproic acid-N-hydroxysuccinimide ester (Roche Applied Science, 11333054001); biotin labeling kit (Roche Applied Science, 11418165001); anti-GLP1/GIP polyclonal antibody (Cowin Biotech, 20111104).

Equipments: microplate shaker (Thermo Scientific, 4625-1CEQ); spectrophotometer (Shimadzu, UV-2450).

Procedure

Preparation of the solutions:

Blocking solution: Dissolve the contents of the bottle blocking reagent in 300 mL distilled water. Completely dissolve the reagent.

PBS solution: Dissolve the contents of the bottle PBS in 1 liter distilled water. Completely dissolve the reagent.

Digoxin-7-NHS solution: Dissolve the Digoxigenin-3-O-methylcarbonyl-ε-aminocaproic acid-N-hydroxysuccinimide ester in 250 uL of DMSO (included in biotin protein labeling kit) and vortex the solution several times. The resulting concentration of the digoxin-NHS solution is 20 mg/mL.

Protein labeling with Digoxin-7-NHS:

Transfer 1 mL of anti-GLP1/GIP antibody (1 mg/mL, PBS formulated) to the 1.5 mL EP tube. Add 11 uL of digoxin-NHS (20 mg/mL) to the EP tube containing 1 mL of anti-GLP1/GIP antibody solution. Wrap the tube with aluminum foil to protect from light. Incubate the tube on a horizontal orbital microplate shaker set at 500 rpm±50 rpm for 2 hours at room temperature.

Preparation of the Sephadex G-25 column:

While the anti-GLP1/GIP antibody is incubated with digoxin-NHS, prepare the Sephadex G-25 column Fix the column with a cramp at a stand and place an at least 100 mL containing beaker under the column Open outlet of the column at the bottom with scissors, remove the cap from the top of the column and let the content flow out. Add 5 mL Blocking solution to the column and let run through. Rinse the column afterwards with 30 mL PBS solution in total (5 mL×6 times) and let it flow through. The column should not run dry. The Sehadex G-25 column is now ready to use.

Column chromatography:

Purify the digoxin labeled anti-GLP1/GIP antibody from the incubation mixture as followed;

Apply reaction mixture to the column and let it flow though.

Add 1.5 mL PBS solution to the column and let it flow through.

Add additional 3.5 mL of PBS solution to the column for labeled anti-GLP1/GIP antibody elution.

Flow out the first 10 drops.

Collect the second 20 drops in the new 1.5 mL EP tube. This fraction is the digoxin labeled anti-GLP1/GIP antibody.

After collection of 20 drops, the Sephadex G-25 column should be discarded

Concentration determination:

Dilute the labeled protein by 5 fold with PBS solution. (for example, add 20 ul labeled protein to 80 ul PBS solution. The exact volume was in proportion to the volume of crystal cuvette for spectrophotometer.) Measure the optical density at 280 nm. (Plastic cuvette should not be used.) The spectrophotometer should be calibrated with blank using PBS solution.

Determinate the labeled anti-GLP1/GIP antibody concentration (The concentration: O.D. 280 nm/1.35×5 (dilution factor)=X mg/mL). 1.35 is extinction coefficient value of anti-GLP1/GIP antibody.

Example 13

PK Study in Mice

Female C57BL/6 mice (23-25 g) were obtained from Vital River Laboratories (VRL), Beijing Animals were cared for in accordance with the principles of the Guide to the Care and Use of Experimental Animals of Beijing Hanmi Pharm Co Ltd. Mice were kept on a 12-h light, 12-h dark cycle. Animals were fed a standard diet which was bought from Ke ao xie li animal food Co Ltd, and had free access to water. These mice were intravenously administered the analogue 089 at the dose of 17 nmol/kg, or subcutaneously administered the analogue 089 at the doses of 17 nmol/kg, 50 nmol/kg and 150 nmol/kg. 0.3 mL blood samples were collected at following time points: 5 min, 15 min, 30 min, 1, 3, 6, 10, 24, 30, 48, 72, 96, 120, 168, 216, 288 h after intravenous administration; 1, 2, 4, 6, 8, 10, 24, 30, 48, 72, 96, 120, 168, 216, 288, 360 h after subcutaneous administration. Blood was collected from orbital venous plexus into the centrifugation tubes containing EDTA. Plasmas were obtained through centrifugation of the blood at 12000 rpm for 5 min Plasmas were stored at −20° C. until analysis. The GIP analogue concentrations in the plasmas were determined by a sandwich ELISA method as the following procedure:

Place streptavidin coated plate (Roche Applied Science, cat#11645692001) to bench in 25° C. from 4° C. to warm up.

Pipette 100 μL of biotinylated anti-GLP1/GIP monoclonal antibody (1 μg/mL) diluted with assay buffer 1 into each well and incubates for 30 min at 25° C.

Wash the plate with wash buffer (300 μL/well) for 5 times.

Pipette 300 μL of blocking buffer into each well and incubates for 1 hr at 25° C.

Wash the plate with wash buffer (300 μL/well) for 5 times.

Pipette 100 μL of calibrators and test samples into each well and incubates for 1 hr at 25° C.

Wash the plate with wash buffer (300 μL/well) for 5 times.

Pipette 100 μL of digoxinylated anti-GLP1/GIP polyclonal antibody (0.5 μg/mL) diluted with assay buffer 2 into each well and incubates for 1 hr at 25° C.

Wash the plate with wash buffer (300 μL/well) for 5 times.

Pipette 100 μL of anti-DIG-POD (75 mU/mL, Roche Applied Science, cat#11633716001) diluted with assay buffer 2 into each well and incubates for 1 hr at 25° C.

Wash the plate with wash buffer (300 μL/well) for 5 times.

Pipette 100 μL of TMB solution (BD biosciences, cat#555214), and colorize the plate for 10 min at 25° C.

Add 100 μL of 1 M H2SO4 solution (Beijing Xingqinghong Jingxi Chemicals Technology Co., Ltd) to stop the colorization.

Determine the optical density of each well within 15 min, using a micro plate reader (BioTek Instruments, ELX-808) set to 450 nm.

SEQUENCE LISTING

<160> NUMBER OF SEQ ID NOS: 109

<210> SEQ ID NO 1

```
<211> LENGTH: 29
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln
            20                  25

<210> SEQ ID NO 2
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 2

Tyr Xaa Glu Gly Thr Phe Thr Ser Asp Tyr Ser Ile Ala Met Glu Lys
1               5                   10                  15

Ile His Gln Gln Asp Phe Val Asn Trp Leu Leu Ala Gln
            20                  25

<210> SEQ ID NO 3
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation
<220> FEATURE:
<221> NAME/KEY: MOD_RES
<222> LOCATION: (29)..(29)
<223> OTHER INFORMATION: amidation

<400> SEQUENCE: 3

Tyr Xaa Glu Gly Thr Phe Thr Ser Asp Tyr Ser Ile Tyr Met Glu Lys
1               5                   10                  15

Ile His Gln Gln Asp Phe Val Asn Trp Leu Leu Ala Gln
            20                  25

<210> SEQ ID NO 4
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = 4-fluoro-Phe
```

```
<220> FEATURE:
<221> NAME/KEY: MISC_FEATURE
<222> LOCATION: (14)..(14)
<223> OTHER INFORMATION: Xaa = Met oxide
<220> FEATURE:
<221> NAME/KEY: MOD_RES
<222> LOCATION: (29)..(29)
<223> OTHER INFORMATION: amidation

<400> SEQUENCE: 4

Tyr Xaa Glu Gly Thr Phe Thr Ser Asp Tyr Ser Ile Xaa Xaa Glu Lys
1               5                   10                  15

Ile His Gln Gln Asp Phe Val Asn Trp Leu Leu Ala Gln
            20                  25

<210> SEQ ID NO 5
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = 4-nitro-Phe
<220> FEATURE:
<221> NAME/KEY: MISC_FEATURE
<222> LOCATION: (14)..(14)
<223> OTHER INFORMATION: Xaa = Met oxide
<220> FEATURE:
<221> NAME/KEY: MOD_RES
<222> LOCATION: (29)..(29)
<223> OTHER INFORMATION: amidation

<400> SEQUENCE: 5

Tyr Xaa Glu Gly Thr Phe Thr Ser Asp Tyr Ser Ile Xaa Xaa Glu Lys
1               5                   10                  15

Ile His Gln Gln Asp Phe Val Asn Trp Leu Leu Ala Gln
            20                  25

<210> SEQ ID NO 6
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Met oxide
<220> FEATURE:
<221> NAME/KEY: MOD_RES
<222> LOCATION: (29)..(29)
<223> OTHER INFORMATION: amidation

<400> SEQUENCE: 6

Tyr Xaa Glu Gly Thr Phe Ile Ser Asp Tyr Ser Ile Ala Xaa Glu Lys
1               5                   10                  15

Ile His Gln Gln Asp Phe Val Asn Trp Leu Leu Ala Gln
            20                  25

<210> SEQ ID NO 7
```

```
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Met oxide
<220> FEATURE:
<221> NAME/KEY: MOD_RES
<222> LOCATION: (29)..(29)
<223> OTHER INFORMATION: amidation

<400> SEQUENCE: 7

Tyr Xaa Glu Gly Thr Phe Thr Ser Asp Tyr Ser Ile Phe Xaa Glu Lys
 1               5                  10                  15

Ile His Gln Gln Asp Phe Val Asn Trp Leu Leu Ala Gln
            20                  25

<210> SEQ ID NO 8
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = 4-nitro-Phe
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 8

Tyr Xaa Glu Gly Thr Phe Thr Ser Asp Tyr Ser Ile Xaa Xaa Glu Lys
 1               5                  10                  15

Ile His Gln Gln Asp Phe Val Asn Trp Leu Leu Ala Gln
            20                  25

<210> SEQ ID NO 9
<211> LENGTH: 29
<212> TYPE: PRT
<213> ORGANISM: Artificial Sequence
<220> FEATURE:
<223> OTHER INFORMATION: GIP analogy
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = phenyl glycine
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
```

```
<222> LOCATION: (29)..(29)
<223> OTHER INFORMATION: amidation

<400> SEQUENCE: 9

Tyr Xaa Glu Gly Thr Phe Thr Ser Asp Tyr Ser Ile Xaa Xaa Glu Lys
1               5                   10                  15

Ile His Gln Gln Asp Phe Val Asn Trp Leu Leu Ala Gln
            20                  25

<210> SEQ ID NO 10
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 10

Tyr Xaa Glu Gly Thr Phe Ile Ser Asp Tyr Ser Ile Ala Xaa Glu Lys
1               5                   10                  15

Ile His Gln Gln Asp Phe Val Asn Trp Leu Leu Ala Gln
            20                  25

<210> SEQ ID NO 11
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 11

Tyr Xaa Glu Gly Thr Phe Thr Ser Asp Tyr Ser Ile Phe Xaa Glu Lys
1               5                   10                  15

Ile His Gln Gln Asp Phe Val Asn Trp Leu Leu Ala Gln
            20                  25

<210> SEQ ID NO 12
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
```

```
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 12

Tyr Xaa Glu Gly Thr Phe Thr Ser Asp Tyr Ser Ile Tyr Xaa Glu Lys
1               5                   10                  15

Ile His Gln Gln Asp Tyr Val Asn Trp Leu Leu Ala Gln
            20                  25

<210> SEQ ID NO 13
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MISC_FEATURE
<222> LOCATION: (22)..(22)
<223> OTHER INFORMATION: Xaa = 4-methyl-Tyr
<220> FEATURE:
<221> NAME/KEY: MOD_RES
<222> LOCATION: (29)..(29)
<223> OTHER INFORMATION: amidation

<400> SEQUENCE: 13

Tyr Xaa Glu Gly Thr Phe Thr Ser Asp Tyr Ser Ile Tyr Xaa Glu Lys
1               5                   10                  15

Ile His Gln Gln Asp Xaa Val Asn Trp Leu Leu Ala Gln
            20                  25

<210> SEQ ID NO 14
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MISC_FEATURE
<222> LOCATION: (22)..(22)
<223> OTHER INFORMATION: Xaa = 4-fluoro-Phe
<220> FEATURE:
<221> NAME/KEY: MOD_RES
<222> LOCATION: (29)..(29)
<223> OTHER INFORMATION: amidation

<400> SEQUENCE: 14

Tyr Xaa Glu Gly Thr Phe Thr Ser Asp Tyr Ser Ile Tyr Xaa Glu Lys
1               5                   10                  15

Ile His Gln Gln Asp Xaa Val Asn Trp Leu Leu Ala Gln
            20                  25
```

```
<210> SEQ ID NO 15
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = 4-nitro-Phe
<220> FEATURE:
<221> NAME/KEY: MOD_RES
<222> LOCATION: (29)..(29)
<223> OTHER INFORMATION: amidation

<400> SEQUENCE: 15

Tyr Xaa Glu Gly Thr Phe Thr Ser Asp Tyr Ser Ile Xaa Met Glu Lys
1               5                   10                  15

Ile His Gln Gln Asp Phe Val Asn Trp Leu Leu Ala Gln
            20                  25

<210> SEQ ID NO 16
<211> LENGTH: 29
<212> TYPE: PRT
<213> ORGANISM: Artificial Sequence
<220> FEATURE:
<223> OTHER INFORMATION: GIP analogg
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 16

Tyr Xaa Glu Gly Thr Phe Thr Ser Asp Tyr Ser Ile Tyr Xaa Glu Lys
1               5                   10                  15

Glu Ala Gln Gln Asp Phe Val Asn Trp Leu Leu Ala Gln
            20                  25

<210> SEQ ID NO 17
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MOD_RES
<222> LOCATION: (29)..(29)
<223> OTHER INFORMATION: amidation

<400> SEQUENCE: 17
```

```
Tyr Xaa Glu Gly Thr Phe Thr Ser Asp Tyr Ser Ile Tyr Xaa Glu Lys
 1               5                  10                  15

Ile His Gln Gln Asp Phe Val Asn Trp Leu Val Arg Gln
            20                  25
```

<210> SEQ ID NO 18
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 18

```
Tyr Xaa Glu Gly Thr Phe Thr Ser Asp Tyr Ser Ile Tyr Met Glu Lys
 1               5                  10                  15

Glu Ala Val Arg Glu Phe Ile Ala Trp Leu Val Lys Gly
            20                  25
```

<210> SEQ ID NO 19
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 19

```
Tyr Xaa Glu Gly Thr Phe Thr Ser Asp Tyr Ser Ile Tyr Met Glu Lys
 1               5                  10                  15

Glu Ala Val Arg Leu Phe Ile Glu Trp Leu Lys Asn Gly
            20                  25
```

<210> SEQ ID NO 20
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 20

```
Tyr Xaa Glu Gly Thr Phe Thr Ser Asp Tyr Ser Ile Tyr Met Glu Lys
 1               5                  10                  15

Gln Ala Ala Lys Glu Phe Ile Ala Trp Leu Val Lys Gly
            20                  25
```

```
<210> SEQ ID NO 21
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 21

Tyr Xaa Glu Gly Thr Phe Thr Ser Asp Tyr Ser Ile Tyr Met Glu Lys
1               5                   10                  15

Gln Ala Ala Lys Leu Phe Ile Glu Trp Leu Lys Asn Gly
            20                  25

<210> SEQ ID NO 22
<211> LENGTH: 30
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (30)..(30)
<223> OTHER INFORMATION: amidation

<400> SEQUENCE: 22

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Cys
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 23

Tyr Xaa Glu Gly Thr Phe Ile Ser Asp Tyr Ser Ile Ala Met Asp Lys
1               5                   10                  15

Ile His Gln Gln Asp Phe Val Cys Trp Leu Leu Ala Gln
            20                  25

<210> SEQ ID NO 24
<211> LENGTH: 29
<212> TYPE: PRT
<213> ORGANISM: Artificial Sequence
<220> FEATURE:
<223> OTHER INFORMATION: GIP analog
<220> FEATURE:
```

```
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 24

Tyr Xaa Glu Gly Thr Phe Thr Ser Asp Tyr Ser Ile Tyr Met Glu Lys
1               5                   10                  15

Glu Ala Ala Gln Asp Phe Val Asn Trp Leu Leu Ala Gln
            20                  25

<210> SEQ ID NO 25
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 25

Tyr Xaa Glu Gly Thr Phe Thr Ser Asp Tyr Ser Ile Tyr Met Glu Lys
1               5                   10                  15

Glu Ala Ile Gln Asp Phe Val Asn Trp Leu Leu Ala Gln
            20                  25

<210> SEQ ID NO 26
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 26

Tyr Xaa Glu Gly Thr Phe Thr Ser Asp Tyr Ser Ile Tyr Met Glu Lys
1               5                   10                  15

Glu Ala Leu Gln Asp Phe Val Asn Trp Leu Leu Ala Gln
            20                  25

<210> SEQ ID NO 27
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (22)..(22)
<223> OTHER INFORMATION: Xaa = 4-chloro-Phe
```

```
<220> FEATURE:
<221> NAME/KEY: MOD_RES
<222> LOCATION: (29)..(29)
<223> OTHER INFORMATION: amidation

<400> SEQUENCE: 27

Tyr Xaa Glu Gly Thr Phe Thr Ser Asp Tyr Ser Ile Tyr Met Glu Lys
1               5                   10                  15

Glu Ala Val Gln Asp Xaa Val Asn Trp Leu Leu Ala Gln
            20                  25

<210> SEQ ID NO 28
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (22)..(22)
<223> OTHER INFORMATION: Xaa = 4-chloro-Phe
<220> FEATURE:
<221> NAME/KEY: MOD_RES
<222> LOCATION: (29)..(29)
<223> OTHER INFORMATION: amidation

<400> SEQUENCE: 28

Tyr Xaa Glu Gly Thr Phe Thr Ser Asp Tyr Ser Ile Tyr Met Glu Lys
1               5                   10                  15

Glu Ala Val Lys Asp Xaa Val Asn Trp Leu Leu Ala Gln
            20                  25

<210> SEQ ID NO 29
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = Pal
<220> FEATURE:
<221> NAME/KEY: MISC_FEATURE
<222> LOCATION: (22)..(22)
<223> OTHER INFORMATION: Xaa = 4-chloro-Phe
<220> FEATURE:
<221> NAME/KEY: MOD_RES
<222> LOCATION: (29)..(29)
<223> OTHER INFORMATION: amidation

<400> SEQUENCE: 29

Tyr Xaa Glu Gly Thr Phe Thr Ser Asp Tyr Ser Ile Xaa Met Glu Lys
1               5                   10                  15

Ile His Gln Gln Asp Xaa Val Asn Trp Leu Leu Ala Gln
            20                  25

<210> SEQ ID NO 30
<211> LENGTH: 29
<212> TYPE: PRT
<213> ORGANISM: Artificial Sequence
<220> FEATURE:
```

-continued

```
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (22)..(22)
<223> OTHER INFORMATION: Xaa = 4-chloro-Phe
<220> FEATURE:
<221> NAME/KEY: MOD_RES
<222> LOCATION: (29)..(29)
<223> OTHER INFORMATION: amidation

<400> SEQUENCE: 30

Tyr Xaa Glu Gly Thr Phe Thr Ser Asp Tyr Ser Ile Tyr Met Glu Lys
1               5                   10                  15

Ile His Gln Lys Asp Xaa Val Asn Trp Leu Leu Ala Gln
            20                  25

<210> SEQ ID NO 31
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (28)..(28)
<223> OTHER INFORMATION: Xaa = Lys(palmitoyl)
<220> FEATURE:
<221> NAME/KEY: MOD_RES
<222> LOCATION: (29)..(29)
<223> OTHER INFORMATION: amidation

<400> SEQUENCE: 31

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Xaa Gly
            20                  25

<210> SEQ ID NO 32
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (28)..(28)
<223> OTHER INFORMATION: Xaa = Lys(palmitoyl)
<220> FEATURE:
<221> NAME/KEY: MOD_RES
<222> LOCATION: (29)..(29)
<223> OTHER INFORMATION: amidation

<400> SEQUENCE: 32

Tyr Xaa Glu Gly Thr Phe Thr Ser Asp Tyr Ser Ile Tyr Met Glu Lys
1               5                   10                  15

Gln Ala Ala Lys Glu Phe Ile Ala Trp Leu Val Xaa Gly
            20                  25
```

-continued

```
<210> SEQ ID NO 33
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (27)..(27)
<223> OTHER INFORMATION: Xaa = Lys(palmitoyl)
<220> FEATURE:
<221> NAME/KEY: MOD_RES
<222> LOCATION: (29)..(29)
<223> OTHER INFORMATION: amidation

<400> SEQUENCE: 33

Tyr Xaa Glu Gly Thr Phe Thr Ser Asp Tyr Ser Ile Tyr Met Glu Lys
1               5                   10                  15

Glu Ala Val Arg Leu Phe Ile Glu Trp Leu Xaa Asn Gly
            20                  25

<210> SEQ ID NO 34
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (27)..(27)
<223> OTHER INFORMATION: Xaa = Lys(palmitoyl)
<220> FEATURE:
<221> NAME/KEY: MOD_RES
<222> LOCATION: (29)..(29)
<223> OTHER INFORMATION: amidation

<400> SEQUENCE: 34

Tyr Xaa Glu Gly Thr Phe Thr Ser Asp Tyr Ser Ile Tyr Met Glu Lys
1               5                   10                  15

Gln Ala Ala Lys Leu Phe Ile Glu Trp Leu Xaa Asn Gly
            20                  25

<210> SEQ ID NO 35
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (39)..(39)
<223> OTHER INFORMATION: amidation

<400> SEQUENCE: 35

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30
```

```
Ser Gly Ala Pro Pro Ser
        35
```

<210> SEQ ID NO 36
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 36

```
Tyr Xaa Glu Gly Thr Phe Thr Ser Asp Tyr Ser Glu Tyr Met Glu Lys
1               5                   10                  15

Glu Ala Val Arg Glu Phe Ile Ala Trp Leu Val Lys Gly
            20                  25
```

<210> SEQ ID NO 37
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (12)..(16)
<223> OTHER INFORMATION: Lactam ring formed between side chains at
      positions 12 and 16
<220> FEATURE:
<221> NAME/KEY: MOD_RES
<222> LOCATION: (29)..(29)
<223> OTHER INFORMATION: amidation

<400> SEQUENCE: 37

```
Tyr Xaa Glu Gly Thr Phe Thr Ser Asp Tyr Ser Glu Tyr Met Glu Lys
1               5                   10                  15

Glu Ala Val Arg Glu Phe Ile Ala Trp Leu Val Lys Gly
            20                  25
```

<210> SEQ ID NO 38
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 38

```
Tyr Xaa Glu Gly Thr Phe Thr Ser Asp Tyr Ser Ile Tyr Met Glu Lys
1               5                   10                  15

Glu Ala Val Glu Glu Phe Ile Ala Trp Leu Val Lys Gly
            20                  25
```

```
<210> SEQ ID NO 39
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(20)
<223> OTHER INFORMATION: lactam ring formed between side chains at
      positions 16 and 20
<220> FEATURE:
<221> NAME/KEY: MOD_RES
<222> LOCATION: (29)..(29)
<223> OTHER INFORMATION: amidation

<400> SEQUENCE: 39

Tyr Xaa Glu Gly Thr Phe Thr Ser Asp Tyr Ser Ile Tyr Met Glu Lys
1               5                   10                  15

Glu Ala Val Glu Glu Phe Ile Ala Trp Leu Val Lys Gly
            20                  25

<210> SEQ ID NO 40
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 40

Tyr Xaa Glu Gly Thr Phe Thr Ser Asp Tyr Ser Ile Tyr Met Glu Lys
1               5                   10                  15

Glu Ala Val Arg Glu Phe Ile Glu Trp Leu Val Lys Gly
            20                  25

<210> SEQ ID NO 41
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 41

Tyr Xaa Glu Gly Thr Phe Thr Ser Asp Tyr Ser Ile Tyr Met Glu Lys
1               5                   10                  15

Glu Ala Ala Arg Glu Phe Ile Ala Trp Leu Val Lys Gly
            20                  25
```

```
<210> SEQ ID NO 42
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (29)..(29)
<223> OTHER INFORMATION: amidation

<400> SEQUENCE: 42

Tyr Xaa Glu Gly Thr Phe Thr Ser Asp Tyr Ser Ile Tyr Met Glu Lys
1               5                   10                  15

Glu Ala Val Lys Glu Phe Ile Ala Trp Leu Val Lys Gly
            20                  25

<210> SEQ ID NO 43
<211> LENGTH: 31
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (31)..(31)
<223> OTHER INFORMATION: amidation

<400> SEQUENCE: 43

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Lys Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (31)..(31)
<223> OTHER INFORMATION: amidation

<400> SEQUENCE: 44

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Arg Gly
            20                  25                  30

<210> SEQ ID NO 45
<211> LENGTH: 34
<212> TYPE: PRT
<213> ORGANISM: Artificial Sequence
<220> FEATURE:
<223> OTHER INFORMATION: GIP analog
<220> FEATURE:
```

```
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (34)..(34)
<223> OTHER INFORMATION: amidation

<400> SEQUENCE: 45

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Lys Lys Lys
            20                  25                  30

Lys Lys

<210> SEQ ID NO 46
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (22)..(22)
<223> OTHER INFORMATION: Xaa = 4-chloro-Phe
<220> FEATURE:
<221> NAME/KEY: MOD_RES
<222> LOCATION: (29)..(29)
<223> OTHER INFORMATION: amidation

<400> SEQUENCE: 46

Tyr Xaa Glu Gly Thr Phe Thr Ser Asp Tyr Ser Ile Tyr Met Glu Lys
1               5                   10                  15

Glu Ala Val Arg Glu Xaa Ile Ala Trp Leu Val Lys Gly
            20                  25

<210> SEQ ID NO 47
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (22)..(22)
<223> OTHER INFORMATION: Xaa = Nal
<220> FEATURE:
<221> NAME/KEY: MOD_RES
<222> LOCATION: (29)..(29)
<223> OTHER INFORMATION: amidation

<400> SEQUENCE: 47

Tyr Xaa Glu Gly Thr Phe Thr Ser Asp Tyr Ser Ile Tyr Met Glu Lys
1               5                   10                  15

Glu Ala Val Arg Glu Xaa Ile Ala Trp Leu Val Lys Gly
            20                  25

<210> SEQ ID NO 48
<211> LENGTH: 29
<212> TYPE: PRT
<213> ORGANISM: Artificial Sequence
```

```
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (13)..(13)
<223> OTHER INFORMATION: Xaa = Pal
<220> FEATURE:
<221> NAME/KEY: MOD_RES
<222> LOCATION: (29)..(29)
<223> OTHER INFORMATION: amidation

<400> SEQUENCE: 48

Tyr Xaa Glu Gly Thr Phe Thr Ser Asp Tyr Ser Ile Xaa Met Glu Lys
1               5                   10                  15

Glu Ala Val Arg Glu Phe Ile Ala Trp Leu Val Lys Gly
            20                  25

<210> SEQ ID NO 49
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (28)..(28)
<223> OTHER INFORMATION: Xaa = Lys-maleimidopropionate
<220> FEATURE:
<221> NAME/KEY: MOD_RES
<222> LOCATION: (29)..(29)
<223> OTHER INFORMATION: amidation

<400> SEQUENCE: 49

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Xaa Gly
            20                  25

<210> SEQ ID NO 50
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 50

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Ser Lys
        35                  40
```

```
<210> SEQ ID NO 51
<211> LENGTH: 29
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Xaa = Lys(palmitoyl)
<220> FEATURE:
<221> NAME/KEY: MOD_RES
<222> LOCATION: (29)..(29)
<223> OTHER INFORMATION: amidation

<400> SEQUENCE: 51

Tyr Xaa Glu Gly Thr Phe Thr Ser Asp Tyr Ser Ile Tyr Met Glu Lys
1               5                   10                  15

Glu Ala Val Xaa Glu Phe Ile Ala Trp Leu Val Lys Gly
            20                  25

<210> SEQ ID NO 52
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 52

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 53
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys-maleimidopropionate
<220> FEATURE:
<221> NAME/KEY: MOD_RES
<222> LOCATION: (40)..(40)
<223> OTHER INFORMATION: amidation

<400> SEQUENCE: 53
```

```
Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40
```

<210> SEQ ID NO 54
<211> LENGTH: 45
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (45)..(45)
<223> OTHER INFORMATION: amidation

<400> SEQUENCE: 54

```
Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Lys Lys Lys Lys Lys
        35                  40                  45
```

<210> SEQ ID NO 55
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(biotin)
<220> FEATURE:
<221> NAME/KEY: MOD_RES
<222> LOCATION: (40)..(40)
<223> OTHER INFORMATION: amidation

<400> SEQUENCE: 55

```
Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40
```

<210> SEQ ID NO 56
<211> LENGTH: 35
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib

```
<220> FEATURE:
<221> NAME/KEY: MOD_RES
<222> LOCATION: (35)..(35)
<223> OTHER INFORMATION: amidation

<400> SEQUENCE: 56

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Arg Arg Arg
            20                  25                  30

Arg Arg Arg
        35

<210> SEQ ID NO 57
<211> LENGTH: 45
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (45)..(45)
<223> OTHER INFORMATION: Xaa = Lys(palmitoyl)
<220> FEATURE:
<221> NAME/KEY: MOD_RES
<222> LOCATION: (45)..(45)
<223> OTHER INFORMATION: amidation

<400> SEQUENCE: 57

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Lys Lys Lys Lys Lys Xaa
        35                  40                  45

<210> SEQ ID NO 58
<211> LENGTH: 45
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (45)..(45)
<223> OTHER INFORMATION: Xaa = Lus-maleimidopropionate
<220> FEATURE:
<221> NAME/KEY: MOD_RES
<222> LOCATION: (45)..(45)
<223> OTHER INFORMATION: amidation

<400> SEQUENCE: 58

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Lys Lys Lys Lys Lys Lys
        35                  40                  45
```

```
<210> SEQ ID NO 59
<211> LENGTH: 45
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (45)..(45)
<223> OTHER INFORMATION: Xaa = Lys(biotin)
<220> FEATURE:
<221> NAME/KEY: MOD_RES
<222> LOCATION: (45)..(45)
<223> OTHER INFORMATION: amidation

<400> SEQUENCE: 59

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Lys Lys Lys Lys Lys Xaa
        35                  40                  45

<210> SEQ ID NO 60
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (12)..(16)
<223> OTHER INFORMATION: Lactam ring formed between side chains at
      positions 12 and 16
<220> FEATURE:
<221> NAME/KEY: MOD_RES
<222> LOCATION: (39)..(39)
<223> OTHER INFORMATION: amidation

<400> SEQUENCE: 60

Tyr Xaa Glu Gly Thr Phe Thr Ser Asp Tyr Ser Glu Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser
        35

<210> SEQ ID NO 61
<211> LENGTH: 30
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (12)..(16)
<223> OTHER INFORMATION: Lactam ring formed between side chains at
      positions 12 and 16
<220> FEATURE:
```

<221> NAME/KEY: MISC_FEATURE
<222> LOCATION: (30)..(30)
<223> OTHER INFORMATION: Xaa = Lys(palmitoyl)
<220> FEATURE:
<221> NAME/KEY: MOD_RES
<222> LOCATION: (30)..(30)
<223> OTHER INFORMATION: amidation

<400> SEQUENCE: 61

Tyr Xaa Glu Gly Thr Phe Thr Ser Asp Tyr Ser Glu Tyr Met Glu Lys
1               5                   10                  15

Glu Ala Val Arg Glu Phe Ile Ala Trp Leu Val Lys Gly Xaa
            20                  25                  30

<210> SEQ ID NO 62
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(24)
<223> OTHER INFORMATION: Lactam ring formed between side chains at
      positions  20 and 24
<220> FEATURE:
<221> NAME/KEY: MOD_RES
<222> LOCATION: (39)..(39)
<223> OTHER INFORMATION: amidation

<400> SEQUENCE: 62

Tyr Xaa Glu Gly Thr Phe Thr Ser Asp Tyr Ser Ile Tyr Met Glu Lys
1               5                   10                  15

Glu Ala Val Lys Glu Phe Ile Glu Trp Leu Val Lys Gly Gly Pro Ser
            20                  25                  30

Ser Gly Ala Pro Pro Pro Ser
        35

<210> SEQ ID NO 63
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 63

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Cys
        35                  40

<210> SEQ ID NO 64
<211> LENGTH: 40
<212> TYPE: PRT

<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(20kDa PEG)
<220> FEATURE:
<221> NAME/KEY: MOD_RES
<222> LOCATION: (40)..(40)
<223> OTHER INFORMATION: amidation

<400> SEQUENCE: 64

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 65
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(40kDa PEG)
<220> FEATURE:
<221> NAME/KEY: MOD_RES
<222> LOCATION: (40)..(40)
<223> OTHER INFORMATION: amidation

<400> SEQUENCE: 65

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 66
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys-(gamma-Glu-palmitoyl)
<220> FEATURE:
<221> NAME/KEY: MOD_RES
<222> LOCATION: (40)..(40)
<223> OTHER INFORMATION: amidation

<400> SEQUENCE: 66

```
Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 67
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys-(gamma-Glu-gamma-Glu-palmitoyl)
<220> FEATURE:
<221> NAME/KEY: MOD_RES
<222> LOCATION: (40)..(40)
<223> OTHER INFORMATION: amidation

<400> SEQUENCE: 67

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 68
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Xaa = Lys-(gamma-Glu-palmitoyl)
<220> FEATURE:
<221> NAME/KEY: MOD_RES
<222> LOCATION: (39)..(39)
<223> OTHER INFORMATION: amidation

<400> SEQUENCE: 68

Tyr Xaa Glu Gly Thr Phe Thr Ser Asp Tyr Ser Ile Tyr Met Glu Lys
1               5                   10                  15

Glu Ala Val Xaa Glu Phe Ile Ala Trp Leu Val Lys Gly Gly Pro Ser
            20                  25                  30

Ser Gly Ala Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: GIP analog
```

-continued

```
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(20)
<223> OTHER INFORMATION: Xaa = Lys-(gamma-Glu-gamma-Glu-palmitoyl)
<220> FEATURE:
<221> NAME/KEY: MOD_RES
<222> LOCATION: (39)..(39)
<223> OTHER INFORMATION: amidation

<400> SEQUENCE: 69

Tyr Xaa Glu Gly Thr Phe Thr Ser Asp Tyr Ser Ile Tyr Met Glu Lys
 1               5                  10                  15

Glu Ala Val Xaa Glu Phe Ile Ala Trp Leu Val Lys Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (28)..(28)
<223> OTHER INFORMATION: Xaa = Lys-(gamma-Glu-palmitoyl)
<220> FEATURE:
<221> NAME/KEY: MOD_RES
<222> LOCATION: (39)..(39)
<223> OTHER INFORMATION: amidation

<400> SEQUENCE: 70

Tyr Xaa Glu Gly Thr Phe Thr Ser Asp Tyr Ser Ile Tyr Met Glu Lys
 1               5                  10                  15

Glu Ala Val Arg Glu Phe Ile Ala Trp Leu Val Xaa Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (28)..(28)
<223> OTHER INFORMATION: Xaa = Lys-(gamma-Glu-gamma-Glu-palmitoyl)
<220> FEATURE:
<221> NAME/KEY: MOD_RES
<222> LOCATION: (39)..(39)
<223> OTHER INFORMATION: amidation

<400> SEQUENCE: 71

Tyr Xaa Glu Gly Thr Phe Thr Ser Asp Tyr Ser Ile Tyr Met Glu Lys
 1               5                  10                  15
```

```
Glu Ala Val Arg Glu Phe Ile Ala Trp Leu Val Xaa Gly Gly Pro Ser
            20                  25                  30

Ser Gly Ala Pro Pro Ser
        35

<210> SEQ ID NO 72
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 72

Tyr Xaa Glu Gly Thr Phe Thr Ser Asp Tyr Ser Ile Tyr Met Glu Lys
1               5                   10                  15

Glu Ala Val Arg Glu Phe Ile Cys Trp Leu Val Lys Gly Gly Pro Ser
            20                  25                  30

Ser Gly Ala Pro Pro Ser Xaa
        35                  40

<210> SEQ ID NO 73
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (24)..(24)
<223> OTHER INFORMATION: Xaa = Cys(20kDa PEG)
<220> FEATURE:
<221> NAME/KEY: MISC_FEATURE
<222> LOCATION: (40)..(40)
<223> OTHER INFORMATION: Xaa = Lys(palmitoyl)

<400> SEQUENCE: 73

Tyr Xaa Glu Gly Thr Phe Thr Ser Asp Tyr Ser Ile Tyr Met Glu Lys
1               5                   10                  15

Glu Ala Val Arg Glu Phe Ile Xaa Trp Leu Val Lys Gly Gly Pro Ser
            20                  25                  30

Ser Gly Ala Pro Pro Ser Xaa
        35                  40

<210> SEQ ID NO 74
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
```

```
<223> OTHER INFORMATION: Xaa = Aib
<220> FEATURE:
<221> NAME/KEY: MISC_FEATURE
<222> LOCATION: (24)..(24)
<223> OTHER INFORMATION: Xaa = Cys(40kDa PEG)
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 74

Tyr Xaa Glu Gly Thr Phe Thr Ser Asp Tyr Ser Ile Tyr Met Glu Lys
1               5                   10                  15

Glu Ala Val Arg Glu Phe Ile Xaa Trp Leu Val Lys Gly Gly Pro Ser
            20                  25                  30

Ser Gly Ala Pro Pro Pro Ser Xaa
        35                  40

<210> SEQ ID NO 75
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (12)..(16)
<223> OTHER INFORMATION: Lactam ring formed between side chains at
      positions 12 and 16
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 75

Tyr Xaa Glu Gly Thr Phe Thr Ser Asp Tyr Ser Glu Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 76
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(20)
<223> OTHER INFORMATION: Lactam ring formed between side chains at
      positions 16 and 20
<220> FEATURE:
<221> NAME/KEY: MISC_FEATURE
```

<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 76

Tyr Xaa Glu Gly Thr Phe Thr Ser Asp Tyr Ser Ile Tyr Met Glu Lys
1               5                   10                  15

Glu Ala Val Glu Glu Phe Ile Ala Trp Leu Val Lys Gly Gly Pro Ser
            20                  25                  30

Ser Gly Ala Pro Pro Pro Ser Xaa
        35                  40

<210> SEQ ID NO 77
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (20)..(24)
<223> OTHER INFORMATION: Lactam ring formed between side chains at
     positions 20 and 24
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 77

Tyr Xaa Glu Gly Thr Phe Thr Ser Asp Tyr Ser Ile Tyr Met Glu Lys
1               5                   10                  15

Glu Ala Val Lys Glu Phe Ile Glu Trp Leu Val Lys Gly Gly Pro Ser
            20                  25                  30

Ser Gly Ala Pro Pro Pro Ser Xaa
        35                  40

<210> SEQ ID NO 78
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (24)..(28)
<223> OTHER INFORMATION: Lactam ring formed between side chains at
     positions 24 and 28
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation -continued

<400> SEQUENCE: 78

Tyr Xaa Glu Gly Thr Phe Thr Ser Asp Tyr Ser Ile Tyr Met Glu Lys
1               5                   10                  15

Glu Ala Val Lys Glu Phe Ile Glu Trp Leu Val Lys Gly Gly Pro Ser
            20                  25                  30

Ser Gly Ala Pro Pro Pro Ser Xaa
        35                  40

<210> SEQ ID NO 79
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Nle
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 79

Tyr Xaa Glu Gly Thr Phe Thr Ser Asp Tyr Ser Ile Tyr Xaa Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 80
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 80

Tyr Xaa Glu Gly Thr Phe Thr Ser Asp Tyr Ser Ile Tyr Met Glu Lys
1               5                   10                  15

Glu Ala Val Arg Glu Phe Ile Cys Trp Leu Val Lys Gly Gly Pro Ser
            20                  25                  30

Ser Gly Ala Pro Pro Pro Ser Lys
        35                  40

<210> SEQ ID NO 81
<211> LENGTH: 40
<212> TYPE: PRT
<213> ORGANISM: Artificial Sequence
<220> FEATURE:

```
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(hexadecanedioic acyl)
<220> FEATURE:
<221> NAME/KEY: MOD_RES
<222> LOCATION: (40)..(40)
<223> OTHER INFORMATION: amidation

<400> SEQUENCE: 81

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 82
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (39)..(39)
<223> OTHER INFORMATION: amidation

<400> SEQUENCE: 82

Tyr Xaa Glu Gly Thr Phe Thr Ser Asp Tyr Ser Ile Tyr Met Glu Lys
1               5                   10                  15

Glu Ala Val Arg Glu Phe Ile Cys Trp Leu Val Lys Gly Gly Pro Ser
            20                  25                  30

Ser Gly Ala Pro Pro Pro Ser
        35

<210> SEQ ID NO 83
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (39)..(39)
<223> OTHER INFORMATION: Xaa = Ser (cholic acyl)
<220> FEATURE:
<221> NAME/KEY: MOD_RES
<222> LOCATION: (39)..(39)
<223> OTHER INFORMATION: amidation

<400> SEQUENCE: 83

Tyr Xaa Glu Gly Thr Phe Thr Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30
```

Ser Gly Ala Pro Pro Pro Xaa
        35

<210> SEQ ID NO 84
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (39)..(39)
<223> OTHER INFORMATION: Xaa = Lys(palmitoyl)
<220> FEATURE:
<221> NAME/KEY: MOD_RES
<222> LOCATION: (39)..(39)
<223> OTHER INFORMATION: amidation

<400> SEQUENCE: 84

Tyr Xaa Glu Gly Thr Phe Ile Ser Asp Tyr Ser Ile Tyr Met Glu Lys
1               5                   10                  15

Glu Ala Val Arg Glu Phe Ile Cys Trp Leu Val Lys Gly Gly Pro Ser
            20                  25                  30

Ser Gly Ala Pro Pro Pro Xaa
        35

<210> SEQ ID NO 85
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (39)..(39)
<223> OTHER INFORMATION: Xaa = Lys(palmitoyl)
<220> FEATURE:
<221> NAME/KEY: MOD_RES
<222> LOCATION: (39)..(39)
<223> OTHER INFORMATION: amidation

<400> SEQUENCE: 85

Tyr Xaa Glu Gly Thr Phe Ser Ser Asp Tyr Ser Ile Tyr Met Glu Lys
1               5                   10                  15

Glu Ala Val Arg Glu Phe Ile Cys Trp Leu Val Lys Gly Gly Pro Ser
            20                  25                  30

Ser Gly Ala Pro Pro Pro Xaa
        35

<210> SEQ ID NO 86
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (24)..(24)
<223> OTHER INFORMATION: Xaa = Cys(40kDa PEG)
<220> FEATURE:
<221> NAME/KEY: MISC_FEATURE
<222> LOCATION: (39)..(39)
<223> OTHER INFORMATION: Xaa = Lys(palmitoyl)
<220> FEATURE:
<221> NAME/KEY: MOD_RES
<222> LOCATION: (39)..(39)
<223> OTHER INFORMATION: amidation

<400> SEQUENCE: 86

Tyr Xaa Glu Gly Thr Phe Ile Ser Asp Tyr Ser Ile Tyr Met Glu Lys
1               5                   10                  15

Glu Ala Val Arg Glu Phe Ile Xaa Trp Leu Val Lys Gly Gly Pro Ser
            20                  25                  30

Ser Gly Ala Pro Pro Pro Xaa
            35

<210> SEQ ID NO 87
<211> LENGTH: 39
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (24)..(24)
<223> OTHER INFORMATION: Xaa = Cys(40kDa PEG)
<220> FEATURE:
<221> NAME/KEY: MISC_FEATURE
<222> LOCATION: (39)..(39)
<223> OTHER INFORMATION: Xaa = Lys(palmitoyl)
<220> FEATURE:
<221> NAME/KEY: MOD_RES
<222> LOCATION: (39)..(39)
<223> OTHER INFORMATION: amidation

<400> SEQUENCE: 87

Tyr Xaa Glu Gly Thr Phe Ser Ser Asp Tyr Ser Ile Tyr Met Glu Lys
1               5                   10                  15

Glu Ala Val Arg Glu Phe Ile Xaa Trp Leu Val Lys Gly Gly Pro Ser
            20                  25                  30

Ser Gly Ala Pro Pro Pro Xaa
            35

<210> SEQ ID NO 88
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(palmitoyl)
<220> FEATURE:
<221> NAME/KEY: MOD_RES
<222> LOCATION: (40)..(40)
<223> OTHER INFORMATION: amidation

<400> SEQUENCE: 88

```
Tyr Xaa Gln Gly Thr Phe Thr Ser Asp Tyr Ser Ile Tyr Met Glu Lys
 1               5                  10                  15

Glu Ala Val Arg Glu Phe Ile Ala Trp Leu Val Lys Gly Gly Pro Ser
             20                  25                  30

Ser Gly Ala Pro Pro Pro Ser Xaa
         35                  40
```

<210> SEQ ID NO 89
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 89

```
Tyr Xaa Glu Gly Thr Phe Ile Ser Asp Tyr Ser Ile Tyr Met Glu Lys
 1               5                  10                  15

Glu Ala Val Arg Glu Phe Ile Ala Trp Leu Val Lys Gly Gly Pro Ser
             20                  25                  30

Ser Gly Ala Pro Pro Pro Ser Cys
         35                  40
```

<210> SEQ ID NO 90
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 90

```
Tyr Xaa Glu Gly Thr Phe Ser Ser Asp Tyr Ser Ile Tyr Met Glu Lys
 1               5                  10                  15

Glu Ala Val Arg Glu Phe Ile Ala Trp Leu Val Lys Gly Gly Pro Ser
             20                  25                  30

Ser Gly Ala Pro Pro Pro Ser Cys
         35                  40
```

<210> SEQ ID NO 91
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(40kDa PEG)
<220> FEATURE:

```
<221> NAME/KEY: MOD_RES
<222> LOCATION: (40)..(40)
<223> OTHER INFORMATION: amidation

<400> SEQUENCE: 91

Tyr Xaa Glu Gly Thr Phe Ile Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 92
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(40k PEG)
<220> FEATURE:
<221> NAME/KEY: MOD_RES
<222> LOCATION: (40)..(40)
<223> OTHER INFORMATION: amidation

<400> SEQUENCE: 92

Tyr Xaa Glu Gly Thr Phe Ser Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 93
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MOD_RES
<222> LOCATION: (40)..(40)
<223> OTHER INFORMATION: amidation

<400> SEQUENCE: 93

Tyr Xaa Gln Gly Thr Phe Ser Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Cys
        35                  40

<210> SEQ ID NO 94
<211> LENGTH: 40
<212> TYPE: PRT
<213> ORGANISM: Artificial Sequence
<220> FEATURE:
```

<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(40kDa PEG)
<220> FEATURE:
<221> NAME/KEY: MOD_RES
<222> LOCATION: (40)..(40)
<223> OTHER INFORMATION: amidation

<400> SEQUENCE: 94

Tyr Xaa Gln Gly Thr Phe Ser Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 95
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Lys(40kDa PEG)
<220> FEATURE:
<221> NAME/KEY: MOD_RES
<222> LOCATION: (40)..(40)
<223> OTHER INFORMATION: amidation

<400> SEQUENCE: 95

Tyr Xaa Glu Gly Thr Phe Ser Ser Asp Tyr Ser Ile Tyr Met Glu Lys
1               5                   10                  15

Glu Ala Val Arg Glu Phe Ile Ala Trp Leu Val Lys Gly Gly Pro Ser
            20                  25                  30

Ser Gly Ala Pro Pro Pro Ser Xaa
        35                  40

<210> SEQ ID NO 96
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (40)..(40)
<223> OTHER INFORMATION: Xaa = Cys(palmitoyl)
<220> FEATURE:
<221> NAME/KEY: MOD_RES
<222> LOCATION: (40)..(40)
<223> OTHER INFORMATION: amidation

<400> SEQUENCE: 96

Tyr Xaa Glu Gly Thr Phe Ser Ser Asp Tyr Ser Ile Tyr Met Glu Lys

```
                1               5                   10                  15
Glu Ala Val Arg Glu Phe Ile Ala Trp Leu Val Lys Gly Gly Pro Ser
                20                  25                  30

Ser Gly Ala Pro Pro Pro Ser Xaa
        35                  40

<210> SEQ ID NO 97
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Lys(Biontin)
<220> FEATURE:
<221> NAME/KEY: MISC_FEATURE
<222> LOCATION: (28)..(28)
<223> OTHER INFORMATION: Xaa = Lys(Biontin)
<220> FEATURE:
<221> NAME/KEY: MOD_RES
<222> LOCATION: (40)..(40)
<223> OTHER INFORMATION: amidation

<400> SEQUENCE: 97

Tyr Xaa Glu Gly Thr Phe Ser Ser Asp Tyr Ser Ile Tyr Met Glu Xaa
1               5                   10                  15

Glu Ala Val Arg Glu Phe Ile Ala Trp Leu Val Xaa Gly Gly Pro Ser
                20                  25                  30

Ser Gly Ala Pro Pro Pro Ser Lys
        35                  40

<210> SEQ ID NO 98
<211> LENGTH: 40
<212> TYPE: PRT
<213> ORGANISM: Artificial Sequence
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (24)..(24)
<223> OTHER INFORMATION: Xaa = Cys(40kDa PEG)
<220> FEATURE:
<221> NAME/KEY: MOD_RES
<222> LOCATION: (40)..(40)
<223> OTHER INFORMATION: amidation

<400> SEQUENCE: 98

Tyr Xaa Glu Gly Thr Phe Ser Ser Asp Tyr Ser Ile Tyr Met Glu Lys
1               5                   10                  15

Glu Ala Val Arg Glu Phe Ile Xaa Trp Leu Val Lys Gly Gly Pro Ser
                20                  25                  30

Ser Gly Ala Pro Pro Pro Ser Lys
        35                  40

<210> SEQ ID NO 99
<211> LENGTH: 39
<212> TYPE: PRT
<213> ORGANISM: Homo sapiens
```

<400> SEQUENCE: 99

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 100
<211> LENGTH: 30
<212> TYPE: PRT
<213> ORGANISM: Homo sapiens

<400> SEQUENCE: 100

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 101
<211> LENGTH: 10
<212> TYPE: PRT
<213> ORGANISM: Artificial
<220> FEATURE:
<223> OTHER INFORMATION: a fragment of exendin-4 (30-39)

<400> SEQUENCE: 101

Gly Pro Ser Ser Gly Ala Pro Pro Pro Ser
1               5                   10

<210> SEQ ID NO 102
<211> LENGTH: 8
<212> TYPE: PRT
<213> ORGANISM: Artificial
<220> FEATURE:
<223> OTHER INFORMATION: intervening peptide (IP-1 fragment)

<400> SEQUENCE: 102

Lys Arg Asn Arg Asn Asn Ile Ala
1               5

<210> SEQ ID NO 103
<211> LENGTH: 29
<212> TYPE: PRT
<213> ORGANISM: Artificial
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa is selected from the group consisting of
      Ala, Gly, Sarcosine, Aib, d-Ala and d-Ser
<220> FEATURE:
<221> NAME/KEY: MISC_FEATURE
<222> LOCATION: (3)..(3)
<223> OTHER INFORMATION: Xaa is selected from the group consisting of
      Glu and Gln
<220> FEATURE:
<221> NAME/KEY: MISC_FEATURE
<222> LOCATION: (7)..(7)
<223> OTHER INFORMATION: Xaa is selected from the group consisting of
      Thr, Ile and Ser
<220> FEATURE:
<221> NAME/KEY: MISC_FEATURE
<222> LOCATION: (12)..(12)
<223> OTHER INFORMATION: Xaa is selected from the group consisting of
      Ile, Glu and Asp

```
<220> FEATURE:
<221> NAME/KEY: MISC_FEATURE
<222> LOCATION: (12)..(28)
<223> OTHER INFORMATION: a lactam linkage is optionally formed between
      the amino acids at positions i and i+4 of the GIP analog; i is an
      integer selected from 12 to 24
<220> FEATURE:
<221> NAME/KEY: MISC_FEATURE
<222> LOCATION: (13)..(13)
<223> OTHER INFORMATION: Xaa is selected from the group consisting of an
      amino acid residue having aryl group and is selected from Tyr,
      Phe, Phe(4-F), Phe(4-NO2), Phe(4-NH2), Ala, Ala(2-thienyl),
      Ala(benzothienyl), Ala(4-Pyridyl) and phenylglycine
<220> FEATURE:
<221> NAME/KEY: MISC_FEATURE
<222> LOCATION: (14)..(14)
<223> OTHER INFORMATION: Xaa is selected from the group consisting of
      Met or oxidized Met, Leu, Val, Norleucine and Ile
<220> FEATURE:
<221> NAME/KEY: MISC_FEATURE
<222> LOCATION: (15)..(15)
<223> OTHER INFORMATION: Xaa is selected from the group consisting of
      Glu and Asp
<220> FEATURE:
<221> NAME/KEY: MISC_FEATURE
<222> LOCATION: (17)..(17)
<223> OTHER INFORMATION: Xaa is selected from the group consisting of
      Ile, Glu, and Gln
<220> FEATURE:
<221> NAME/KEY: MISC_FEATURE
<222> LOCATION: (18)..(18)
<223> OTHER INFORMATION: Xaa is selected from the group consisting of
      Ala and His
<220> FEATURE:
<221> NAME/KEY: MISC_FEATURE
<222> LOCATION: (19)..(19)
<223> OTHER INFORMATION: Xaa is selected from the group consisting of
      Val, Ala, Leu, Gln and Ile
<220> FEATURE:
<221> NAME/KEY: MISC_FEATURE
<222> LOCATION: (20)..(20)
<223> OTHER INFORMATION: Xaa is selected from the group consisting of
      Arg, Lys-Z, Gln, Glu, Asp and Cys-Z, wherein Z is selected from
      the group consisting of -(Glu)m-PEG, -(Glu)m-biotin and
      -(Glu)m-fatty acid, or absent and m is an integer selected from
      0 to 3.
<220> FEATURE:
<221> NAME/KEY: MISC_FEATURE
<222> LOCATION: (21)..(21)
<223> OTHER INFORMATION: Xaa is selected from the group consisting of
      Glu, Asp and Leu
<220> FEATURE:
<221> NAME/KEY: MISC_FEATURE
<222> LOCATION: (22)..(22)
<223> OTHER INFORMATION: Xaa is selected from the group consisting of
      Phe, Phe(4-F), Phe(4-Cl), Tyr, Tyr(4-Me) and Nal
<220> FEATURE:
<221> NAME/KEY: MISC_FEATURE
<222> LOCATION: (23)..(23)
<223> OTHER INFORMATION: Xaa is selected from the group consisting of
      Ile and Val
<220> FEATURE:
<221> NAME/KEY: MISC_FEATURE
<222> LOCATION: (24)..(24)
<223> OTHER INFORMATION: Xaa is selected from the group consisting of
      Ala, Asn, Glu, Lys-Z and Cys-Z, wherein Z is selected from the
      group consisting of -(Glu)m-PEG, -(Glu)m-biotin and
      -(Glu)m-fatty acid, or absent and m is an integer selected from
      0 to 3.
<220> FEATURE:
<221> NAME/KEY: MISC_FEATURE
<222> LOCATION: (27)..(27)
<223> OTHER INFORMATION: Xaa is selected from the group consisting of
      Val, Leu, Ala, and Lys-Z, wherein Z is selected from the group
      consisting of -(Glu)m-PEG, -(Glu)m-biotin and -(Glu)m-fatty acid,
      or absent and m is an integer selected from 0 to 3.
<220> FEATURE:
<221> NAME/KEY: MISC_FEATURE
<222> LOCATION: (28)..(28)
```

```
<223> OTHER INFORMATION: Xaa is selected from the group consisting of
      Lys-Z, Ala, Arg, and Asn, wherein Z is selected from the group
      consisting of -(Glu)m-PEG, -(Glu)m-biotin and -(Glu)m-fatty acid,
      or absent and m is an integer selected from 0 to 3.
<220> FEATURE:
<221> NAME/KEY: MISC_FEATURE
<222> LOCATION: (29)..(29)
<223> OTHER INFORMATION: Xaa is selected from the group consisting of
      Gly, Gln and Arg
<220> FEATURE:
<221> NAME/KEY: MISC_FEATURE
<222> LOCATION: (29)..(29)
<223> OTHER INFORMATION: Xaa is linked with a Y, wherein Y is selected
      from the group consisting of: A30 and
      -Gly-Pro-Ser-Ser-Gly-Ala-Pro-Pro-Pro-Ser-A40, or
      absent;A30 and A40 are independently selected from the group
      consisting of -(Lys)n-Z and -Cys-Z, or absent;Z is selected from
      the group consisting of -(Glu)m-PEG, -(Glu)m-biotin and
      -(Glu)m-fatty acid, or absent;n is an integer selected from 1 to
      6;m is an integer selected from 0 to 3

<400> SEQUENCE: 103

Tyr Xaa Xaa Gly Thr Phe Xaa Ser Asp Tyr Ser Xaa Xaa Xaa Xaa Lys
1               5                   10                  15

Xaa Xaa Xaa Xaa Xaa Xaa Xaa Xaa Trp Leu Xaa Xaa Xaa
            20                  25

<210> SEQ ID NO 104
<211> LENGTH: 10
<212> TYPE: PRT
<213> ORGANISM: Artificial
<220> FEATURE:
<223> OTHER INFORMATION: peptide fragment
<220> FEATURE:
<221> NAME/KEY: MISC_FEATURE
<222> LOCATION: (10)..(10)
<223> OTHER INFORMATION: Xaa is linked with A40, wherein A40 is selected
      from the group consisting of -(Lys)n-Z and -Cys-Z, or absent;Z
      is selected from the group consisting of -(Glu)m-PEG,
      -(Glu)m-biotin and -(Glu)m-fatty acid, or absent;n is an integer
      selected from 1 to 6;m is an integer selected from 0 to 3

<400> SEQUENCE: 104

Gly Pro Ser Ser Gly Ala Pro Pro Pro Ser
1               5                   10

<210> SEQ ID NO 105
<211> LENGTH: 29
<212> TYPE: PRT
<213> ORGANISM: Artificial
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa is selected from the group consisting of
      Ala, Gly, Sarcosine, Aib, d-Ala and d-Ser
<220> FEATURE:
<221> NAME/KEY: MISC_FEATURE
<222> LOCATION: (7)..(7)
<223> OTHER INFORMATION: Xaa is selected from the group consisting
      of Thr, Ile and Ser
<220> FEATURE:
<221> NAME/KEY: MISC_FEATURE
<222> LOCATION: (12)..(12)
<223> OTHER INFORMATION: Xaa is selected from the group consisting
      of Ile, Glu and Asp
<220> FEATURE:
<221> NAME/KEY: MISC_FEATURE
<222> LOCATION: (12)..(28)
<223> OTHER INFORMATION: a lactam linkage is optionally formed between
      the amino acids at positions i and i+4 of the GIP analog; i is an
      integer selected from 12 to 24
<220> FEATURE:
```

```
<221> NAME/KEY: MISC_FEATURE
<222> LOCATION: (13)..(13)
<223> OTHER INFORMATION: Xaa is selected from the group consisting of
      an amino acid residue having aryl group and is selected from Tyr,
      Phe, Phe(4-F), Phe(4-NO2), Phe(4-NH2), Ala(2-thienyl),
      Ala(benzothienyl) and phenylglycine
<220> FEATURE:
<221> NAME/KEY: MISC_FEATURE
<222> LOCATION: (14)..(14)
<223> OTHER INFORMATION: Xaa is selected from the group consisting of
      Met or oxidized Met, Leu, Val, Norleucine and Ile
<220> FEATURE:
<221> NAME/KEY: MISC_FEATURE
<222> LOCATION: (17)..(17)
<223> OTHER INFORMATION: Xaa is selected from the group consisting of
      Glu, and Gln
<220> FEATURE:
<221> NAME/KEY: MISC_FEATURE
<222> LOCATION: (19)..(19)
<223> OTHER INFORMATION: Xaa is selected from the group consisting
      of Val and Ala
<220> FEATURE:
<221> NAME/KEY: MISC_FEATURE
<222> LOCATION: (20)..(20)
<223> OTHER INFORMATION: Xaa is selected from the group consisting of
      Arg, Lys-Z, Glu, Asp and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
<221> NAME/KEY: MISC_FEATURE
<222> LOCATION: (21)..(21)
<223> OTHER INFORMATION: Xaa is selected from the group consisting
      of Glu and Leu
<220> FEATURE:
<221> NAME/KEY: MISC_FEATURE
<222> LOCATION: (24)..(24)
<223> OTHER INFORMATION: Xaa is selected from the group consisting of
      Ala, Asn, Glu, Lys-Z and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
<221> NAME/KEY: MISC_FEATURE
<222> LOCATION: (27)..(27)
<223> OTHER INFORMATION: Xaa is selected from the group consisting of
      Val and Lys-Z, wherein Z is selected from the group consisting of
      -(Glu)m-PEG, -(Glu)m-biotin and -(Glu)m-fatty acid, or absent and
      m is an integer selected from 0 to 3.
<220> FEATURE:
<221> NAME/KEY: MISC_FEATURE
<222> LOCATION: (28)..(28)
<223> OTHER INFORMATION: Xaa is selected from the group consisting of
      Lys-Z and Asn, wherein Z is selected from the group consisting of
      -(Glu)m-PEG, -(Glu)m-biotin and -(Glu)m-fatty acid, or absent and
      m is an integer selected from 0 to 3.
<220> FEATURE:
<221> NAME/KEY: MISC_FEATURE
<222> LOCATION: (29)..(29)
<223> OTHER INFORMATION: Xaa is linked with a Y, wherein Y is selected
      from the group consisting of: A30 and
      -Gly-Pro-Ser-Ser-Gly-Ala-Pro-Pro-Pro-Ser-A40, or
      absent;A30 and A40 are independently selected from the group
      consisting of -(Lys)n-Z and -Cys-Z, or absent;Z is selected from
      the group consisting of -(Glu)m-PEG, -(Glu)m-biotin and
      -(Glu)m-fatty acid, or absent;n is an integer selected from 1 to
      6;m is an integer selected from 0 to 3

<400> SEQUENCE: 105

Tyr Xaa Glu Gly Thr Phe Xaa Ser Asp Tyr Ser Xaa Xaa Xaa Glu Lys
1               5                   10                  15

Xaa Ala Xaa Xaa Xaa Phe Ile Xaa Trp Leu Xaa Xaa Gly
            20                  25

<210> SEQ ID NO 106
<211> LENGTH: 29
<212> TYPE: PRT
<213> ORGANISM: Artificial
```

```
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa is selected from the group consisting of
      Ala, Gly, Sarcosine, Aib, d-Ala and d-Ser
<220> FEATURE:
<221> NAME/KEY: MISC_FEATURE
<222> LOCATION: (7)..(7)
<223> OTHER INFORMATION: Xaa is selected from the group consisting of
      Thr, Ile and Ser
<220> FEATURE:
<221> NAME/KEY: MISC_FEATURE
<222> LOCATION: (12)..(12)
<223> OTHER INFORMATION: Xaa is selected from the group consisting of
      Ile, Glu and Asp
<220> FEATURE:
<221> NAME/KEY: MISC_FEATURE
<222> LOCATION: (12)..(28)
<223> OTHER INFORMATION: a lactam linkage is optionally formed between
      the amino acids at positions i and i+4 of the GIP analog; i is an
      integer selected from 12 to 24
<220> FEATURE:
<221> NAME/KEY: MISC_FEATURE
<222> LOCATION: (13)..(13)
<223> OTHER INFORMATION: Xaa is selected from the group consisting of an
      amino acid residue having aryl group and is selected from Tyr,
      Phe, Phe(4-F), Phe(4-NO2), Phe(4-NH2), Ala(2-thienyl),
      Ala(benzothienyl) and phenylglycine
<220> FEATURE:
<221> NAME/KEY: MISC_FEATURE
<222> LOCATION: (14)..(14)
<223> OTHER INFORMATION: Xaa is selected from the group consisting of
      Met or oxidized Met, Leu, Val, Norleucine and Ile
<220> FEATURE:
<221> NAME/KEY: MISC_FEATURE
<222> LOCATION: (17)..(17)
<223> OTHER INFORMATION: Xaa is selected from the group consisting of
      Glu, and Gln
<220> FEATURE:
<221> NAME/KEY: MISC_FEATURE
<222> LOCATION: (19)..(19)
<223> OTHER INFORMATION: Xaa is selected from the group consisting of
      Val and Ala
<220> FEATURE:
<221> NAME/KEY: MISC_FEATURE
<222> LOCATION: (20)..(20)
<223> OTHER INFORMATION: Xaa is selected from the group consisting of
      Arg, Lys-Z, Glu, Asp and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
<221> NAME/KEY: MISC_FEATURE
<222> LOCATION: (21)..(21)
<223> OTHER INFORMATION: Xaa is selected from the group consisting of
      Glu and Leu
<220> FEATURE:
<221> NAME/KEY: MISC_FEATURE
<222> LOCATION: (24)..(24)
<223> OTHER INFORMATION: Xaa is selected from the group consisting of
      Ala, Asn, Glu, Lys-Z and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
<221> NAME/KEY: MISC_FEATURE
<222> LOCATION: (27)..(27)
<223> OTHER INFORMATION: Xaa is selected from the group consisting of
      Val and Lys-Z, wherein Z is selected from the group consisting of
      -(Glu)m-PEG, -(Glu)m-biotin and -(Glu)m-fatty acid, or absent and
      m is an integer selected from 0 to 3.
<220> FEATURE:
<221> NAME/KEY: MISC_FEATURE
<222> LOCATION: (28)..(28)
<223> OTHER INFORMATION: Xaa is selected from the group consisting of
      Lys-Z and Asn, wherein Z is selected from the group consisting
      of -(Glu)m-PEG, -(Glu)m-biotin and -(Glu)m-fatty acid, or absent
      and m is an integer selected from 0 to 3.
```

-continued

```
<400> SEQUENCE: 106

Tyr Xaa Glu Gly Thr Phe Xaa Ser Asp Tyr Ser Xaa Xaa Xaa Glu Lys
1               5                   10                  15

Xaa Ala Xaa Xaa Xaa Phe Ile Xaa Trp Leu Xaa Xaa Gly
            20                  25

<210> SEQ ID NO 107
<211> LENGTH: 10
<212> TYPE: PRT
<213> ORGANISM: Artificial
<220> FEATURE:
<223> OTHER INFORMATION: peptide fragment

<400> SEQUENCE: 107

Gly Pro Ser Ser Gly Ala Pro Pro Pro Ser
1               5                   10

<210> SEQ ID NO 108
<211> LENGTH: 39
<212> TYPE: PRT
<213> ORGANISM: Artificial
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa is selected from the group consisting of
      Ala, Gly, Sarcosine, Aib, d-Ala and d-Ser
<220> FEATURE:
<221> NAME/KEY: MISC_FEATURE
<222> LOCATION: (7)..(7)
<223> OTHER INFORMATION: Xaa is selected from the group consisting of
      Thr, Ile and Ser
<220> FEATURE:
<221> NAME/KEY: MISC_FEATURE
<222> LOCATION: (12)..(12)
<223> OTHER INFORMATION: Xaa is selected from the group consisting of
      Ile, Glu and Asp
<220> FEATURE:
<221> NAME/KEY: MISC_FEATURE
<222> LOCATION: (12)..(28)
<223> OTHER INFORMATION: a lactam linkage is optionally formed between
      the amino acids at positions i and i+4 of the GIP analog; i is an
      integer selected from 12 to 24
<220> FEATURE:
<221> NAME/KEY: MISC_FEATURE
<222> LOCATION: (13)..(13)
<223> OTHER INFORMATION: Xaa is selected from the group consisting of
      an amino acid residue having aryl group and is selected from Tyr,
      Phe, Phe(4-F), Phe(4-NO2), Phe(4-NH2), Ala(2-thienyl),
      Ala(benzothienyl) and phenylglycine
<220> FEATURE:
<221> NAME/KEY: MISC_FEATURE
<222> LOCATION: (14)..(14)
<223> OTHER INFORMATION: Xaa is selected from the group consisting of
      Met or oxidized Met, Leu, Val, Norleucine and Ile
<220> FEATURE:
<221> NAME/KEY: MISC_FEATURE
<222> LOCATION: (17)..(17)
<223> OTHER INFORMATION: Xaa is selected from the group consisting of
      Glu, and Gln
<220> FEATURE:
<221> NAME/KEY: MISC_FEATURE
<222> LOCATION: (19)..(19)
<223> OTHER INFORMATION: Xaa is selected from the group consisting of
      Val and Ala
<220> FEATURE:
<221> NAME/KEY: MISC_FEATURE
<222> LOCATION: (20)..(20)
<223> OTHER INFORMATION: Xaa is selected from the group consisting of
      Arg, Lys-Z, Glu, Asp and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
```

```
<221> NAME/KEY: MISC_FEATURE
<222> LOCATION: (21)..(21)
<223> OTHER INFORMATION: Xaa is selected from the group consisting of
      Glu and Leu
<220> FEATURE:
<221> NAME/KEY: MISC_FEATURE
<222> LOCATION: (24)..(24)
<223> OTHER INFORMATION: Xaa is selected from the group consisting of
      Ala, Asn, Glu, Lys-Z and Cys-Z, wherein Z is selected from the
      group consisting of -(Glu)m-PEG, -(Glu)m-biotin and -(Glu)m-fatty
      acid, or absent and m is an integer selected from 0 to 3.
<220> FEATURE:
<221> NAME/KEY: MISC_FEATURE
<222> LOCATION: (27)..(27)
<223> OTHER INFORMATION: Xaa is selected from the group consisting of
      Val and Lys-Z, wherein Z is selected from the group consisting of
      -(Glu)m-PEG, -(Glu)m-biotin and -(Glu)m-fatty acid, or absent and
      m is an integer selected from 0 to 3.
<220> FEATURE:
<221> NAME/KEY: MISC_FEATURE
<222> LOCATION: (28)..(28)
<223> OTHER INFORMATION: Xaa is selected from the group consisting of
      Lys-Z and Asn, wherein Z is selected from the group consisting of
      -(Glu)m-PEG, -(Glu)m-biotin and -(Glu)m-fatty acid, or absent and
      m is an integer selected from 0 to 3.

<400> SEQUENCE: 108

Tyr Xaa Glu Gly Thr Phe Xaa Ser Asp Tyr Ser Xaa Xaa Xaa Glu Lys
1               5                   10                  15

Xaa Ala Xaa Xaa Xaa Phe Ile Xaa Trp Leu Xaa Xaa Gly Gly Pro Ser
            20                  25                  30

Ser Gly Ala Pro Pro Pro Ser
            35

<210> SEQ ID NO 109
<211> LENGTH: 29
<212> TYPE: PRT
<213> ORGANISM: Artificial
<220> FEATURE:
<223> OTHER INFORMATION: GIP analog
<220> FEATURE:
<221> NAME/KEY: MISC_FEATURE
<222> LOCATION: (2)..(2)
<223> OTHER INFORMATION: Xaa is selected from the group consisting of
      Ala, Gly, Aib and d-Ala
<220> FEATURE:
<221> NAME/KEY: MISC_FEATURE
<222> LOCATION: (12)..(28)
<223> OTHER INFORMATION: a lactam linkage is optionally formed between
      the amino acids at positions i and i+4 of the GIP analog; i is an
      integer selected from 12 to 24
<220> FEATURE:
<221> NAME/KEY: MISC_FEATURE
<222> LOCATION: (13)..(13)
<223> OTHER INFORMATION: Xaa is selected from the group consisting of an
      amino acid residue having aryl group and is selected from Tyr,
      Phe, Phe(4-F), Phe(4-NO2) and Phe(4-NH2)
<220> FEATURE:
<221> NAME/KEY: MISC_FEATURE
<222> LOCATION: (17)..(17)
<223> OTHER INFORMATION: Xaa is selected from the group consisting
      of Ile, Glu, and Gln
<220> FEATURE:
<221> NAME/KEY: MISC_FEATURE
<222> LOCATION: (18)..(18)
<223> OTHER INFORMATION: Xaa is selected from the group consisting
      of Ala and His
<220> FEATURE:
<221> NAME/KEY: MISC_FEATURE
<222> LOCATION: (19)..(19)
<223> OTHER INFORMATION: Xaa is selected from the group consisting
      of Val, Ala, Leu, Gln and Ile
<220> FEATURE:
<221> NAME/KEY: MISC_FEATURE
<222> LOCATION: (20)..(20)
```

```
<223> OTHER INFORMATION: Xaa is selected from the group consisting of
      Arg, Lys-Z, Gln, Glu, Asp and Cys-Z, wherein Z is selected from
      the group consisting of -(Glu)m-PEG, -(Glu)m-biotin and
      -(Glu)m-fatty acid, or absent and m is an integer selected from
      0 to 3.
<220> FEATURE:
<221> NAME/KEY: MISC_FEATURE
<222> LOCATION: (21)..(21)
<223> OTHER INFORMATION: Xaa is selected from the group consisting
      of Glu, Asp and Leu
<220> FEATURE:
<221> NAME/KEY: MISC_FEATURE
<222> LOCATION: (22)..(22)
<223> OTHER INFORMATION: Xaa is selected from the group consisting
      of Phe, Phe(4-F) and Phe(4-Cl)
<220> FEATURE:
<221> NAME/KEY: MISC_FEATURE
<222> LOCATION: (23)..(23)
<223> OTHER INFORMATION: Xaa is selected from the group consisting
      of Ile and Val
<220> FEATURE:
<221> NAME/KEY: MISC_FEATURE
<222> LOCATION: (24)..(24)
<223> OTHER INFORMATION: Xaa is selected from the group consisting of
      Ala, Asn, Glu, Lys-Z and Cys-Z, wherein Z is selected from the
      group consisting of -(Glu)m-PEG, -(Glu)m-biotin and
      -(Glu)m-fatty acid, or absent and m is an integer selected from
      0 to 3.
<220> FEATURE:
<221> NAME/KEY: MISC_FEATURE
<222> LOCATION: (27)..(27)
<223> OTHER INFORMATION: Xaa is selected from the group consisting of
      Val, Leu, Ala and Lys-Z, wherein Z is selected from the group
      consisting of -(Glu)m-PEG, -(Glu)m-biotin and -(Glu)m-fatty acid,
      or absent and m is an integer selected from 0 to 3.
<220> FEATURE:
<221> NAME/KEY: MISC_FEATURE
<222> LOCATION: (28)..(28)
<223> OTHER INFORMATION: Xaa is selected from the group consisting of
      Lys-Z, Ala, Arg, and Asn, wherein Z is selected from the group
      consisting of -(Glu)m-PEG, -(Glu)m-biotin and -(Glu)m-fatty acid,
      or absent and m is an integer selected from 0 to 3.
<220> FEATURE:
<221> NAME/KEY: MISC_FEATURE
<222> LOCATION: (29)..(29)
<223> OTHER INFORMATION: Xaa is selected from the group consisting
      of Gly, Gln and Arg
<220> FEATURE:
<221> NAME/KEY: MISC_FEATURE
<222> LOCATION: (29)..(29)
<223> OTHER INFORMATION: Xaa is linked with a Y, wherein Y is selected
      from the group consisting of: A30 and
      -Gly-Pro-Ser-Ser-Gly-Ala-Pro-Pro-Pro-Ser-A40, or
      absent;A30 and A40 are independently selected from the group
      consisting of -(Lys)n-Z and -Cys-Z, or absent;Z is selected from
      the group consisting of -(Glu)m-PEG, -(Glu)m-biotin and
      -(Glu)m-fatty acid, or absent;n is an integer selected from 1 to
      6;m is an integer selected from 0 to 3

<400> SEQUENCE: 109

Tyr Xaa Glu Gly Thr Phe Thr Ser Asp Tyr Ser Ile Xaa Met Glu Lys
1               5                   10                  15

Xaa Xaa Xaa Xaa Xaa Xaa Xaa Xaa Trp Leu Xaa Xaa Xaa
            20                  25
```

We claim:

1. A glucose-dependent insulinotropic polypeptide (GIP) analog derived from GIP (1-29, SEQ ID NO: 1), wherein the GIP analog has both GLP-1 agonist activity and GIPR stimulation activity, is amidated at the C-terminus thereof, and comprises an amino acid sequence represented by the following formula I:

Tyr-A2-Glu-Gly-Thr-Phe-Thr-Ser-Asp-Tyr-Ser-Ile-A13-Met-Glu-Lys-A17-A18-A19-A20-A21-A22-A23-A24-Trp-Leu-A27-A28-A29-Y  (SEQ ID NO: 109)

wherein

A2 is selected from the group consisting of Gly, Aib, and d-Ala;

A13 is selected from the group consisting of an amino acid residue having aryl group and is selected from Tyr, Phe(4-F), Phe(4-NO$_2$), and Phe(4-NH$_2$);

A17 is selected from the group consisting of Ile, Glu, and Gln;

A18 is selected from the group consisting of Ala and His;

A19 is selected from the group consisting of Val, Ala, Leu, Gln and Ile;
A20 is selected from the group consisting of Arg, Lys-Z, Gln, Glu, Asp and Cys-Z;
A21 is selected from the group consisting of Glu, Asp and Leu;
A22 is selected from the group consisting of Phe, Phe(4-F), and Phe(4-Cl);
A23 is selected from the group consisting of Ile and Val;
A24 is selected from the group consisting of Ala, Glu, Lys-Z and Cys-Z;
A27 is selected from the group consisting of Val, Leu, Ala, and Lys-Z;
A28 is selected from the group consisting of Lys-Z, Ala, Arg, and Asn;
A29 is selected from the group consisting of Gly, Gln and Arg;
Y is selected from the group consisting of: A30 and -Gly-Pro-Ser-Ser-Gly-Ala-Pro-Pro-Pro-Ser-A40 (SEQ ID NO: 104), or absent;
A30 and A40 are independently selected from the group consisting of -(Lys)$_n$-Z and -Cys-Z, or absent;
Z is selected from the group consisting of -(Glu)$_m$-PEG, -(Glu)$_m$-biotin and -(Glu)$_m$-fatty acid, or absent;
n is an integer selected from 1 to 6;
m is an integer selected from 0 to 3;
wherein, a lactam linkage is optionally formed between the amino acids at positions i and i+4 of the GIP analog; i is an integer selected from 12 to 24;
or a pharmaceutically acceptable salt thereof,
wherein the GLP-1 agonist activity is more dominant than the GIPR stimulation activity.

2. The GIP analog according to claim 1, wherein in formula I:
A13 is selected from the group consisting of an amino acid residue having aryl group and is selected from Tyr, Phe(4-F), Phe(4-NO$_2$), and Phe(4-NH$_2$)
A18 is Ala;
A19 is selected from the group consisting of Val and Ala;
A20 is selected from the group consisting of Arg, Lys-Z, Glu, Asp and Cys-Z;
A21 is selected from the group consisting of Glu and Leu;
A22 is Phe;
A23 is Ile;
A27 is selected from the group consisting of Val and Lys-Z;
A28 is selected from the group consisting of Lys-Z and Asn; and
A29 is Gly;
Z is selected from the group consisting of -(Glu)$_m$-PEG, -(Glu)$_m$-biotin and -(Glu)$_m$-fatty acid, or absent;
m is an integer selected from 0 to 3.

3. The GIP analog according to claim 1, wherein in formula I,
Y is A30 or absent;
A30 is selected from the group consisting of -(Lys)$_n$-Z and -Cys-Z, or absent;
Z is selected from the group consisting of -(Glu)$_m$-PEG, -(Glu)$_m$-biotin and -(Glu)$_m$-fatty acid, or absent;
n is an integer selected from 1 to 6;
m is an integer selected from 0 to 3.

4. The GIP analog according to claim 1, wherein in formula I,
Y is Gly-Pro-Ser-Ser-Gly-Ala-Pro-Pro-Pro-Ser-A40 (SEQ ID NO: 104);
A40 is selected from the group consisting of -(Lys)$_n$-Z and -Cys-Z, or absent;
Z is selected from the group consisting of -(Glu)$_m$-PEG, -(Glu)$_m$-biotin and -(Glu)$_m$-fatty acid, or absent;
n is an integer selected from 1 to 6;
m is an integer selected from 0 to 3.

5. The GIP analog according to claim 1, wherein in formula I: Y is absent.

6. The GIP analog according to claim 1, wherein in formula I: Y is Gly-Pro-Ser-Ser-Gly-Ala-Pro-Pro-Pro-Ser (SEQ ID NO: 107).

7. The GIP analog according to claim 1, wherein formula I comprises one or more amino acids selected from the group consisting of: Aib at position A2; Tyr at position A13; Glu at position A17; Val at position A19; and Arg at position A20.

8. The GIP analog according to claim 1, wherein in formula I:
A24 is Cys-Z;
Z is -(Glu)$_m$-PEG;
m is an integer selected from 0 to 3.

9. The GIP analog according to claim 1, wherein in formula I:
A30 and A40 are independently (Lys)$_n$-Z;
Z is selected from the group consisting of -(Glu)$_m$-PEG, -(Glu)$_m$-biotin and -(Glu)$_m$-fatty acid, or absent;
n is an integer selected from 1 to 6;
m is an integer selected from 0 to 3.

10. The GIP analog according to claim 1, wherein in formula I:
Z is selected from the group consisting of -(Glu)$_m$-PEG and -(Glu)$_m$-fatty acid; and
m is an integer selected from 0 to 2.

11. The GIP analog according to claim 1, wherein in formula I, a lactam linkage is formed between the amino acids at positions i and i+4 of the GIP analog; i is an integer selected from 12, 16 and 24.

12. The GIP analog according to claim 1, wherein the fatty acid is selected from the group consisting of myristic acid, palmitic acid, stearic acid and cholic acid.

13. The GIP analog according to claim 1, wherein the molecular weight of PEG is from 5 kDa to 40 kDa.

14. The GIP analog according to claim 1, wherein the GIP analog comprises an amino acid sequence selected from the group consisting of SEQ ID NOs: 65, 18 to 21, 24 to 35, 38 to 47, 49 to 59, 62 to 64, 66 to 74, 76 to 78 and 80 to 83; or a pharmaceutically acceptable salt thereof.

15. The GIP analog according to claim 1, wherein the GIP analog comprises an amino acid sequence selected from the group consisting of SEQ ID NOs: 65, 63, 80, 52, 18, 35, 74, 19, 20, 21, 45, and 72; or a pharmaceutically acceptable salt thereof.

16. The GIP analog according to claim 1, wherein the GIP analog comprises an amino acid sequence selected from the group consisting of:
SEQ ID NO: 52, wherein at least one fatty acid moiety is linked at position 20, 24 and/or the C-terminal;
SEQ ID NO: 74, wherein at least one fatty acid moiety is linked at position 20, 24 and/or the C-terminal;
SEQ ID NO: 72 wherein at least one fatty acid moiety is linked at position 20, 24 and/or the C-terminal;
SEQ ID NO: 98, wherein at least one PEG moiety is linked at position 20, 24 and/or the C-terminal;
SEQ ID NO: 74, wherein at least one PEG moiety is linked at position 20, 24 and/or the C-terminal;
SEQ ID NO: 65, wherein at least one PEG moiety is linked at position 20, 24 and/or the C-terminal;

SEQ ID NO: 74 with PEG moiety linked at position 24 and a fatty acid moiety linked at the C-terminal; and pharmaceutically acceptable salts thereof.

17. The GIP analog according to claim 10, wherein Glu is gamma-Glu.

18. The GIP analog according to claim 1, wherein the molecular weight of PEG is 20 kDa, 30 kDa, or 40 kDa.

19. A pharmaceutical composition comprising an effective amount of a GIP analog according to claim 1, a pharmaceutically acceptable diluent, carrier or excipient, and an optional anti-diabetes agent selected from the group consisting of insulins, biguanides, sulfonylurea, rosiglitazone, pioglitazone, alpha-glucosaccharase inhibitors, and aminodipeptidase IV inhibitors.

20. The pharmaceutical composition according to claim 19, wherein the pharmaceutical composition is in the form of an injectable formulation or lyophilized powder.

21. A method for treating metabolic disorders, comprising administering an effective amount of the GIP analog or the pharmaceutically acceptable salt thereof according to claim 1 to a subject in need thereof.

22. The method according to claim 21, wherein the metabolic disorder is selected from the group consisting of diabetes mellitus, obesity and osteoporosis.

* * * * *